US011213593B2

(12) United States Patent
Mirkin et al.

(10) Patent No.: US 11,213,593 B2
(45) Date of Patent: Jan. 4, 2022

(54) SEQUENCE-SPECIFIC CELLULAR UPTAKE OF SPHERICAL NUCLEIC ACID NANOPARTICLE CONJUGATES

(71) Applicant: NORTHWESTERN UNIVERSITY, Evanston, IL (US)

(72) Inventors: Chad A. Mirkin, Wilmette, IL (US); Chung Hang J. Choi, Evanston, IL (US); Suguna P. Narayan, Evanston, IL (US); Liangliang Hao, Cambridge, MA (US); Evelyn Auyeung, New York, NY (US)

(73) Assignee: Northwestern University, Evanston, IL (US)

( * ) Notice: Subject to any disclaimer, the term of this patent is extended or adjusted under 35 U.S.C. 154(b) by 257 days.

(21) Appl. No.: 15/527,840

(22) PCT Filed: Nov. 20, 2015

(86) PCT No.: PCT/US2015/062005
§ 371 (c)(1),
(2) Date: May 18, 2017

(87) PCT Pub. No.: WO2016/081911
PCT Pub. Date: May 26, 2016

(65) Prior Publication Data
US 2018/0344873 A1    Dec. 6, 2018

Related U.S. Application Data

(60) Provisional application No. 62/083,092, filed on Nov. 21, 2014.

(51) Int. Cl.
| A61K 47/69 | (2017.01) |
| C12N 15/88 | (2006.01) |
| A61K 9/51 | (2006.01) |
| A61K 47/54 | (2017.01) |

(52) U.S. Cl.
CPC ........ *A61K 47/6929* (2017.08); *A61K 9/5115* (2013.01); *A61K 47/549* (2017.08); *A61K 47/6923* (2017.08); *C12N 15/88* (2013.01)

(58) Field of Classification Search
CPC ... A61K 31/713; A61K 31/7088; A61P 35/00; C12N 15/88; C12N 15/1131; C12N 15/113; C12N 2310/14; C12N 2310/50; C12N 2320/30
USPC .......... 435/6.1, 6.12, 91.1, 91.31, 455, 458; 514/44 A; 536/23.1, 24.5
See application file for complete search history.

(56) References Cited

U.S. PATENT DOCUMENTS

| 3,687,808 A | 8/1972 | Merigan, Jr. et al. |
| 4,179,337 A | 12/1979 | Davis et al. |
| 4,289,872 A | 9/1981 | Denkewalter et al. |
| 4,301,144 A | 11/1981 | Iwashita et al. |
| 4,469,863 A | 9/1984 | Ts'o et al. |
| 4,476,301 A | 10/1984 | Imbach et al. |
| 4,489,055 A | 12/1984 | Couvreur et al. |
| 4,496,689 A | 1/1985 | Mitra |
| 4,587,044 A | 5/1986 | Miller et al. |
| 4,605,735 A | 8/1986 | Miyoshi et al. |
| 4,640,835 A | 2/1987 | Shimizu et al. |
| 4,667,025 A | 5/1987 | Miyoshi et al. |
| 4,670,417 A | 6/1987 | Iwasaki et al. |
| 4,762,779 A | 8/1988 | Snitman |
| 4,789,737 A | 12/1988 | Miyoshi et al. |
| 4,791,192 A | 12/1988 | Nakagawa et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,008,050 A | 4/1991 | Cullis et al. |
| 5,013,830 A | 5/1991 | Ohtsuka et al. |

(Continued)

FOREIGN PATENT DOCUMENTS

| AU | 2004218696 A1 | 11/2004 |
| CN | 101180400 A | 5/2008 |

(Continued)

OTHER PUBLICATIONS

Niemeyer, et al. (2003) "Bifunctional DNA-gold nanoparticle conjugates as building blocks for the self-assembly of cross-linked particle layers," Biochemical and Biophysical Research Communications, vol. 311:995-9. (Year: 2003).*

(Continued)

*Primary Examiner* — Jane J Zara
(74) *Attorney, Agent, or Firm* — Wolf, Greenfield & Sacks, P.C.

(57) ABSTRACT

Spherical nucleic acids (SNAs), consisting of densely packed, highly oriented polynucleotide strands attached to the surface of nanoparticles, are able to overcome the typical challenges of nucleic acid delivery. The present disclosure demonstrates that G-rich SNAs exhibit several-fold higher uptake into cells relative to SNAs rich in other nucleotides. This disclosure provides an effective strategy to maximize the intracellular delivery of SNAs, which is applicable to other nanoparticle systems, thus establishing an important design consideration for nanoparticle-based intracellular delivery of therapeutics.

35 Claims, 20 Drawing Sheets

Specification includes a Sequence Listing.

(56) References Cited

U.S. PATENT DOCUMENTS

| | | |
|---|---|---|
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,229,490 A | 7/1993 | Tam |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,457,272 A | 10/1995 | Hooykaas |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,472,881 A | 12/1995 | Beebe et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,728,527 A | 3/1998 | Singer et al. |
| 5,750,692 A | 5/1998 | Cook et al. |
| 5,763,588 A | 6/1998 | Matteucci et al. |
| 5,780,448 A | 7/1998 | Davis |
| 5,792,608 A | 8/1998 | Swaminathan et al. |
| 5,792,747 A | 8/1998 | Schally et al. |

(56) References Cited

U.S. PATENT DOCUMENTS

| | | |
|---|---|---|
| 5,830,653 A | 11/1998 | Froehler et al. |
| 5,955,589 A | 9/1999 | Cook et al. |
| 6,005,096 A | 12/1999 | Matteucci et al. |
| 6,080,580 A | 6/2000 | Baker et al. |
| 6,194,388 B1 | 2/2001 | Krieg et al. |
| 6,207,646 B1 | 3/2001 | Krieg et al. |
| 6,228,642 B1 | 5/2001 | Baker et al. |
| 6,239,116 B1 | 5/2001 | Krieg et al. |
| 6,271,209 B1 | 8/2001 | Smith et al. |
| 6,287,860 B1 | 9/2001 | Monia et al. |
| 6,361,944 B1 | 3/2002 | Mirkin et al. |
| 6,403,312 B1 | 6/2002 | Dahiyat et al. |
| 6,406,705 B1 | 6/2002 | Davis et al. |
| 6,417,340 B1 | 7/2002 | Mirkin et al. |
| 6,495,324 B1 | 12/2002 | Mirkin et al. |
| 6,506,564 B1 | 1/2003 | Mirkin et al. |
| 6,534,062 B2 | 3/2003 | Raz et al. |
| 6,544,776 B1 | 4/2003 | Gold et al. |
| 6,582,921 B2 | 6/2003 | Mirkin et al. |
| 6,602,669 B2 | 8/2003 | Letsinger et al. |
| 6,610,308 B1 | 8/2003 | Haensler |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,678,548 B1 | 1/2004 | Echauz et al. |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,806,289 B1 | 10/2004 | Lippard et al. |
| 6,812,334 B1 | 11/2004 | Mirkin et al. |
| 6,818,753 B2 | 11/2004 | Mirkin et al. |
| 6,827,979 B2 | 12/2004 | Mirkin et al. |
| 6,828,432 B2 | 12/2004 | Mirkin et al. |
| 6,844,161 B2 | 1/2005 | Siani et al. |
| 6,849,725 B2 | 2/2005 | Junghans et al. |
| 6,861,221 B2 | 3/2005 | Mirkin et al. |
| 6,878,814 B2 | 4/2005 | Mirkin et al. |
| 6,942,972 B2 | 9/2005 | Farooqui et al. |
| 6,974,669 B2 | 12/2005 | Mirkin et al. |
| 6,991,900 B2 | 1/2006 | Shizuya |
| 7,038,029 B2 | 5/2006 | Lopez |
| 7,048,949 B2 | 5/2006 | Sligar et al. |
| 7,098,320 B1 | 8/2006 | Mirkin et al. |
| 7,129,222 B2 | 10/2006 | Van Nest et al. |
| 7,138,520 B2 | 11/2006 | Lippard et al. |
| 7,176,296 B2 | 2/2007 | Agrawal et al. |
| 7,208,587 B2 | 4/2007 | Mirkin et al. |
| 7,223,741 B2 | 5/2007 | Krieg |
| 7,223,833 B1 | 5/2007 | Nielsen et al. |
| 7,238,472 B2 | 7/2007 | Mirkin et al. |
| 7,250,403 B2 | 7/2007 | Nest et al. |
| 7,255,868 B2 | 8/2007 | Fearon et al. |
| 7,262,286 B2 | 8/2007 | Kandimalla et al. |
| 7,276,489 B2 | 10/2007 | Agrawal et al. |
| 7,291,284 B2 | 11/2007 | Mirkin et al. |
| 7,323,309 B2 | 1/2008 | Mirkin et al. |
| 7,332,586 B2 | 2/2008 | Franzen et al. |
| 7,354,907 B2 | 4/2008 | Agrawal et al. |
| 7,387,271 B2 | 6/2008 | Noelle et al. |
| 7,404,969 B2 | 7/2008 | Chen et al. |
| 7,427,405 B2 | 9/2008 | Agrawal et al. |
| 7,470,674 B2 | 12/2008 | Agrawal et al. |
| 7,514,099 B2 | 4/2009 | Chen et al. |
| 7,563,618 B2 | 7/2009 | Gryaznov et al. |
| 7,569,553 B2 | 8/2009 | Krieg |
| 7,569,554 B2 | 8/2009 | Kandimalla et al. |
| 7,595,305 B2 | 9/2009 | Agrawal et al. |
| 7,611,728 B2 | 11/2009 | Kidane et al. |
| 7,615,539 B2 | 11/2009 | Uhlmann et al. |
| 7,628,990 B2 | 12/2009 | Tuck et al. |
| 7,638,557 B2 | 12/2009 | Lipkin et al. |
| 7,651,979 B2 | 1/2010 | Lippard et al. |
| 7,666,674 B2 | 2/2010 | Klinman et al. |
| 7,667,004 B2 | 2/2010 | Zhong et al. |
| 7,709,617 B2 | 5/2010 | Kandimalla et al. |
| 7,713,535 B2 | 5/2010 | Agrawal et al. |
| 7,718,622 B2 | 5/2010 | Tuck et al. |
| 7,727,969 B2 | 6/2010 | Farokhzad et al. |
| 7,745,606 B2 | 6/2010 | Dina et al. |
| 7,776,834 B2 | 8/2010 | Agrawal et al. |
| 7,786,089 B2 | 8/2010 | Kandimalla et al. |
| 7,833,992 B2 | 11/2010 | Vargeese et al. |
| 7,851,453 B2 | 12/2010 | Agrawal et al. |
| 7,875,594 B2 | 1/2011 | Kandimalla et al. |
| 7,884,083 B2 | 2/2011 | van Nest et al. |
| 7,956,176 B2 | 6/2011 | McSwiggen et al. |
| 7,960,362 B2 | 6/2011 | Kandimalla et al. |
| 7,964,578 B2 | 6/2011 | Vargeese et al. |
| 8,008,266 B2 | 8/2011 | Krieg et al. |
| 8,008,267 B2 | 8/2011 | Kandimalla et al. |
| 8,017,591 B2 | 9/2011 | Brzezicha et al. |
| 8,058,249 B2 | 11/2011 | Krieg et al. |
| 8,088,388 B2 | 1/2012 | Sokoll |
| 8,124,590 B2 | 2/2012 | van Nest et al. |
| 8,128,944 B2 | 3/2012 | Jurk et al. |
| 8,158,768 B2 | 4/2012 | Dina et al. |
| 8,188,261 B2 | 5/2012 | Kandimalla et al. |
| 8,202,979 B2 | 6/2012 | McSwiggen et al. |
| 8,273,866 B2 | 9/2012 | McSwiggen et al. |
| 8,283,328 B2 | 10/2012 | Krieg et al. |
| 8,304,396 B2 | 11/2012 | Krieg et al. |
| 8,309,527 B2 | 11/2012 | Krieg et al. |
| 8,323,686 B2 | 12/2012 | Mirkin et al. |
| 8,333,980 B2 | 12/2012 | van Nest et al. |
| 8,431,544 B1 | 4/2013 | Agrawal et al. |
| 8,507,200 B2 | 8/2013 | Mirkin et al. |
| 8,853,375 B2 | 10/2014 | Kandimalla et al. |
| 8,871,732 B2 | 10/2014 | Dina et al. |
| 8,889,181 B2 | 11/2014 | Kwon |
| 8,945,590 B2 | 2/2015 | Fairman et al. |
| 8,968,746 B2 | 3/2015 | Baumhof et al. |
| 8,987,221 B2 | 3/2015 | Zhu et al. |
| 9,061,001 B2 | 6/2015 | van Drunen Littel-van den Hurk et al. |
| 9,066,978 B2 | 6/2015 | Ilyinskii et al. |
| 9,139,827 B2 | 9/2015 | Mirkin et al. |
| 9,200,287 B2 | 12/2015 | Uhlmann et al. |
| 9,212,366 B2 | 12/2015 | Wittig et al. |
| 9,265,729 B2 | 2/2016 | Nakamura |
| 9,364,443 B2 | 6/2016 | Beduneau et al. |
| 9,499,815 B1 | 11/2016 | Schroff et al. |
| 9,506,056 B2 | 11/2016 | Mirkin et al. |
| 9,522,958 B2 | 12/2016 | Epstein et al. |
| 9,532,948 B2 | 1/2017 | Mirkin et al. |
| 9,549,901 B2 | 1/2017 | Shi et al. |
| 9,580,708 B2 | 2/2017 | Uhlmann et al. |
| 9,617,541 B2 | 4/2017 | Mirkin et al. |
| 9,844,562 B2 | 12/2017 | Mirkin et al. |
| 9,868,955 B2 | 1/2018 | Guiducci et al. |
| 9,889,209 B2 | 2/2018 | Mirkin et al. |
| 9,901,616 B2 | 2/2018 | Dhar et al. |
| 9,907,845 B2 | 3/2018 | Reed et al. |
| 9,907,862 B2 | 3/2018 | Baumhof et al. |
| 9,950,063 B2 | 4/2018 | Reed et al. |
| 9,950,064 B2 | 4/2018 | Ott et al. |
| 9,987,355 B2 | 6/2018 | Reed et al. |
| 9,993,495 B2 | 6/2018 | Guiducci et al. |
| 9,999,673 B2 | 6/2018 | Rajeev et al. |
| 10,029,016 B2 | 7/2018 | Irvine et al. |
| 10,098,958 B2 | 10/2018 | Mirkin et al. |
| 10,117,919 B2 | 11/2018 | Knutson et al. |
| 10,144,933 B2 | 12/2018 | Gemba et al. |
| 10,149,905 B2 | 12/2018 | Gemba et al. |
| 10,155,950 B2 | 12/2018 | Munnes et al. |
| 10,182,988 B2 | 1/2019 | Mirkin et al. |
| 10,196,643 B2 | 2/2019 | Dina et al. |
| 10,208,310 B2 | 2/2019 | Mader et al. |

(56) References Cited

U.S. PATENT DOCUMENTS

| | | | |
|---|---|---|---|
| 10,280,424 B2 | 5/2019 | Kleuss et al. | |
| 10,322,173 B2 | 6/2019 | Gemba et al. | |
| 10,370,656 B2 | 8/2019 | Mirkin et al. | |
| 10,391,116 B2 | 8/2019 | Mirkin et al. | |
| 10,398,784 B2 | 9/2019 | Mirkin et al. | |
| 10,449,212 B2 | 10/2019 | Hanagata et al. | |
| 10,487,333 B2 | 11/2019 | Schroff et al. | |
| 10,792,251 B2 | 10/2020 | Mirkin et al. | |
| 2002/0156033 A1 | 10/2002 | Bratzler et al. | |
| 2002/0172711 A1 | 11/2002 | Martin et al. | |
| 2002/0172953 A1 | 11/2002 | Mirkin et al. | |
| 2002/0197269 A1 | 12/2002 | Lingnau et al. | |
| 2003/0022848 A1 | 1/2003 | Baker et al. | |
| 2003/0026782 A1 | 2/2003 | Krieg et al. | |
| 2003/0044354 A1 | 3/2003 | Carpenter et al. | |
| 2003/0050261 A1 | 3/2003 | Krieg et al. | |
| 2003/0091599 A1 | 5/2003 | Krieg et al. | |
| 2003/0104044 A1 | 6/2003 | Semple et al. | |
| 2003/0129251 A1 | 7/2003 | Van Nest et al. | |
| 2003/0133988 A1 | 7/2003 | Fearon et al. | |
| 2003/0138413 A1 | 7/2003 | Vicari et al. | |
| 2003/0147966 A1 | 8/2003 | Franzen et al. | |
| 2003/0170162 A1 | 9/2003 | Nayfeh et al. | |
| 2003/0181412 A1 | 9/2003 | Erikson | |
| 2003/0212026 A1 | 11/2003 | Krieg et al. | |
| 2004/0014956 A1 | 1/2004 | Woolf et al. | |
| 2004/0053384 A1 | 3/2004 | Sligar et al. | |
| 2004/0087534 A1 | 5/2004 | Krieg et al. | |
| 2004/0092468 A1 | 5/2004 | Schwartz | |
| 2004/0131628 A1 | 7/2004 | Bratzler et al. | |
| 2004/0143112 A1 | 7/2004 | Krieg et al. | |
| 2004/0158051 A1 | 8/2004 | Ozkan et al. | |
| 2004/0219565 A1 | 11/2004 | Kauppinen et al. | |
| 2004/0247680 A1 | 12/2004 | Farokhzad et al. | |
| 2004/0248099 A1 | 12/2004 | Goppelt et al. | |
| 2004/0266719 A1 | 12/2004 | McCluskie et al. | |
| 2005/0009773 A1 | 1/2005 | Kandimalla et al. | |
| 2005/0059016 A1 | 3/2005 | Ecker et al. | |
| 2005/0074753 A1 | 4/2005 | Goldsborough | |
| 2005/0089890 A1 | 4/2005 | Cubicciotti | |
| 2005/0090671 A1 | 4/2005 | Chang et al. | |
| 2005/0096263 A1 | 5/2005 | Keay et al. | |
| 2005/0136258 A1 | 6/2005 | Nie et al. | |
| 2005/0169888 A1 | 8/2005 | Hartman et al. | |
| 2005/0197315 A1 | 9/2005 | Taira et al. | |
| 2005/0214782 A1 | 9/2005 | Chen et al. | |
| 2005/0244858 A1 | 11/2005 | Rossi et al. | |
| 2006/0003962 A1 | 1/2006 | Ahluwalia et al. | |
| 2006/0008907 A1 | 1/2006 | Friedman et al. | |
| 2006/0014191 A1 | 1/2006 | Lao et al. | |
| 2006/0014713 A1 | 1/2006 | Agrawal et al. | |
| 2006/0019916 A1 | 1/2006 | Krieg et al. | |
| 2006/0019917 A1 | 1/2006 | Guerciolini et al. | |
| 2006/0025363 A1 | 2/2006 | Breitenbach et al. | |
| 2006/0035344 A1 | 2/2006 | Pachuk et al. | |
| 2006/0083781 A1 | 4/2006 | Shastri et al. | |
| 2006/0105343 A1 | 5/2006 | Zetter et al. | |
| 2006/0159921 A1 | 7/2006 | Murthy et al. | |
| 2006/0183247 A1 | 8/2006 | Kim et al. | |
| 2006/0188560 A1 | 8/2006 | Cheresh et al. | |
| 2006/0233712 A1 | 10/2006 | Penades et al. | |
| 2006/0251623 A1 | 11/2006 | Bachmann et al. | |
| 2006/0252037 A1 | 11/2006 | Kolesnick et al. | |
| 2006/0275371 A1 | 12/2006 | Dai et al. | |
| 2006/0292174 A1 | 12/2006 | de los Rios et al. | |
| 2007/0066554 A1 | 3/2007 | Krieg et al. | |
| 2007/0093439 A1 | 4/2007 | Agrawal et al. | |
| 2007/0105139 A1 | 5/2007 | Nishigaki et al. | |
| 2007/0148251 A1 | 6/2007 | Hossainy et al. | |
| 2007/0184068 A1 | 8/2007 | Renner et al. | |
| 2007/0243196 A1 | 10/2007 | Bruck et al. | |
| 2008/0003232 A1 | 1/2008 | Wang et al. | |
| 2008/0057128 A1 | 3/2008 | Li et al. | |
| 2008/0097092 A1 | 4/2008 | Khvorova et al. | |
| 2008/0181928 A1 | 7/2008 | Hakimi-Mehr et al. | |
| 2008/0194463 A1 | 8/2008 | Weller et al. | |
| 2008/0206265 A1 | 8/2008 | Kandimalla et al. | |
| 2008/0213177 A1 | 9/2008 | Rademacher et al. | |
| 2008/0220072 A1 | 9/2008 | Unger et al. | |
| 2008/0274454 A1 | 11/2008 | Mirkin et al. | |
| 2008/0279785 A1 | 11/2008 | Kandimalla et al. | |
| 2008/0279946 A1 | 11/2008 | Hainfeld | |
| 2008/0292545 A1 | 11/2008 | Lin et al. | |
| 2008/0305106 A1 | 12/2008 | Brennan et al. | |
| 2008/0306016 A1 | 12/2008 | Mirkin et al. | |
| 2008/0311182 A1 | 12/2008 | Ferrari et al. | |
| 2008/0317749 A1 | 12/2008 | Kastelein et al. | |
| 2008/0317768 A1 | 12/2008 | Bianchi | |
| 2009/0018028 A1 | 1/2009 | Lindsay et al. | |
| 2009/0035576 A1 | 2/2009 | Prasad et al. | |
| 2009/0053169 A1 | 2/2009 | Castillo et al. | |
| 2009/0081244 A1 | 3/2009 | Glenn et al. | |
| 2009/0148384 A1 | 6/2009 | Fischer et al. | |
| 2009/0155173 A1 | 6/2009 | Scherman et al. | |
| 2009/0191188 A1 | 7/2009 | Krieg et al. | |
| 2009/0209629 A1 | 8/2009 | Mirkin et al. | |
| 2009/0286853 A1 | 11/2009 | Gryaznov et al. | |
| 2009/0317802 A1 | 12/2009 | Bhatia et al. | |
| 2009/0324706 A1 | 12/2009 | Mirkin et al. | |
| 2010/0003317 A1 | 1/2010 | Akinc et al. | |
| 2010/0136682 A1* | 6/2010 | Mirkin | C12N 15/111 435/325 |
| 2010/0144848 A1 | 6/2010 | Vogel et al. | |
| 2010/0166842 A1 | 7/2010 | Lu et al. | |
| 2010/0167051 A1 | 7/2010 | Goia et al. | |
| 2010/0183504 A1 | 7/2010 | Chen | |
| 2010/0183634 A1 | 7/2010 | Luo et al. | |
| 2010/0184844 A1 | 7/2010 | Mirkin et al. | |
| 2010/0203142 A1* | 8/2010 | Zhang | A61K 9/5123 424/487 |
| 2010/0233270 A1 | 9/2010 | Mirkin et al. | |
| 2010/0267814 A1 | 10/2010 | Bennett et al. | |
| 2011/0020242 A1 | 1/2011 | Zheng et al. | |
| 2011/0034422 A1 | 2/2011 | Kannan et al. | |
| 2011/0052697 A1 | 3/2011 | Farokhzad et al. | |
| 2011/0111974 A1 | 5/2011 | Mirkin et al. | |
| 2011/0135669 A1 | 6/2011 | Kandimalla et al. | |
| 2011/0158937 A1 | 6/2011 | Kandimalla et al. | |
| 2011/0172404 A1 | 7/2011 | Luo et al. | |
| 2011/0201672 A1 | 8/2011 | Krieg et al. | |
| 2011/0223257 A1 | 9/2011 | Zhao et al. | |
| 2011/0237435 A1 | 9/2011 | Ryan | |
| 2011/0244026 A1 | 10/2011 | Guild et al. | |
| 2011/0256224 A1 | 10/2011 | Sigalov | |
| 2011/0262347 A1 | 10/2011 | Ruoslahti et al. | |
| 2011/0262976 A1 | 10/2011 | Kandula et al. | |
| 2011/0293700 A1 | 12/2011 | Bratzler et al. | |
| 2011/0293701 A1 | 12/2011 | Bratzler et al. | |
| 2011/0293723 A1 | 12/2011 | Bratzler et al. | |
| 2011/0305684 A1 | 12/2011 | Agrawal et al. | |
| 2011/0305734 A1 | 12/2011 | Edelson et al. | |
| 2012/0093804 A1 | 4/2012 | Schroff et al. | |
| 2012/0107303 A1 | 5/2012 | Kandimalla et al. | |
| 2012/0244230 A1 | 9/2012 | Mirkin et al. | |
| 2012/0282186 A1 | 11/2012 | Mirkin et al. | |
| 2012/0301499 A1 | 11/2012 | Bachmann et al. | |
| 2013/0028857 A1 | 1/2013 | Gao et al. | |
| 2013/0034599 A1 | 2/2013 | Thaxton et al. | |
| 2013/0089614 A1 | 4/2013 | Zhang et al. | |
| 2013/0095039 A1 | 4/2013 | Lu et al. | |
| 2013/0123333 A1* | 5/2013 | Mirkin | A61K 9/5115 514/44 A |
| 2013/0178610 A1 | 7/2013 | Mirkin et al. | |
| 2013/0252852 A1 | 9/2013 | Pfeiffer et al. | |
| 2013/0287814 A1 | 10/2013 | Schroff et al. | |
| 2013/0295129 A1 | 11/2013 | Irvine et al. | |
| 2013/0315831 A1 | 11/2013 | Shi et al. | |
| 2014/0005258 A1 | 1/2014 | Mirkin et al. | |
| 2014/0010830 A1 | 1/2014 | Schroff et al. | |
| 2014/0199379 A1 | 7/2014 | Tartour et al. | |
| 2014/0227327 A1 | 8/2014 | Bencherif et al. | |
| 2014/0294927 A1 | 10/2014 | Thaxton et al. | |
| 2015/0104501 A1 | 4/2015 | Um et al. | |
| 2015/0118264 A1 | 4/2015 | Baumhof et al. | |

(56) References Cited

U.S. PATENT DOCUMENTS

| | | |
|---|---|---|
| 2016/0194642 A1 | 7/2016 | Gryaznov et al. |
| 2016/0310425 A1 | 10/2016 | Mirkin et al. |
| 2017/0044544 A1 | 2/2017 | Mirkin et al. |
| 2017/0232109 A1 | 2/2017 | Mirkin et al. |
| 2017/0130231 A1 | 5/2017 | Chae et al. |
| 2018/0000851 A1 | 1/2018 | Krieg |
| 2018/0043023 A1 | 2/2018 | Ilyinskii et al. |
| 2018/0161427 A1 | 6/2018 | Yu et al. |
| 2018/0169229 A1 | 6/2018 | Yu et al. |
| 2018/0171338 A1 | 6/2018 | Uhlmann et al. |
| 2018/0200381 A1 | 7/2018 | Kannan et al. |
| 2018/0264105 A1 | 9/2018 | Kugimiya et al. |
| 2018/0311176 A1 | 11/2018 | Ozsolak et al. |
| 2018/0312837 A1 | 11/2018 | Kortylewski et al. |
| 2019/0030185 A1 | 1/2019 | Mirkin et al. |
| 2019/0233825 A1 | 8/2019 | Ilg et al. |
| 2019/0275166 A1 | 9/2019 | Mirkin et al. |
| 2020/0022913 A1 | 1/2020 | Mirkin et al. |
| 2020/0069587 A1 | 3/2020 | Radovic-Moreno et al. |
| 2020/0101156 A1 | 4/2020 | Mirkin et al. |
| 2020/0291394 A1 | 9/2020 | Mirkin et al. |
| 2021/0052497 A1 | 2/2021 | Mirkin et al. |

FOREIGN PATENT DOCUMENTS

| | | |
|---|---|---|
| CN | 103212089 A | 7/2013 |
| EP | 1072679 A2 | 1/2001 |
| EP | 1674128 A1 | 6/2006 |
| EP | 1350262 B1 | 6/2008 |
| EP | 1991678 A2 | 11/2008 |
| EP | 2162117 A2 | 3/2010 |
| EP | 1408110 B1 | 6/2011 |
| EP | 2391718 A2 | 12/2011 |
| EP | 2399608 A1 | 12/2011 |
| EP | 1807094 B1 | 1/2012 |
| EP | 2759306 B1 | 4/2016 |
| EP | 1538904 B1 | 7/2016 |
| EP | 2 360 252 B1 | 2/2017 |
| EP | 3209778 B1 | 4/2019 |
| WO | WO-1989/002439 A1 | 3/1989 |
| WO | WO-1993/007883 A1 | 4/1993 |
| WO | WO 93/21528 A1 | 10/1993 |
| WO | WO-1993/021259 A1 | 10/1993 |
| WO | WO-1995/006731 A2 | 3/1995 |
| WO | WO-1995/011910 A1 | 5/1995 |
| WO | WO 95/034289 A1 | 12/1995 |
| WO | WO 1996/034876 A1 | 11/1996 |
| WO | WO-1997/012896 A1 | 4/1997 |
| WO | WO-1997/12896 A1 | 4/1997 |
| WO | WO 97/48715 A1 | 12/1997 |
| WO | WO-1998/04740 A1 | 2/1998 |
| WO | WO-1998/39352 A1 | 9/1998 |
| WO | WO-1998/039352 A1 | 9/1998 |
| WO | WO-1998/047343 A2 | 10/1998 |
| WO | WO-1999/011655 A1 | 3/1999 |
| WO | WO-1999/14226 A2 | 3/1999 |
| WO | WO-1999/014226 A2 | 3/1999 |
| WO | WO-2000/043045 A1 | 7/2000 |
| WO | WO-2001/000876 A1 | 1/2001 |
| WO | WO-2001/049869 | 7/2001 |
| WO | WO-2001/051665 A2 | 7/2001 |
| WO | WO-2001/73123 A2 | 10/2001 |
| WO | WO-2002/044321 A2 | 6/2002 |
| WO | WO-2002/096262 A2 | 12/2002 |
| WO | WO 2003/008539 A2 | 1/2003 |
| WO | WO-2003/008539 A2 | 1/2003 |
| WO | WO 03/030941 A1 | 4/2003 |
| WO | WO-2003/051278 A2 | 6/2003 |
| WO | WO 2004/047870 A1 | 6/2004 |
| WO | WO 2004/103301 A2 | 12/2004 |
| WO | WO-2005/008222 A2 | 1/2005 |
| WO | WO-2005/079462 A2 | 9/2005 |
| WO | WO-2005/116226 A2 | 12/2005 |
| WO | WO 2005/116226 A2 | 12/2005 |
| WO | WO-2006/012695 A1 | 2/2006 |
| WO | WO 2006/015872 A1 | 2/2006 |
| WO | WO-2006/045541 A1 | 5/2006 |
| WO | WO-2006/064451 A2 | 6/2006 |
| WO | WO-2006/064453 A2 | 6/2006 |
| WO | WO 2006/088833 A2 | 8/2006 |
| WO | WO-2006/138145 A1 | 12/2006 |
| WO | WO 2006/138145 A1 | 12/2006 |
| WO | WO 2007/008463 A2 | 1/2007 |
| WO | WO 2007/044851 A2 | 4/2007 |
| WO | WO-2007/047455 A2 | 4/2007 |
| WO | WO 2007/050059 A2 | 5/2007 |
| WO | WO 2007/055682 A2 | 5/2007 |
| WO | WO 2007/055704 A2 | 5/2007 |
| WO | WO 2007/064857 A2 | 6/2007 |
| WO | WO 2007/089607 A2 | 8/2007 |
| WO | WO 2007/096134 A1 | 8/2007 |
| WO | WO 2007/122405 A1 | 11/2007 |
| WO | WO 2008/014979 A2 | 2/2008 |
| WO | WO 2008/42156 A1 | 4/2008 |
| WO | WO-2008/097328 A2 | 8/2008 |
| WO | WO-2008/098248 A2 | 8/2008 |
| WO | WO 2008/127789 A2 | 10/2008 |
| WO | WO-2008/141289 A1 | 11/2008 |
| WO | WO 2008/151049 A2 | 12/2008 |
| WO | WO-2008/151049 A2 | 12/2008 |
| WO | WO 2009/012786 A2 | 1/2009 |
| WO | WO 2009/023819 A2 | 2/2009 |
| WO | WO 2009/026412 A1 | 2/2009 |
| WO | WO 2009/051451 A2 | 4/2009 |
| WO | WO 2009/061515 A1 | 5/2009 |
| WO | WO 2009/120887 A2 | 10/2009 |
| WO | WO-2010/060110 A1 | 5/2010 |
| WO | WO 2010/060110 A1 | 5/2010 |
| WO | WO-2010/081049 A1 | 7/2010 |
| WO | WO 2010/081049 A2 | 7/2010 |
| WO | WO-2010/120420 A1 | 10/2010 |
| WO | WO 2010/120420 A2 | 10/2010 |
| WO | WO 2011/017456 A2 | 2/2011 |
| WO | WO-2011/017690 A2 | 2/2011 |
| WO | WO 2011/037973 A1 | 3/2011 |
| WO | WO 2011/053940 A2 | 5/2011 |
| WO | WO-2011/079290 | 6/2011 |
| WO | WO 2011/079290 A1 | 6/2011 |
| WO | WO 2011/091065 A2 | 7/2011 |
| WO | WO 2011/113054 A2 | 9/2011 |
| WO | WO 2011/143608 A1 | 11/2011 |
| WO | WO 2013/012628 A2 | 1/2013 |
| WO | WO 2013/177419 A1 | 11/2013 |
| WO | WO 2014/025795 A1 | 2/2014 |
| WO | WO 2014/123935 A1 | 8/2014 |
| WO | WO 2014/133547 A1 | 9/2014 |
| WO | WO 2013/049941 A | 10/2014 |
| WO | WO 2014/175836 A1 | 10/2014 |
| WO | WO-2015/126502 A2 | 8/2015 |
| WO | WO 2015/153975 A1 | 10/2015 |
| WO | WO 2017/035278 A1 | 3/2017 |
| WO | WO 2017/42336 A1 | 3/2017 |
| WO | WO 2017/050806 A1 | 3/2017 |
| WO | WO 2018/039629 A2 | 3/2018 |
| WO | WO 2018/152327 A2 | 8/2018 |
| WO | WO 2019/118883 A2 | 6/2019 |

OTHER PUBLICATIONS

Abou-Alfa et al., Randomized phase III study of exatecan and gemcitabine compared with gemcitabine alone in untreated advanced pancreatic cancer, J. Clin. Oncol., 24(27):4441-7 (2006).

Agasti et al., Photoregulated release of caged anticancer drugs from gold nanoparticles, J. Am. Chem. Soc., 131(16):5728-9 (2009).

Agrawal et al., Antisence therapeutics: Is it as simple as complementary base recognition? Mol. Med. Today, 6: 72-81 (2000).

Aime et al., Insights into the use of paramagnetic Gd(III) complexes in MR-molecular imaging investigations, J. Magn. Reson. Imaging, 16(4):394-406 (2002).

Aime et al., Pushing the sensitivity envelope of lanthanide-based magnetic resonance imaging (MRI) contrast agents for molecular imaging applications, Acc. Chem. Res., 42(7):822-31 (2009).

(56) References Cited

OTHER PUBLICATIONS

Alivisatos et al., Organization of 'nanocrystal molecules' using DNA. Nature, 382: 609-11 (1996).
Alivisatos, The use of nanocrystals in biological detection, Nat. Biotechnol., 22(1):47-52 (2004).
Allara et al., Spontaneously organized molecular assemblies. 1. Formation, dynamics, and physical properties of n-Alkanoic acids adsorbed from solution on an oxidized aluminum surface, Langmuir, 1:45-52 (1985).
Allara et al., The study of the gas-solid interaction of acetic acid with a cuprous oxide surface using reflection-absorption spectroscopy, J. Colloid Interface Sci., 49:410-21 (1974).
Alric et al., Gadolinium chelate coated gold nanoparticles as contrast agents for both X-ray computed tomography and magnetic resonance imaging, J. Am. Chem. Soc., 130(18):5908-15 (2008).
Altieri, Survivin, versatile modulation of cell division and apoptosis in cancer, Oncogene, 22: 8581-9 (2003).
Altschul et al., Basic local alignment search tool, J. Mol. Biol., 215(3):403-10 (1990).
Amirkhanov et al., Design of (Gd-D03A)n-polydiamidopropanoyl-peptide nucleic acid-D(Cys-Ser-Lys-Cys) magnetic resonance contrast agents, Biopolymers, 89(12):1061-76 (2008).
Angelini et al., Reversal of P-glycoprotein-mediated multidrug resistance in human sarcoma MES-SA/Dx-5 cells by nonsteroidal anti-inflammatory drugs, Oncol. Rep., 20(4):731-5 (2008).
Anton et al., Design and production of nanoparticles formulated from nano-emulsion templates—a review, J. Control Release, 128(3):185-99 (2008).
Aynie, et al., Spongelike alginate nanoparticles as a new potential system for the delivery of antisense oligonucleotides. Antisense Nucl. Acid Drug Dev., 9: 301-12 (1999).
Bahnemann, Photochemical Conversion and Storage of Solar Energy, Pelizetti and Schiavello (Eds.) pp. 251-276 (1991).
Baker et al., Dendrimer-mediated cell transfection in vitro. Meth. Molec. Biol., 245: 67-81 (2004).
Balasubramanian et al., Biodistribution of gold nanoparticles and gene expression changes in the liver and spleen after intravenous administration in rats, Biomaterials, 31(8):2034-42 (2010).
Bardeesy et al., Pancreatic cancer biology and genetics, Nat. Rev. Cancer, 2(12):897-909 (2002).
Bath et al., DNA nanomachines, Nat. Nanotechnol., 2: 275-84 (2007).
Baudhuim, Photochemical conversion and storage of solar energy. Kluwer Academic Publishers. 251-76 (1990).
Baudhuin et al., Molecular interactions between colloidal gold, proteins, and living cells. Chapter 1: 1-17 (1989).
Berton, et al., Highly loaded nanoparticulate carrier using an hydrophobic antisense oligonucleotide complex, Eur. J. Pharma. Sci., 9: 163-70 (1999).
Besch et al., Characterization and quantification of triple helix formation in chromosomal DNA. J. Mol. Biol., 341: 979-89 (2004).
Bharali et al., Organically modified silica nanoparticles: a nonviral vector for in vivo gene delivery and expression in the brain. Proc. Natl. Acad. Sci. USA, 102(32): 11539-44 (2005).
Biancone et al., Magnetic resonance imaging of gadolinium-labeled pancreatic islets for experimental transplantation, NMR Biomed., 20(1):40-8 (2007).
Bielinska et al., DNA complexing with polyamidoamine dendrimers: implications for transfection. Bioconjug Chem., 10(5): 843-50 (1999).
Birck et al., Mutation and allelic loss of the PTEN/MMAC1 gene in primary and metastatic melanoma biopsies, J. Invest. Dermatol., 114: 277-80 (2000).
Bisht et al., Polymeric nanoparticle-encapsulated curcumin ("nanocurcumin"): a novel strategy for human cancer therapy, J. Nanobiotechnology, 5:3 (2007) (18 pages).
Bowman et al., Inhibition of HIV fusion with multivalent gold nanoparticles, J. Am. Chem. Soc., 130(22):6896-7 (2008).
Bramhill, Bacterial cell division, Annu. Rev. Cell Dev. Biol., 13: 395-424 (1997).

Bratu et al., Visualizing the distribution and transport of mRNAs in living cells, Proc. Natl. Acad. Sci. USA, 100: 13308-13 (2003).
Brown et al., Surface treatment of the hydrophobic drug danazol to improve drug dissolution, Int. J. Pharmaceutics, 165:227-37 (1998).
Burwell, Modified silica gels as adsorbents and catalysts, Chem. Tech., 4:370-7 (1974).
Cao et al., Raman dye-labeled nanoparticle probes for proteins, J. Am. Chem. Soc., 125(48):14676-7 (2003).
Capaccioli et al., Cationic lipids improve antisense oligonucleotide uptake and prevent degradation in cultured cells and inhuman serum, Biochem. Biophys. Res. Commun., 197(2): 818-25 (1993).
Caravan et al., The interaction of MS-325 with human serum albumin and its effect on proton relaxation rates, J. Am. Chem. Soc., 124(12):3152-62 (2002).
Caravan, Strategies for increasing the sensitivity of gadolinium based MRI contrast agents, Chem. Soc. Rev., 35(6):512-23 (2006).
Castoldi et al., A sensitive array for microRNA expression profiling (miChip) based on locked nucleic acids (LNA), RNA. 12: 913-20 (2006).
Cha et al., Hepatocellular carcinoma: current management, Curr. Probl. Surg., 47(1):10-67 (2010).
Chari et al., Immunoconjugates containing novel maytansinoids: promising anticancer drugs, Cancer Res., 52(1):127-31 (1992).
Charreyre et al., Fluorescence energy transfer study of the conformation of oligonucleotides covalently bound to polystyrene latex particles. Langmuir, 13: 3103-10 (1997).
Chavany et al., Polyalkylcyanoacrylate nanoparticles as polymeric carriers for antisense oligonucleotides, Pharma. Res., 9(4): 441-9 (1992).
Chavany, et al., Adsorption of oligonucleotides onto polyisohexylcyanoacrylate nanoparticles protects them against nucleases and increases their cellular uptake. Pharma. Res., 11(9): 1370-8 (1994).
Chen et al., Kinetics and thermodynamics of DNA hybridization on gold nanoparticles, Nucl. Acids Res., 37: 3756-65 (2009).
Chen et al., MDR 1 activation is the predominant resistance mechanism selected by vinblastine in MES-SA cells, Br. J. Cancer, 83(7):892-8 (2000).
Cheng et al., Tandem synthesis of core-shell brush copolymers and their transformation to peripherally cross-linked and hollowed nanostructures, J. Am. Chem. Soc., 128(21):6808-9 (2006).
Cheung et al., Akt3 and mutant V600E B-Raf cooperate to promote early melanoma development, Cancer Res., 68:3429-39 (2008).
Chirila et al., The use of synthetic polymers for delivery of therapeutic antisense oligodeoxynucleotides. Biomaterials, 23: 321-42 (2002).
Chithrani et al., Determining the size and shape dependence of gold nanoparticle uptake into mammalian cells, Nano Lett., 6(4):662-8 (2006).
Chithrani et al., Elucidating the mechanism of cellular uptake and removal of protein-coated gold nanoparticles of different sizes and shapes. Nano Lett., 7: 1542-50 (2007).
Chompoosor et al., Charge dependence of ligand release and monolayer stability of gold nanoparticles by biogenic thiols, Bioconjugate Chem., 19:1342-5 (2008).
Chrisey et al., Covalent attachment of synthetic DNA to self-assembled monolayer films, Nucl. Acids Res., 24:3031-9 (1996).
Chu et al., Effects of photoactivated 5-aminolevulinic acid hexyl ester on MDR1 over-expressing human uterine sarcoma cells, Toxicol. Lett., 181(1):7-12 (2008).
Cload et al., Polyether tethered oligonucleotide probes. J. Am. Chem. Soc., 113(16): 6324-6 (1991).
Connor et al., Gold nanoparticles are taken up by human cells but do not cause acute cytotoxicity, Small, 1(3):325-7 (2005).
Crawford et al., A novel B-RAF inhibitor blocks interleukin-8 (IL-8) synthesis in human melanoma xenografts, revealing IL-8 as a potential pharmacodynamic biomarker, *Mol. Cancer Ther.*, 7:492-9 (2008).
Crich et al., Improved route for the visualization of stem cells labeled with a Gd-/Eu-chelate as dual (MRI and fluorescence) agent, Magn. Reson. Med., 51(5):938-44 (2004).
Crooke et al., Progress in antisense technology. Ann. Rev. Med., 55: 61-95 (2004).

(56) References Cited

OTHER PUBLICATIONS

Daniel et al., Gold nanoparticles: assembly, supramolecular chemistry, quantum-size-related properties, and applications toward biology, catalysis, and nanotechnology. Chem Rev., 104(1): 293-346 (2004).
Dankort et al., A new mouse model to explore the initiation, progression, and therapy of BRAFV600E-induced lung tumors, Genes Dev., 21: 379-84 (2007).
Dankort et al., Braf(V600E) cooperates with Pten loss to induce metastatic melanoma, Nat Genet., 41: 544-52 (2009).
Davies et al., A novel AKT3 mutation in melanoma tumours and cell lines, Br. J. Cancer, 99: 1265-8 (2008).
Demers et al., Combinatorial templates generated by dip-pen nanolithography for the formation of two-dimensional particle arrays, Angew. Chem. Int. Ed., 40: 3071-3 (2003).
DeMesmaeker et al., Antisense oligonucleotides. Acc. Chem. Res., 28(9): 366-74 (1995).
DeMesmaeker et al., Backbone modifications in oligonucleotides and peptide nucleic acid systems, Curr. Opin. Struct. Biol., 5:343-55 (1995).
Deutsch et al., Synthesis of congeners and prodrugs. 3. Water-soluble prodrugs of taxol with potent antitumor activity, J. Med. Chem., 32(4):788-92 (1989).
Devlin et al., Random peptide libraries: a source of specific protein binding molecules, Science, 249: 404-6 (1990).
Dhar et al., Polyvalent oligonucleotide gold nanoparticle conjugates as delivery vehicles for platinum(IV) warheads. *J. Am. Chem. Soc.*, 131(41): 14652-3 (2009).
Dhar et al., Targeted single wall carbon nanotube mediated Pt(IV) prodrug delivery using folate as a homing device. *J. Am. Chem. Soc.*, 130(34): 11467-76 (2008).
Dhomen et al., BRAF signaling and targeted therapies in melanoma, Hematol. Oncol. Clin. North Am., 23: 529-45, ix (2009).
Donachie, The cell cycle of *Escherichia coli.*, *Annu. Rev. Microbiol.*, 47: 199-230 (1993).
Dreyfus et al., Simple quantitative model for the reversible associate of DNA coated colloids, Phys. Rev. Lett., 102: 048301 (2009).
Dubertret et al., Single-mismatch detection using gold-quenched fluorescent oligonucleotides, Nat. Biotechnol., 19: 365-70 (2001).
Duimstra et al., A gadolinium chelate for detection of beta-glucuronidase: a self-immolative approach, J. Am. Chem. Soc., 127(37):12847-55 (2005).
Dulkeith et al., Gold nanoparticles quench fluorescence by phase induced radiative rate suppression, Nano Lett., 5: 585-9 (2005).
Durand et al., Circular dichroism studies of an oligodeoxyribonucleotide containing a hairpin loop made of a hexaethylene glycol chain: conformation and stability. Nucl. Acids Res. , 18(21): 6353-9 (1990).
Dykxhoorn et al., Killing the messenger: short RNAs that silence gene expression, Nat. Rev. Mol. Cell Biol., 4(6):457-67 (2003).
Elaissari et al., Effect of charge nature on the adsorption of single-stranded DNA fragments onto latex particles. J. Colloid Interface Sci., 202: 251-60 (1998).
Elghanian et al., Selective colorimetric detection of polynucleotides based on the distance-dependent optical properties of gold nanoparticles, Science, 277(5329):1078-81 (1997).
Eltekova et al., Adsorption of aromatic compounds from solutions in titanium dioxide and silica, Langmuir, 3:951-7 (1987).
Endres et al., DNA-TIO2 nanoconjugates labeled with magnetic resonance contrast agents, J. Am. Chem. Soc., 129(51):15760-1 and supplementary information (2007).
Examination Report from European Application No. 08729548.1, dated Jan. 19, 2010.
Fahy et al., Design and synthesis of polyacrylamide-based oligonucleotide supports for use in nucleic acid diagnostics, Nucl. Acids Res., 21: 1819-26 (1993).
Faulds et al., Evaluation of surface-enhanced resonance Raman scattering for quantitative DNA analysis. Anal. Chem., 76: 412-7 (2004).
Femino et al., Visualization of single RNA transcripts in situ. Science, 280: 585-90 (1998).
Ferentz et al., Disulfide-crosslinked oligonucleotides. J. Am. Chem. Soc., 113(10): 4000-2 (1991).
Final Office Action issued in connection with U.S. Appl. No. 11/917,680, dated Nov. 10, 2010.
Final Office Action issued in connection with U.S. Appl. No. 11/917,680, dated Nov. 10, 2011.
Final Office Action issued in connection with U.S. Appl. No. 12/130,643, dated Jun. 16, 2011.
Flandroy et al., (D, L)Polyactide microspheres as embolic agent. *Neuroradiology*, 32: 311-5 (1990).
Frens, Controlled nucleation for the regulation of the particle size in monodisperse gold suspensions. *Nat. Phys. Sci.*, 241: 20-2 (1973).
Frens, Particle size and sol stability in metal colloids, Kolloid-Zeitschrift und Zeitschrift fur Polymere, 250(7):736-41 (1972).
Frullano et al., Multimodal MRI contrast agents, J. Biol. Inorg. Chem., 12(7):939-40 (2007).
Fukuda et al., Effective transformation of unactivated alkynes into ketones or acetals by means of Au(III) catalyst, J. Org. Chem., 56(11):3729-31 (1991).
Fukuda et al., Efficient transformation of methyl propargyl ethers into alpha,beta-unsaturated ketones, Bull. Chem. Soc. Jpn., 64:2013-5 (1991).
Furstner et al., Catalytic carbophilic activation: catalysis by platinum and gold pi acids, Angew Chem Int Ed Engl., 46(19):3410-49 (2007).
Gao et al., Secondary structure effects on DNA hybridization kinetics: a solution versus surface comparison. Nucl. Acids Res., 34: 3370-7 (2006).
Gavriel et al., Identification of programmed cell death in situ via specific labeling of nuclear DNA fragmentation, J. Cell Biol., 119(3):493-501 (1992).
Gerdes et al., Experimental determination and system level analysis of essential genes in *Escherichia coli* MG1655. *J. Bacteriol.*, 185: 5673-84 (2003).
Gestwicki et al., Influencing receptor-ligand binding mechanisms with multivalent ligand architecture. J. Am. Chem. Soc., 124: 14922-33 (2002).
Ghosh et al., Gold nanoparticles in delivery applications, Adv. Drug Deliv. Rev. 60(11):1307-15 (2008).
Gibson et al., Paclitaxel-functionalized gold nanoparticles, J. Am. Chem. Soc., 129(37):11653-61 (2007).
Gidwani et al., Hybridization kinetics of double-stranded DNA probes for rapid molecular analysis. Analyst, 134: 1675-81 (2009).
Giljohann et al., Gold nanoparticles for biology and medicine, Angew Chem. Int. Ed. Engl., 49(19):3280-94 (2010).
Goel et al., Melanocytic nevus-like hyperplasia and melanoma in transgenic BRAFV600E mice. Oncogene, 28: 2289-98 (2009).
Goodrich et al., Non-coding-RNA regulators of RNA polymerase II transcription, Nat. Rev. Mol. Cell Biol., 7(8):612-6 (2006).
Grabar et al., Preparation and characterization of Au colloid monolayers, Anal. Chem., 67:735-43 (1995).
Guo et al., CELL-SELEX: Novel perspectives of aptamer-based therapeutics, Int. J. Mol. Sci., 9: 668-78 (2008).
Hale et al., Recruitment of ZipA to the septal ring of *Escherichia coli* is dependent on FtsZ and independent of FtsA. *J. Bacteriol.*, 181: 167-76 (1999).
Hamilton et al., A species of small antisense RNA in post-transcriptional gene silencing in plants. Science, 286: 950-2 (1999).
Hammond et al., An RNA-directed nuclease mediates post-transcriptional gene silencing in *Drosophilia* cells. Nature, 404: 293-6 (2000).
Han et al., A gold nanoparticle based approach for screening triplex DNA binders, J. Am. Chem. Soc., 128(15):4954-5 (2006).
Hashmi et al., Gold catalysis, Angew Chem Int Ed Engl., 45(47):7896-936 (2006).
Hashmi et al., Gold-catalyzed organic reactions, Chem. Rev., 107:3180-211 (2007).
Hayashi, Ultrafine particles, Physics Today, pp. 44-60 (Dec. 1987).
Hayashi, Ultrafine particles, Vac. Sci. Technol. A, 5(4):1375-84 (1987).

(56) References Cited

OTHER PUBLICATIONS

Hayat, (Ed.) Colloidal Gold: Principles, Methods, and Applications, vol. 1, Table of Contents, pp. v-xvii; vol. 2, Table of Contents pp. v-xix; vol. 3, Table of Contents, pp. v-xiv, Academic Press, San Diego (1989-1991).
He et al., Colloidal Au-enhanced surface plasmon resonance for ultrasensitive detection of DNA hybridization. J. Am. Chem. Soc., 122(38): 9071-7 (2000).
Hegner et al., Modified DNA immobilized on bioreactive self-assembled monolayer on gold for dynamic force microscopy imaging in aqueous buffer solution, J. Vac. Sci. Technol. B, 14(2):1418-21 (1996).
Hickman et al., Combining spontaneous molecular assembly with microfabrication to pattern surfaces: selective binding of isonitriles to platinum microwires and characterization by electrochemistry and surface spectroscopy, J. Am. Chem. Soc., 111:7271-2 (1989).
Holen et al., Positional effects of short interfering RNAs targeting the human coagulation trigger tissue factor. *Nucl. Acids Res.*, 30: 1757-66 (2002).
Hu et al., Advances in high-field magnetic resonance imaging, Annu. Rev. Biomed.Eng., 6:157-84 (2004).
Hu et al., Hollow chitosan/poly(acrylic acid) nanospheres as drug carriers, Biomacromolecules, 8(4):1069-76 (2007).
Hubbard, Electrochemistry of well-defined sufaces, Acc. Chem. Res., 13:177-84 (1980).
Hurst et al., "Multisegmented one-dimensional nanorods prepared by hard-template synthetic methods," Angew. Chem. Int. Ed. Engl., 45:2672-2692 (2006).
Hussain et al., A novel anionic dendrimer for improved cellular delivery of antisense oligonucleotides. J. Controlled Rel., 99: 139-55 (2004).
Hwu et al., Targeted Paclitaxel by conjugation to iron oxide and gold nanoparticles, J. Am. Chem. Soc., 131(1):66-8 (2009).
Iler, The surface chemistry of silica (chapter 6), In: Iler, Chemistry of Silica, New York: John Wiley & Sons (1979).
International Preliminary Report on Patentability for corresponding international application No. PCT/US2010/047594, dated Mar. 6, 2012.
International Preliminary Report on Patentability for International Application No. PCT/US10/62047, dated Jun. 26, 2012.
International Preliminary Report on Patentability for International Application No. PCT/US2006/022325, dated Dec. 17, 2007.
International Preliminary Report on Patentability for International Application No. PCT/US2008/053603, dated Aug. 11, 2009.
International Preliminary Report on Patentability for International Application No. PCT/US2008/065366, dated Dec. 1, 2009.
International Preliminary Report on Patentability for International application No. PCT/US2009/065822, dated May 24, 2011.
International Preliminary Report on Patentability for International Application No. PCT/US2010/020558, dated Jul. 12, 2011.
International Preliminary Report on Patentability for International Application No. PCT/US2010/044453, dated Feb. 7, 2012.
International Preliminary Report on Patentability for International Application No. PCT/US2010/044844, dated Feb. 7, 2012.
International Preliminary Report on Patentability for International Application No. PCT/US2010/55018, dated May 1, 2012.
International Preliminary Reporton Patentability, PCT/US2010/27363, dated Oct. 18, 2011.
International Preliminary Reporton Patentability, PCT/US2010/47591, dated Mar. 6, 2012.
International Preliminary Reporton Patentability, PCT/US2010/47594, dated Mar. 6, 2012.
International Search Report and Written Opinion for corresponding international application No. PCT/US10/47594, dated Oct. 20, 2010.
International Search Report and Written Opinion for International Application No. PCT/US10/62047, dated May 6, 2011.
International Search Report and Written Opinion for International Application No. PCT/US2006/022325, dated Oct. 20, 2006.
International Search Report and Written Opinion for International Application No. PCT/US2008/053603, dated Jul. 30, 2008.
International Search Report and Written Opinion for International Application No. PCT/US2008/065366, dated Aug. 28, 2008.
International Search Report and Written Opinion for International application No. PCT/US2008/065822, dated Mar. 5, 2010.
International Search Report and Written Opinion for International Application No. PCT/US2010/020558, dated Mar. 9, 2010.
International Search Report and Written Opinion for International Application No. PCT/US2010/044453, dated Apr. 29, 2011.
International Search Report and Written Opinion for International Application No. PCT/US2010/044844, dated Apr. 27, 2011.
International Search Report and Written Opinion for International Application No. PCT/US2010/27363, dated Apr. 15, 2010.
International Search Report and Written Opinion for International Application No. PCT/US2010/47591, dated Oct. 4, 2010.
International Search Report and Written Opinion for International Application No. PCT/US2010/47594, dated Oct. 8, 2010.
International Search Report and Written Opinion for International Application No. PCT/US2010/55018, dated Dec. 9, 2010.
Jackson et al., *Escherichia coli* O157:H7 diarrhea associated with well water and infected cattle on an Ontario farm, Epidemiol. Infect., 120:17-20 (1998).
Jackson et al., How do microRNAs regulate gene expression?, Sci STKE, 2007(367):re1 (2007).
Jaschke et al., Automated incorporation of polyethylene glycol in synthetic oligonucleotides. Tetrahedron Lett., 34: 301-4 (1993).
Jason et al., Toxicology of antisense therapeutics. Toxicol. Appl. Pharmacol., 201(1): 66-83 (2004).
Jen et al., A nonviral transfection approach in vitro: the design of a gold nanoparticle vector joint with microelectromechanical systems. Langmuir, 20(4): 1369-74 (2004).
Jeong et al., Novel intracellular delivery system of antisense oligonucleotide by self-assembled hybrid micelles composed of DNA/PEG conjugate and cationic fusogenic peptide. Bioconjugate Chem., 14: 473-9 (2003).
Jin et al., Radiosensitization of paclitaxel, etanidazole and paclitaxel+etanidazole nanoparticles on hypoxic human tumor cells in vitro, Biomaterials, 28(25):3724-30 (2007).
Jin et al., What controls the melting properties of DNA-linked gold nanoparticle assemblies? J. Am. Chem. Soc., 125: 1643 (2003).
Kalman et al., Potentiometric and relaxometric properties of a gadolinium-based MRI contrast agent for sensing tissue pH, Inorg. Chem., 46(13):5260-70 (2007).
Kan et al., Distribution and effect of iodized poppyseed oil in the liver after hepatic artery embolization: experimental study in several animal species, Radiology, 186(3):861-6 (1993).
Kan et al., Role of Kupffer cells in iodized oil embolization, Invest. Radiol., 29(11):990-3 (1994).
Kasuya et al., Chapter 8—Bio-nanocapsule-liposome conjugates for in vivo pinpoint drug and gene delivery, Methods Enzymol., 464:147-66 (2009).
Katz et al., Integrated nanoparticle-biomolecule hybrid systems: synthesis, properties, and applications, Angew. Chem. Int. Ed., 43: 6042-108 (2004).
Kim et al., Biodegradable quantum dot nanocomposites enable live cell labeling and imaging of cytoplasmic targets, Nano Lett., 8(11):3887-92 (2008).
Kim et al., Direct synthesis of polymer nanocapsules with a noncovalently tailorable surface, Angew. Chem. Int. Ed. Engl., 46(19):3471-4 (2007).
Kim et al., Direct synthesis of polymer nanocapsules: self-assembly of polymer hollow spheres through irreversible covalent bond formation, J. Am. Chem. Soc., 132(28):9908-19 (2010).
Kim et al., Facile, template-free synthesis of stimuli-responsive polymer nanocapsules for targeted drug delivery, Angew. Chem. Int. Ed. Engl., 49(26):4405-8 (2010).
Kloosterman et al., In situ detection of miRNAs in animal embryos using LNA-modified oligonucleotide probes, Nat. Methods, 3: 27-9 (2006).
Kolarova et al., Preparation of magnetic oligo (dT) particles, Biotechniques, 20: 196-8 (1996).

(56) References Cited

OTHER PUBLICATIONS

Kondo et al., Nanotube formation through the continuous one-dimensional fusion of hollow nanocapsules composed of layer-by-layer poly(lactic acid) stereocomplex films, J. Am. Chem. Soc., 132(24):8236-7 (2010).
Kopylov et al., Combinatorial chemistry of nucleic acids: SELEX, Mol. Biol., 34: 940-54 (2000).
Kroschwitz (ed.), The Concise Encyclopedia of Polymer Science and Engineering, pp. 858-859, New York: John Wiley & Sons (1990).
Krutzfeldt et al., Silencing of microRNAs in vivo with 'antagomirs', Nature, 438(7068):685-9 (2005).
Landfester et al., From polymeric particles to multifunctional nanocapsules for biomedical applications using the miniemulsion process, J. Polymer Sci. Part A, 48(3):493-515 (2010).
Lannutti et al., Human angiostatin inhibits murine hemangioendothelioma tumor growth in vivo, Cancer Res., 57: 5277-80 (1997).
Lebedeva et al., Antisense oligonucleotides: Promise and reality. Annu. Rev. Pharmacol. Toxicol., 41: 403-19 (2001).
Lee et al., "A DNA-Gold Nanoparticle-Based Colormetric Competition Assay for the Detection of Cysteine," Nano Letter, 8(2):529-533 (2008).
Lee et al., Adsorption of ordered zirconium phosphonate multilayer films on silicon and gold surfaces, J. Phys. Chem., 92:2597-601 (1988).
Lee et al., Chip-based scanometric detection of mercuric ion using DNA-functionalized gold nanoparticles, Anal. Chem., 80(17):6805-8 (2008).
Lee et al., Colorimetric detection of mercuric ion (Hg2+) in aqueous media using DNA-functionalized gold nanoparticles, Angew. Chem. Int. Ed. Engl., 46(22):4093-6 (2007).
Lemaigre et al., Transcriptional control of genes that regulate glycolysis and gluconeogenesis in adult liver, Biochem. J., 303: 1-14 (1994).
Leslie et al., A new tool for oligonucleotides import into cells. Clin. Chem., 55: 609-10 (2009).
Leunissen et al., Switchable self-protected attractions in DNA-functionalized colloids. Nat. Mater., 8: 590-95 (2009).
Lewis, "Controlled release of bioactive agents from lactide/glycolide polymer", pp. 1-41, IN: Chasin et al. (eds.), Biodegradable Polymers as Drug Delivery Systems, Marcel Dekker (1990).
Li et al., Dual-reactive surfactant used for synthesis of functional nanocapsules in miniemulsion, J. Am. Chem. Soc., 132(23):7823-5 (2010).
Li et al., Gold-catalyzed organic transformations, Chem. Rev., 108(8):3239-65 (2008).
Li et al., Reversible and chemically programmable micelle assembly with DNA block-copolymer amiphiphiles, Nano Lett., 4(6):1055-8 (2004).
Lin et al., Effector/memory but not naive regulatory T cells are responsible for the loss of concomitant tumor immunity. J. Immunol., 182: 6095-104 (2009).
Lin et al., Modeling genomic diversity and tumor dependency in malignant melanoma. Cancer Res., 68: 664-73 (2003).
Link et al., Size and Temperature Dependence of the Plasmon Absorption of Colloidal Gold Nanoparticles, J. Phys. Chem. B, 103(21):4212-7 (1999).
Lipshutz et al., High density synthetic oligonucleotide arrays. Nanotechnology, 14: R15-27 (2003).
Liu et al., Accelerated color change of gold nanoparticles assembled by DNAzymes for simple and fast colorimetric Pb2+ detection. J. Am. Chem. Soc., 126: 12298-305 (2004).
Liu et al., ARDB—Antibiotic Resistance Genes Database. *Nucl. Acids Res.*, 37: D443-7 (2009).
Liu et al., Argonaute2 is the catalytic engine of mammalian RNAi. Science, 305(5689): 1437-41 (2004).
Liu et al., Cross-linked polynorbornene-coated gold nanoparticles: dependence of particle stability on cross-linking position and cross-linker structure, Langmuir, 24:11169-74 (2008).

Liu et al., De-N-acetyl GM3 promotes melanoma cell migration and invasion through urokinase plasminogen activator receptor signaling-dependent MMP-2 activation. Cancer Res., 69: 8662-9 (2009).
Liu et al., DNA-based micelles: synthesis, micellar properties and size-dependent cell permeability, Chemistry, 16(12):3791-7 (2010).
Liu et al., New poly(d-glucaramidoamine)s induce DNA nanoparticle formation and efficient gene delivery into mammalian cells. J. Am. Chem. Soc., 126: 7422-3 (2004).
Liu et al., Rational design of "turn-on" allosteric DNAzyme catalytic beacons for aqueous mercury ions with ultrahigh sensitivity and selectivity, Angew. Chem. Int. Ed. Engl., 46(60):7587-90 (2007).
Liu et al., Synthesis, stability, and cellular internalization of gold nanoparticles containing mixed peptide-poly(ethylene glycol) monolayers. Anal. Chem., 79: 2221-9 (2007).
Llovet et al., Arterial embolisation or chemoembolisation versus symptomatic treatment in patients with unresectable hepatocellular carcinoma: a randomised controlled trial, Lancet, 359(9319):1734-9 (2002).
Loeken, Effects of mutation of the CREB binding site of the somatostatin promoter on cyclic AMP responsiveness in CV-1 cells. Gene Expr., 3: 253-64 (1993).
Love et al., Self-assembled monolayers of thiolates on metals as a form of nanotechnology. Chem. Rev., 105: 1103-69 (2005).
Lutkenhaus et al., Bacterial cell division and the Z ring. Annu. Rev. Biochem., 66: 93-116 (1997).
Lytton-Jean et al., A thermodynamic investigation into the binding properties of DNA functionalized gold nanoparticle probes and molecular fluorophore probes. J. Am. Chem Soc., 127: 12754-5 (2005).
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res., 21: 2585-9 (1993).
Ma et al., Design and synthesis of RNA miniduplexes via a synthetic linker approach. Biochemistry, 32(7): 1751-8 (1993).
Major et al., Bioresponsive, cell-penetrating, and multimeric MR contrast agents, Acc. Chem. Res., 42(7):893-903 (2009).
Major et al., The synthesis and in vitro testing of a zinc-activated MRI contrast agent, Proc. Natl. Acad. Sci. USA, 104(35):13881-6 (2007).
Maoz et al., Penetration-controlled reactions in organized monolayer assemblies. 1. Aqueous permanganate interaction with monolayer and multilayer films of long-chain surfactants, Langmuir, 3:1034-44 (1987).
Maoz et al., Penetration-controlled reactions in organized monolayer assemblies. 2. Aqueous permanganate interaction with self-assembling monolayers of long-chain surfactants, Langmuir, 3:1045-51 (1987).
Martinez et al., Locked nucleic acid based beacons for surface interaction studies and biosensor development. Anal. Chem., 81: 3448-54 (2009).
Maruyama, et al., Nanoparticle DNA carrier with poly(L-lysine) grafted polysaccharide copolymer and poly(D,L-lactic acid). Bioconjugate Chem., 8: 735-742 (1997).
Massart, Preparation of aqueous magnetic liquids in alkaline and acidic media. IEEE Transactions on Magnetics. 17(2): 1247-8 (1981).
Matsuura et al., Construction and characterization of protein libraries composed of secondary structure modules. Protein Sci., 11: 2631-43 (2002).
Matteucci et al., Synthesis of deoxyoligonucleotides on a polymer support, J. Am. Chem. Soc., 103:3185-3191 (1981).
Mattson et al., A practical approach to crosslinking. Molec. Biol. Rep., 17: 167-83 (1993).
Maxwell et al., Self-assembled nanoparticle probes for recognition and detection of biomolecules. J. Am. Chem. Soc., 124: 9606-12 (2002).
Maye et al., A simple method for kinetic control of DNA-induced nanoparticle assembly. J. Am. Chem. Soc., 128: 14020-1 (2006).
McCurdy et al., Deoxyligonucleotides with inverted polarity: Synthesis and use in triple-helix formation. Nucleosides & Nucleotides, 10:287-90 (1991).

(56) References Cited

OTHER PUBLICATIONS

McGehee et al., Differentiation-specific element: a cis-acting developmental switch required for the sustained transcriptional expression of the angiotensinogen gene during hormonal-induced differentiation of 3T3-L1 fibroblasts to adipocytes. Mol. Endocrinol., 7: 551-60 (1993).
McKenzie et al., Sequence-specific DNA detection using high-affinity LNA-functionalized gold nanoparticles. Small, 3(11): 1866-8 (2007).
McManus et al., Gene silencing in mammals by small interfering RNAs. Nat. Rev. Genet., 3(10): 737-47 (2002).
Mendell, MicroRNAs: critical regulators of development, cellular physiology and malignancy, Cell Cycle, 4(9):1179-84 (2005).
Merbach et al. (eds.), The Chemistry of Contrast Agents in Medical Magnetic Resonance Imaging, 1st ed., New York: Wiley (2001).
Miller et al., Antisense oligonucleotides: Strategies for delivery. PSTT, 1(9): 377-86 (1998).
Milne et al., An approach to gene-specific transcription inhibition using oligonucleotides complementary to the template strand of the open complex. Proc. Natl. Acad. Sci. USA, 97(7): 3136-41 (2000).
Mirkin et al., A DNA-based method for rationally assembling nanoparticles into macroscopic materials, Nature, 382(6592):607-9 (1996).
Mittal, Improving the efficiency of RNA interference in mammals, Nat. Rev. Genet., 5(5):355-65 (2004).
Modo et al., Mapping transplanted stem cell migration after a stroke: a serial, in vivo magnetic resonance imaging study, Neuroimage, 21(1):311-7 (2004).
Moriggi et al., Gold nanoparticles functionalized with gadolinium chelates as high-relaxivity MRI contrast agents, J. Am. Chem. Soc., 131(31):10828-9 (2009).
Moughton et al., Hollow nanostructures from self-assembled supramolecular metallo-triblock copolymers, Soft Matter, 5(12):2361-70 (2009).
Mucic et al., Synthesis and characterization of DNA with ferrocenyl groups attached to their 5'-termini: electrochemical characterization of a redox-active nucleotide monolayer, Chem. Comm., 555-7 (1996).
Myers et al., A cyclopentane conformational restraint for a peptide nucleic acid: design, asymmetric synthesis, and improved binding affinity to DNA and RNA. Org Lett., 5(15): 2695-8 (2003).
Nam et al., Nanoparticle-based bio-bar codes for the ultrasensitive detection of proteins. Science, 301: 1884-6 (2003).
Nitin et al., Peptide-linked molecular beacons for efficient delivery and rapid mRNA detection in living cells. Nucl. Acids Res., 32: e58 (2004).
Nitin, et al. "Oligonucleotide-Coated Metallic Nanoparticles as a Flexible Platform for Molecular Imaging Agents," Bioconjugate Chem. 18:2090-2096 (2007).
Non-Final Office Action issued in connection with U.S. Appl. No. 11/917,680, dated Jun. 8, 2011.
Non-Final Office Action issued in connection with U.S. Appl. No. 12/130,643, dated Jan. 13, 2011.
Non-Final Office Action issued in connection with U.S. Appl. No. 12/526,560, dated Mar. 15, 2012.
Non-Final Office Action issued in connection with U.S. Appl. No. 12/625,537, dated May 23, 2012.
Non-Final Office Action issued in connection with U.S. Appl. No. 12/684,836, dated Jan. 6, 2012.
Non-Final Office Action issued in connection with U.S. Appl. No. 12/684,836, dated May 17, 2012.
Non-Final Office Action issued in connection with U.S. Appl. No. 12/724,395, dated Feb. 17, 2012.
Notice of Allowance issued in connection with U.S. Appl. No. 11/917,680, dated Apr. 26, 2012.
Nuzzo et al., Spontaneously organized molecular assemblies. 3. Preparation and properties of solution adsorbed monolayers of organic disulfides on gold surfaces, J. Am. Chem. Soc., 109:2358-68 (1987).
Nykypanchuk et al., DNA-guided crystallization of colloidal nanoparticles. Nature, 451: 549-52 (2008).
O'Meara et al., Capture of single-stranded DNA assisted by oligo-nucleotide modules. Anal. Biochem., 255: 195-203 (1998).
O'Reilly et al., Identification of an activating transcription factor (ATF) binding site in the human transforming growth factor-beta 2 promoter. J. Biol. Chem., 267: 19938-43 (1992).
Ohishi et al., Hepatocellular carcinoma detected by iodized oil. Use of anticancer agents, Radiology, 154(1):25-9 (1985).
Ohuchi et al., In vitro method for the generation of protein libraries using PCR amplification of a single DNA molecule and coupled transcription/translation, Nucl. Acids Res., 26: 4339-46 (1998).
Okayasu et al., Selective and persistent deposition and gradual drainage of iodized oil, Lipiodol in the hepatocellular carcinoma after injection into the feeding hepatic artery, Am. J. Clin. Pathol., 90(5):536-44 (1988).
Ono et al., DNA triplex formation of oligonucleotide analogues consisting of linker groups and octamer segments that have opposite sugar-phosphate backbone polarities. Biochemistry, 30(41): 9914-2 (1991).
Opalinska et al., Nucleic-acid therapeutics: basic principles and recent applications. Nat. Rev. Drug Discov., 1: 503-14 (2002).
Ow Sullivan et al., Development of a novel gene delivery scaffold utilizing colloidal gold-polyethylenimine conjugates for DNA condensation. Gene Ther., 10(22): 1882-90 (2003).
Ozpolat et al., Nanomedicine based approaches for the delivery of siRNA in cancer, J. Intern. Med., 267(1):44-53 (2010).
Paciotti et al., Colloidal gold: a novel nanoparticle vector for tumor directed drug delivery, Drug Deliv., 11(3):169-83 (2004).
Parak et al., Biological applications of colloidal nanocrystals, Nanotechnol., 14: R15-27 (2003).
Park et al., Array-based electrical detection of DNA with nanoparticle probes. Science, 295: 1503-6 (2002).
Park et al., DNA-programmable nanoparticle cystrallization. Nature, 451: 553-6 (2008).
Park et al., Gold nanoparticles functionalised by Gd-complex of DTPA-bis(amide) conjugate of glutathione as an MRI contrast agent, Bioorg. Med. Chem. Lett., 18(23):6135-7 (2008).
Parrish et al., Functional anatomy of a dsRNA trigger: Differential requirement for the two trigger strands in RNA interference. Mol. Cell, 6: 1077-87 (2000).
Patel et al., Peptide antisense nanoparticles. Proc. Natl. Acad. Sci. USA, 105: 17222-6 (2008).
Patel et al., Scavenger receptors mediate cellular uptake of polyvalent oligonucleotide-functionalized gold nanoparticles, Bioconjug. Chem., 21(12):2250-6 (2010).
Patil et al., DNA-based therapeutics and DNA delivery systems: a comprehensive review. AAPS J., 7(1):E61-77 (2005).
Paunesku et al., Gadolinium-conjugated TiO2-DNA oligonucleotide nanoconjugates show prolonged intracellular retention period and T1-weighted contrast enhancement in magnetic resonance images, Nanomedicine, 4(3):201-7 (2008).
Peng et al., Real-time detection of gene expression in cancer cells using molecular beacon imaging: New strategies for cancer research. Cancer Res., 65: 1909-17 (2005).
Penn et al., Nanoparticles for bioanalysis. Curr. Opin. Chem. Biol., 7: 609-15 (2003).
Peracchi, Prospects for antiviral ribozymes and deoxyribozymes. Rev. Med. Virol., 14: 47-64 (2004).
Perlette et al., Real-time monitoring of intracellular mRNA hybridization inside single living cells. Anal. Chem., 73: 5544-50 (2001).
Pon, Solid-phase supports for oligonucleotide synthesis. Meth. Molec. Biol., 20: 465-96 (1993).
Prausnitz et al., Transdermal drug delivery, Nat. Biotechnol., 26: 1261-8 (2008).
Prigodich et al., Nano-flares for mRNA regulation and detection. ACS Nano, 3: 2147-52 (2009).
Prime et al., Self-assembled organic monolayers; Model systems for studing adsorption of proteins at surfaces. Science, 252: 1164-7 (1991).
Raj et al., Stochastic mRNA synthesis in mammalian cells. PLoS Biol., 4(10): e309 (2006).

(56) References Cited

OTHER PUBLICATIONS

Rethore et al., Preparation of chitosan/polyglutamic acid spheres based on the use of polystyrene template as nonviral gene carrier. *Tissue Engineering*, 15(4): 605-13 (2009).
Rethore et al., Use of templates to fabricate nanoscale spherical structures for defined architectural control, Small, 6(4):488-98 (2010).
Riccelli et al., Hybridization of single-stranded DNA targets to immobilized complementary DNA probes: comparison of hairpin versus linear capture probes. Nucl. Acids Res., 29: 996-1004 (2001).
Richardson et al., Tethered oligonucleotide probes. A strategy for the recognition of structured RNA. J. Am. Chem. Soc., 113(13): 5109-11 (1991).
Rihova et al., Receptor-mediated targeted drug or toxin delivery. Adv. Drug Deliv. Rev., 29(3): 273-89 (1998).
Rizzo et al., Chimeric RNA-DNA molecular beacon assay for ribonuclease H activity. Mol. Cell Probes, 16:277-83 (2002).
Rosi et al., Nanostructures in biodiagnostics, Chem. Rev., 105(4):1547-62 (2005).
Sadauskas et al., Protracted elimination of gold nanoparticles from mouse liver, Nanomedicine, 5(2):162-9 (2009).
Sandhu et al., Gold nanoparticle-mediated transfection of mammalian cells. Bioconjugate Chem., 13: 3-6 (2002).
Santangelo et al., Dual FRET molecular beacons for mRNA detection in living cells. Nucl. Acids Res., 32:e57 (2004).
Santangelo et al., Nanostructured probes for RNA detection in living cells. Ann. Biomed. Eng., 34:39-50 (2006).
Schifferlers et al., Cancer siRNA therapy by tumor selective delivery with ligand-targeted sterically stabilized nanoparticle. *Nucl. Acid Res.*, 32(19): e149 (2004).
Seela et al., Oligodeoxyribonucleotides containing 1,3-propanediol as nucleoside substitute. Nucl. Acids Res., 15(7): 3113-29 (1987).
Seelig et al., Catalyzed relaxation of a metastable DNA fuel. J. Am. Chem. Soc., 128: 12211-20 (2006).
Seferos et al., "Polyvalent DNA nanoparticle conjugates stabilize nucleic acids," Nano Lett. 9(1):308-11 (2009).
Seferos et al., Locked nucleic acid-nanoparticle conjugates. Chembiochem., 8: 1230-2 (2007).
Sharma et al., Characterization of MRI contrast agent-loaded polymeric nanocapsules as versatile vehicle for targeted imaging, Contrast Media Mol. Imaging, 5(2):59-69 (2010).
Sharma et al., Mutant V599EB-Raf regulates growth and vascular development of malignant melanoma tumors. Cancer Res., 65: 2412-21 (2005).
Sharma et al., Targeting Akt3 signaling in malignant melanoma using isoselenocyanates. Clin. Cancer Res., 15:.1674-85 (2009).
Sharma et al., Targeting mitogen-activated protein kinase/extracellular signal-regulated kinase kinase in the mutant (V600E) B-Raf signaling cascade effectively inhibits melanoma lung metastases. Cancer Res., 66: 8200-9 (2006).
Sharp et al., RNA interference—2001. Genes Dev., 15: 485-90 (2001).
Shu et al., Gradient cross-linked biodegradable polyelectrolyte nanocapsules for intracellular protein drug delivery, Biomaterials, 31(23):6039-49 (2010).
Simmel et al., DNA nanodevices. Small, 1: 284-99 (2005).
Skwarczynski et al., Paclitaxel prodrugs: toward smarter delivery of anticancer agents, J. Med. Chem., 49(25):7253-69 (2006).
Smith et al., Bioconjugated quantum dots for in vivo molecular and cellular imaging, Adv. Drug Deliv. Rev., 60(11):1226-40 (2008).
Sokol et al., Real time detection of DNA.RNA hybridization in living cells. Proc. Natl. Acad. Sci. USA, 95: 11538-43 (1998).
Song et al., Synthesis of multimeric MR contrast agents for cellular imaging, J. Am. Chem. Soc., 130(21):6662-3 (2008).
Soriaga et al., "Determination of the orientation of aromatic molecules adsorbed on platinum electrodes. The effect of solute concentration." J. Am. Chem. Soc., 104:3937-3945 (1982).
Srivastava et al., Use of riboprobes for northern blotting analysis. Biotechniques, 11 (5): Abstract (1991).

Stahl et al., Deregulated Akt3 activity promotes development of malignant melanoma, Cancer Res., 64: 7002-10(2004).
Stephenson et al., Inhibition of Rous sarcoma viral RNA translation by a specific oligodeoxyribonucleotide. Proc. Natl. Acad. Sci. USA, 75(1): 285-8 (1978).
Stoermer et al., Distance-dependent emission from dye-labeled oligonucleotides on striped Au/Ag nanowires: effect of secondary structure and hybridization efficiency. J. Am. Chem. Soc., 128: 13243-54 (2006).
Stoeva et al., Multiplexed detection of protein cancer markers with biobarcoded nanoparticle probes. J. Am. Chem. Soc., 128: 8378-9 (2006).
Storhoff et al., One-pot colorimetric differentiation of polynucleotides with single base imperfections using gold nanoparticle probes, J. Am. Chem. Soc., 120:1959-64 (1998).
Storhoff et al., What controls the optical properties of DNA-linked gold nanoparticle assemblies? J. Am. Chem. Soc., 122: 4640-50 (2000).
Storz et al., An abundance of RNA regulators, Annu. Rev. Biochem., 74:199-217 (2005).
Sugihara et al., One-pot synthesis of biomimetic shell cross-linked micelles and nanocages by ATRP in alcohol/water mixtures, Angew. Chem. Int. Ed. Engl., 48(20):3500-3 (2010).
Sun et al., Ganglioside loss promotes survival primarily by activating integrin-linked kinase/Akt without phosphoinositide 3-OH kinase signaling. J. Invest. Dermatol., 119: 107-17 (2002).
Sundaram et al., Particle-mediated delivery of recombinant expression vectors to rabbit skin induces high-titered polyclonal antisera (and circumvents purification of a protein immunogen). Nucl. Acids Res., 24(7): 1375-7 (1996).
Tan et al., Facile synthesis of hybrid silica nanocapsules by interfacial templating condensation and their application in fluorescence imaging, Chem. Commun. (Camb.), Nov. 7(41):6240-2 (2009).
Taton et al., Scanometric DNA array detection with nanoparticle probes, Science, 289(5485):1757-60 (2000).
Thomas et al., Conjugation to gold nanoparticles enhances polyethylenimine's transfer of plasmid DNA into mammalian cells. Proc. Natl. Acad. Sci. USA, 100(16): 9138-43 (2003).
Thompkins et al., The study of the gas-solid interaction of acetic acid with a cuprous oxide surface using reflection-absorption spectroscopy. J. Colloid Interface Sci., 49: 410-21 (1974).
Thurn et al., Labeling TiO2 nanoparticles with dyes for optical fluorescence microscopy and determination of TiO2-DNA nanoconjugate stability, Small, 5(11):1318-25 (2009).
Timmons et al., Investigation of fatty acid monolayers on metals by contact potential measurements, J. Phys. Chem., 69:984-90 (1965).
Tkachenko et al., Cellular trajectories of peptide-modified gold particle complexes: comparison of nuclear localization signals and peptide transduction domains. Bioconjugate Chem., 15(3): 482-90 (2004).
Tkachenko et al., Multifunctional gold nanoparticle-peptide complexes for nuclear targeting. J. Am. Chem. Soc., 125: 4700-1 (2003).
Treisman, The SRE: a growth factor responsive transcriptional regulator. *Semin. Cancer Biol.*, 1: 47-58 (1990).
Tsao et al., Genetic interaction between NRAS and BRAF mutations and PTEN/MMAC1 inactivation in melanoma. J. Invest. Dermatol., 122: 337-41 (2004).
Turberfield et al., DNA fuel for free-running nanomachines. Phys. Rev. Lett., 90: 118102 (2003).
Turner et al., Nanoscale Cage-like Structures Derived from Polyisoprene-Containing Shell Cross-linked Nanoparticle Templates, Nano Lett., 4(4):683-8 (2004).
Tyagi et al., Molecular beacons: Probes that fluoresce upon hybridization. Nat. Biotechnol., 14: 303-8 (1996).
Vasiliskov et al., Parallel multiplex thermodynamic analysis of coaxial base stacking in DNA duplexes by oligodeoxyribonucleotide microchips. Nucl. Acids Res., 29: 2303-13 (2001).
Virmani et al., Comparison of two different methods for inoculating VX2 tumors in rabbit livers and hind limbs, J. Vasc. Interv. Radiol., 19(6):931-6 (2008).
Wagner et al., Gene inhibition using antisense oligodeoxynucleotides. Nature, 372: 333-5 (1994).

(56) References Cited

OTHER PUBLICATIONS

Wang et al., Ganglioside GM3 inhibits matrix metalloproteinase-9 activation and disrupts its association with integrin, J. Biol. Chem., 278: 25591-9 (2003).
Wang et al., Ganglioside GM3 promotes carcinoma cell proliferation via urokinase plasminogen activator-induced extracellular signal-regulated kinase-independent p70S6 kinase signaling, J. Invest. Dermatol., 126: 2687-96 (2006).
Wang et al., Inhibition of integrin-linked kinase/protein kinase B/Akt signaling: mechanism for ganglioside-induced apoptosis. J. Biol. Chem., 276: 44504-11 (2001).
Wang et al., Locked nucleic acid molecular beacons. J. Am. Chem. Soc., 127: 15664-5 (2005).
Wang et al., Molecular engineering of DNA: molecular beacons. Angew. Chem., Int. Ed., 48: 856-70 (2009).
Wang et al., Nanoparticles for multiplex diagnostics and imaging. Nanomedicine (Lond.), 1: 413-26 (2006).
Wang et al., Speeding up a single-molecule DNA device with a simple catalyst. Phys. Rev. E Stat. Nonlin. Soft Matter. Phys., 72: 051918 (2005).
Wang et al., Superparamagnetic sub-5 nm Fe@C nanoparticles: isolation, structure, magnetic properties, and directed assembly, Nano Lett., 8(11):3761-5 (2008).
Wasserman et al., Structure and reactivity of alkylsiloxane monolayers formed by reaction of alkyltrichlorosilanes on silicon substrates, Langmuir, 5:1074-87 (1989).
Wei et al., A study of the relationships between oligonucleotide properties and hybridization signal intensities from NimbleGen microarray datasets. Nucl. Acids Res., 36: 2926-38 (2008).
Wellbrock et al., V599EB-RAF is an oncogene in melanocytes. Cancer Res., 64: 2338-42 (2004).
Whitesides, Proceedings of the Robert A. Welch Foundation 39th Conference on Chemical Research Nanophase Chemistry, Houston, Tex., pp. 109-121 (1995).
Wikipedia entry on Aspirin, Last modified on Oct. 6, 2010 (online). Retrieved on Oct. 7, 2010). Retrieved from the Internet: <URL: http://en.wikipedia.org/wiki/Aspirin>.
Wikipedia entry on Phenylbutazone. Last modified on Sep. 20, 2010. Online. (Retrieved on Oct. 7, 2010). Retrieved from the Internet: <URL:http://en.wikipedia.org/wiki/Phenylbutazone>.
Wikipedia entry on Warfarin. Last modified on Oct. 5, 2010. (Online) (Retrieved on Oct. 8, 2010). Retrieved from the Internet: <URL:http://en.wikpedia.org/wiki/Warfarin>.
Winter et al., Molecular imaging by MRI, Curr. Cardiol. Rep. 8(1):65-9 (2006).
Wolf et al., Rapid hybridization kinetics of DNA attached to submicron latex particles. Nucl. Acids Res., 15: 2911-26 (1987).
Xia, Nanomaterials at work in biomedical research, Nat. Mater., 7(10):758-60 (2008).
Xu et al., A gold-nanoparticle-based real-time colorimetric screening method for endonuclease activity and inhibition, Angew. Chem. Int. Ed. Engl., 46(19):3468-70 (2007).
Xu et al., Homogeneous detection of nucleic acids based upon the light scattering properties of silver-coated nanoparticle probes, Anal. Chem., 79(17):6650-4 (2007).
Xu et al., Thermodynamics of DNA hybridization on gold nanoparticles. J. Am. Chem. Soc., 127(38): 13227-31 (2005).
Yang et al., Evidence that processed small dsRNAs may mediate sequence-specific mRNA degradation during RNAi in *Drosophila* embryos. Curr. Biol., 10: 1191-200 (2000).
Ye et al., Characterization of a silencer regulatory element in the human interferon-gamma promoter. *J. Biol. Chem.*, 269: 25728-34 (1994).
Yin Win et al., Effects of particle size and surface coating on cellular uptake of polymeric nonparticles for oral delivery of anticancer drugs. Biomaterials, 26: 2713-22 (2005).
You et al., Detection and identification of proteins using nanoparticle-fluorescent polymer 'chemical nose' sensors. Nat. Nanotechnol., 2: 318-23 (2007).

You et al., Engineering the nanoparticle-biomacromolecule interface. Soft Matter, 2: 190-204 (2006).
Zabner et al., Cellular and molecular barriers to gene transfer by a cationic lipid. J. Biol. Chem., 270: 18997-9007 (1995).
Zamecnik et al., Inhibition of Rous sarcoma virus replication and cell transformation by a specific oligodeoxynucleotide. Proc. Natl. Acad. Sci. USA, 75(1): 280-4 (1978).
Zamore et al., RNAi: double-stranded RNA directs the ATP-dependent cleavage of mRNA at 21 to 23 nucleotide intervals. Cell, 101: 25-33 (2000).
Zhang et al., A novel paclitaxel-loaded poly(epsilon-caprolactone)/Poloxamer 188 blend nanoparticle overcoming multidrug resistance for cancer treatment, Acta Biomater., 6(6):2045-52 (2010).
Zhang et al., Cationic shell-crosslinked knedel-like nanoparticles for highly efficient gene and oligonucleotide transfection of mammalian cells, Biomaterials, 30(5):968-77 (2009).
Zhang et al., Control of DNA strand displacement kinetics using toehold exchange. J. Am. Chem. Soc., 131: 17303-14 (2009).
Zhang et al., PowerBLAST: a new network BLAST application for interactive or automated sequence analysis and annotation, Genome Res., 7(6):649-56 (1997).
Zhang et al., Self-assembled monolayers of terminal alkynes on gold, J. Am. Chem. Soc., 129(16):4876-7 (2007).
Zhang et al., Single-quantum-dot-based DNA sensor. Nat. Mater., 4: 826-31 (2005).
Zhao et al., A rapid bioassay for single bacterial cell quantitation using bioconjugated nanoparticles, Proc. Natl. Acad. Sci. USA, 101(42):15027-32 (2004).
Zheng et al., Aptamer nano-flares for molecular detection in living cells. Nano Lett., 9: 3258-61 (2009).
Zimmer, Antisense oligonucleotide delivery with polyhexylcyanoacrylate nanoparticles as carriers. Methods, 18: 286-95 (1999).
U.S. Appl. No. 13/518,443, Published as US-2013/0178610, filed Oct. 3, 2012.
U.S. Appl. No. 15/337,674, Published as US-2017/0044544, filed Oct. 28, 2016.
International Preliminary Report on Patentability from International Application No. PCT/US2015/062005 dated May 23, 2017.
Ahmadi et al., "Shape-Controlled Synthesis of Colloidal Platinum Nanoparticles," Science 272(5270):1924-1926 (1996).
Bahnemann, "Mechanisms of Organic Transformations on Semi-conductor Particles," in Photochemical Conversion and Storage of Solar Energy (eds. Pelizetti and Schiavello) p. 251-276 (1991).
Brus, "Quantum Crystallites and Nonlinear Optics," Appl. Phys. A., 53:465-474 (1991).
Chen et al., "Ionic strength-dependent persistence lengths of single-stranded RNA and DNA," Proc Natl Acad Sci USA 109:799-804 (2012).
Cheng et al., "Synthesis of linear, beta-cyclodextrin-based polymers and their camptothecin conjugates," Bioconjug Chem 14: 1007-1017 (2003).
Choi et al., "Mechanism for the endocytosis of spherical nucleic acid nanoparticle conjugates," Proc Natl Acad Sci U.S.A. 110: 7625-7630 (2013).
Concise Encyclopedia of Polymer Science and Engineering, "Polynucleotides," J. I. Kroschwitz Ed., John Wiley & Sons, pp. 858-859 (1990).
Cook, "Medicinal chemistry of antisense oligonucleotides—future opportunities," Anti-Cancer Drug Design 6:585-607 (1991).
Crawford et al., "Peptide aptamers: Tools for biology and drug discovery," Briefings in Functional Genomics and Proteomics, 2(1):72-79 (2003).
Crooke, S. T. and Lebleu, B., Ed., CRC Press "Antisense Research and Applications" Table of Contents (1993).
Curtis et al, "A Morphology-Selective Copper Organosol," Angew. Chem. Int. Ed. Engl., 27:1530-1533 (1988).
Cutler et al., "Spherical Nucleic Acids," J Am Chem Soc 134: 1376-1391 (2012).
De Mesmaeker et. al., "Backbone modifications in oligonucleotides and peptide nucleic acid systems," Current Opinion in Structural Biology, 5:343-355 (1995).

(56) References Cited

OTHER PUBLICATIONS

Demers et al., "Thermal Desoprtion Behavior and Binding Properties of DNA Bases and Nucleosides on Gold," J A Chem Soc 124:11248-11249 (2002).
Englisch et al., "Chemically Modified Oligonucleotides as Probes and Inhibitors," Angewandte Chemie, International Edition, 30(6):613-722 (1991).
Enüstün et al., "Coagulation of Colloidal Gold," J. Am. Chem. Soc. 85:3317-3328 (1963).
Fattal et al., "Biodegradable polyalkylcyanoacrylate nanoparticles for the delivery of oligonucleotides," J. Controlled Release 53:137-143 (1998).
Freier et al., "The ups and downs of nucleic acid duplex stability: structure-stability studies on chemically-modified DNA:RNA duplexes," Nucleic Acids Research, 25(22):4429-4443 (1997).
Gehring et al., "A tetrameric DNA structure with protonated cytosine-cytosine base pairs," Nature 363:561-565 (1993).
Giljohann et al., "Gene Regulation with Polyvalent siRNA-Nanoparticle Conjugates," J Am Chem Soc 131: 2072-2073 (2009).
Giljohann et al., "Oligonucleotide Loading Determines Cellular Uptake of DNA-Modified Gold Nanoparticles," Nano Lett 7: 3818-3821 (2007).
Hayashi, "Ultrafine particles," J. Vac. Sci. technol. 5(4):1375-1384 (1987).
Hayashi, "Ultrafine Particles," Physics Today 44-60 (1987).
Henglein et al., "Absorption Spectrum and Some Chemical Reactions of Colloidal Platinum in Aqueous Solution," J. Phys. Chem., 99:14129-14136 (1995).
Henglein, "Mechanism of Reactions on Colloidal Microelectrodes and Size Quantization Effects," Top. Curr. Chem., 143:113-180 (1988).
Henglein, "Small-Particle Research: Physiochemical Properties of Extremely Small Colloidal Metal and Semiconductor Particles," Chem. Rev., 89:1861-1873 (1989).
Hurst et al., "Maximizing DNA Loading on a Range of Gold Nanoparticle Sizes," Anal Chem 78(24): 8313-8318 (2006).
Huxley et al., "Preferential Staining of Nucleic Acid-Containing Structures for Electron Microscopy," J Biophys Biochem Cytol 11:273-296 (1961).
International search report and written opinion from PCT/US15/62005 dated May 19, 2016.
Jensen et al., "Spherical Nucleic Acid Nanoparticle Conjugates as an RNAi-Based Therapy for Glioblastoma," Sci Transl Med 5, 209ra152 (2013).
Katz, "The reversible reaction of sodium thymonucleate and mercuric chloride," J. Am. Chem. Soc., 74:2238-2245 (1951).
Kimura-Suda et al., "Base-Dependent Competive Adsorption of Single-Stranded DNA on Gold," Journal of the American Chemical Society 125: 9014-9015 (2003).
Kopylov et al., "Combinatorial Chemistry of Nucleic Acids: SELEX," Molecular Biology 34(6): 940-954 (2000) tranlsated from Molekulyarnaya Biologiya, vol. 34, No. 6 pp. 1097-1113 (2000).
Kosturko et al., "The Crystal and Molecular Structure of a 2:1 Complex of 1-Methylthymine-Mercury(II)," Biochemistry, 13:3949-3952 (1974).
Kukowska-Latallo et al., "Efficient transfer of genetic material into mammalian cells using Starburst polyamidoamine dendrimers," Proc. Natl. Acad. Sci. USA 93:4897-4902 (1996).
Kumar et al., "Directional conjugation of antibodies to nanoparticles for synthesis of multiplexed optical contrast agents with both delivery and targeting moieties," Nat Protoc 3:314-320 (2008).
Liu et al., "New Poly(D-glucaramidoamine)s Induce DNA Nanoparticle Formation and Efficient Gene Delivery into Mammalian Cells," J. Am. Chem. Soc. 126:7422-7423 (2004).
Marinakos et al., "Gold Nanoparticles as Templates for the Synthesis of Hollow Nanometer-Sized Conductive Polymer Capsules," Adv. Mater. 11: 34-37 (1999).
Marinakos et al., "Template Synthesis of One-Dimensional Au, Au-Poly(pyrrole), and Poly(pyrrole) Nanoparticle Arrays," Chem. Mater. 10:1214-19 (1998).
Martin et al., "A New Access to 2'O-Alkylated Ribonucleosides and Properties of 2'-O-Alkylated Oligoribonucleotides," Helv. Chim. Acta, 78:486-504 (1995).
Massart, "Preparation of Aqueous Magnetic Liquids in Alkaline and Acidic Media," IEEE Transactions on Magnetics, 17:1247-1248 (1981).
Massich et al., "Regulating Immune Response Using Polyvalent Nucleic Acid-Gold Nanoparticle Conjugates," Mol Pharm 6: 1934-1940 (2009).
Matijevic et al., "Fine Particles Part II: Formation Mechanisms and Applications," MRS Bulletin pp. 16-47 (1990).
Nielsen et al., "Sequence-selective recognition of DNA by strand displacement with a thymine-substituted polyamide," Science, 254:1497-1500 (1991).
Olshavsky et al., "Organometallic Synthesis of GaAs Crystallites Exhibiting Quantum Confinement," J. Am. Chem. Soc., 112, 9438-9439 (1990).
Opdahl et al., "Independent control of grafting density and conformation of single-stranded DNA brushes," Proc Natl Acad Sci U.S.A. 104: 9-14 (2007).
Parrish et al., "Soluble Camptothecin Derivatives Prepared by Click Cycloaddition Chemistry on Functional Aliphatic Polyesters," Bioconjugate Chem. 18: 263-267 (2006).
Pearson et al., "Polynucleotide Binding to Macrophage Scavenger Receptors Depends on the Formation of Base-quartet-stabilized Four-stranded Helices," J Biol Chem 268: 3546-3554 (1993).
Prasad, et al. "Oligonucleotides Tethered to a Short Polyguanylic Acid Stretch are Targeted to Macrophages: Enhanced Antiviral Activity of a Vesicular Stomatitis Virus-Specific Antisense Oligonucleotide," Antimicrobial Agents and Chemotherapy, 43(11):2689-2696 (1999).
Rosi et al., "Oligonucleotide-Modified Gold Nanoparticles for Intracellular Gene Regulation," Science 312: 1027-1030 (2006).
Sanghvi, "Heterocyclic Base Modification in Nucleic Acids and Their Applications in Antisense Oligonucleotides," Chapter 15 in Antisense Research and Application, Ed. S. T. Crooke and B. Lebleu, CRC Press (1993).
Seferos et al., "Nano-Flares: Probes for Transfection and mRNA Detection in Living Cells," J Am Chem Soc 129: 15477-15479 (2007).
Sen et al., "Formation of parallel four-stranded complexes by guanine-rich motifs in DNA and its implications for meiosis," Nature 334:364-366 (1988).
Stefanis et al., "Caspase-Dependent and -Independent Death of Camptothecin-Treated Embryonic Cortical Neurons," J Neurosci 19(15):6235-6247 (1999).
Storhoff et al., "Sequence-Dependent Stability of DNA-Modified Gold Nanoparticles," Langmuir 18: 6666-6670 (2002).
Thomas, "The Interaction of HgCl2 with Sodium Thymonucleate," J. Am. Chem. Soc., 76:6032-6034 (1954).
Tondelli, et al., "Highly efficient cellular uptake of c-myb antisense oligonucleotides through specifically designed polymeric nanospheres," Nucl. Acids Res. 26:5425-5431 (1998).
Tuerk et al., "Systematic Evolution of Ligands by Exponential Enrichment: RNA Ligands to Bacteriophage T4 DNA Polymerase," Science 249:505-510 (1990).
Ushida et al., "GaAs Nanocrystals Prepared in Quinoline," IJ. Phys. Chem., 95, 5382-5384 (1992).
Wang et al., "Nanometer-Sized Semiconductor Clusters: Materials Synthesis, Quantum Size Effects, and Photophysical Properties," J. Phys. Chem., 95:525-532 (1991).
Weller, "Colloidal Semiconductor Q-Particles: Chemistry in the Transition Region Between Solid State and Molecules," Angew. Chem. Int. Ed. Engl., 32:41-53 (1993).
Yamane et al., "On the complexing of desoxyribonucleic acid (DNA) by mercuric ion," J. Am. Chem. Soc., 83:2599-2607 (1961).
Yan et al., "Aptamers and aptamer targeted delivery," RNA Biol. 6(3) 316-320 (2009).
Zamai et al., "Camptothecin Poly[N-(2-Hydroxypropyl) Methacrylamide] Copolymers in Antitopoisomerase-I Tumor Therapy: Intrtumor Release and Antitumor Efficacy," Mol Cancer Ther 2: 29-40 (2003).

(56) References Cited

OTHER PUBLICATIONS

Zhang et al., "A general approach to DNA-programmable atom equivalents," Nat Mater 12(8): 741-746 (2013).
Zhang et al., "An extremely stable and orthogonal DNA base pair with a simplified three-carbon backbone," J. Am. Chem. Soc., 127:74-75 (2005).
Zheng et al., "Topical delivery of siRNA-based spherical nucleic acid nanoparticle conjugates for gene regulation," Proc Natl Acad Sci U.S.A. 109: 11975-11980 (2012).
Zimmermann, et al., "A Novel Silver(I)-Mediated DNA Base Pair," J. Am. Chem. Soc., 124:13684-13685 (2002).
[No Author Listed] KeraFAST Chemoselective ligation through copper-free click chemistry. Sep. 21, 2012. published online via http://www.kerafast.com/PDF/Chemoselective_Ligation_Sheet.pdf 2 pages.
[No Author] IDT Integrated DNA Technologies also describes in their company website A-class, B-class and C-class CpG oligonucleotides.
Agbasi-Porter et al., Transcription inhibition using oligonucleotide-modified gold nanoparticles, Bioconjugate Chem., 17(5):1178-83 (2006).
Akhter et al., Gold nanoparticles in theranostic oncology: current state-of-the-art. Expert Opin Drug Deliv. Oct. 2012;9(10):1225-43. Epub Aug. 16, 2012.
Alemdaroglu et al., DNA Block Copolymer Micelles—A Combinatorial Tool for Cancer Nanotechnology. Advanced Materials. Mar. 2008;20(5)899-902. https://doi.org/10.1002/adma.200700866l.
Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Bae et al., Targeted drug delivery to tumors: myths, reality and possibility. J Control Release. Aug. 10, 2011;153(3):198-205. doi: 10.1016/j.jconrel.2011.06.001. Epub Jun. 6, 2011.
Banga et al., Liposomal spherical nucleic acids. J Am Chem Soc. Jul. 16, 2014; 136(28):9866-9. doi: 10.1021/ja504845f. Epub Jul. 1, 2014.
Bhattarai et al., "Enhanced Gene and siRNA Delivery by Polycation-Modified Mesoporous Silica Nanoparticles Loaded with Chloroquine," Pharm. Res., 2010, 27, 2556-2568.
Bonoiu et al., Nanotechnology approach for drug addiction therapy: gene ; silencing using delivery of gold nanorod-siRNA nanoplex in dopaminergic neurons. Proc Natl Acad Sci USA. Apr. 7, 2009;106(14):5546-50. doi:; 10.1073/pnas.0901715106. Epub Mar. 23, 2009.
Briley et al., In Nanomaterials for Biomedicine; American Chemical Society. 2012;1119:1-20.
Bunge et al., Lipophilic oligonucleotides spontaneously insert into lipid membranes, bind complementary DNA strands, and sequester into lipid-disordered domains. Langmuir. Apr. 10, 2007;23(8):4455-64. Epub Mar. 17, 2007.
Burgess, Liposome preparation—Avanti® Polar Lipids. Sigma-Aldrich. 1998. 3 pages.
Cao et al., Reversible Cell-Specific Drug Delivery with Aptamer-Functionalized Liposomes, Anqew. Chem. Int. Ed. 2009;48:6494-8.
Chen et al., Nanoparticle-aptamer: an effective growth inhibitor for human cancer cells. IMECE 2009-11966. Jul. 8, 2010;271-2. https://doi.org/10.1115/IMECE2009-11966. 2 pgs.
Chinen et al., Spherical nucleic acid nanoparticle conjugates enhance G-quadruplex formation and increase serum protein interactions. Angew Chem Int Ed Engl. Jan. 7, 2015;54(2):527-31. doi: 10.1002/anie.201409211. Epub Nov. 13, 2014.
Chinese Office Action dated Oct. 28, 2019 in connection with CN 201580073536.9.
Chinnathambi et al., Binding mode of CpG Oligodeoxynucleotides to nanoparticles regulates bifurcated cytokine induction via Toll-like Receptor 9. Sci Reports. 2012;2(534):1-9.

Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Cho et al., Therapeutic nanoparticles for drug delivery in cancer. Clin Cancer Res. Mar. 1, 2008;14(5):1310-6. doi: 10.1158/1078-0432.CCR-07-1441.
Choi et al., DNA aptamer-passivated nanocrystal synthesis: a facile approach for nanoparticle-based cancer cell growth inhibition. Small. Mar. 2009;5(6):672-5. doi: 10.1002/smll.200801821.
Cutler et al., Polyvalent nucleic acid nanostructures. J Am Chem Soc. Jun. 22, 2011;133(24):9254-7. doi:10.1021/ja203375n. Epub Jun. 1, 2011.
Cutler et al., Polyvalent oligonucleotide iron oxide nanoparticle "click" conjugates. Nano Lett. Apr. 14, 2010;10(4):1477-80. doi: 10.1021/nl100477m.
Dave et al., Programmable assembly of DNA-functionalized liposomes by DNA. ACS Nano. Feb. 22, 2011;5(2):1304-12. doi: 10.1021/nn1030093. Epub Jan. 4, 2011.
Diebold et al., Nucleic acid agonists for Toll-like receptor 7 are defined by the presence of uridine ribonucleotides. Eur J Immunol. Dec. 2006;36(12):3256-67.
Dikmen et al., Targeting critical steps of cancer metastasis and recurrence using telomerase template antagonists. Biochim Biophys Acta. Apr. 2009;1792(4):240-7. doi: 10.1016/j.bbadis.2009.01.018. Epub Feb. 9, 2009.
Dua et al., Liposome: Methods of Preparation and Applications. IJPSR (2012) 3(2):14-20.
Elbakry et al., Layer-by-Layer Assembled Gold Nanoparticles for siRNA Delivery, Nano Lett., 2009, 9 (5), 2059-2064.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Extended European Search Report dated Jun. 28, 2018 in connection with EP 15860671.5.
Farokhzad et al., Nanomedicine: developing smarter therapeutic and diagnostic modalities, Drug Delivery Rev., 58:1456 (2006).
Ferrari, Cancer nanotechnology: opportunities and challenges. Nature Reviews Cancer. 2005;5: 161-71.
Forman et al., Toward Artificial Ion Channels: A Lipophilic G-Quadruplex. J. Am. Chem. Soc. 2000;122(17):4060-4067. DOI: 10.1021/ja9925148.
Forsbach et al., Identification of RNA sequence motifs stimulating sequence-specific TLR8-dependent immune responses. J Immunol. Mar. 15, 2008;180(6):3729-38.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.
Godard et al., Antisense Effects of Cholesterol-Oligodeoxynucleotide Conjugates Associated with Poly(alkylcyanoacrylate) Nanoparticles. Eur. J. Biochem., 1995, 232 (2), 404-410.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gryaznov, Oligonucleotide n3'→p5' phosphoramidates and thiophoshoramidates as potential therapeutic agents. Chem Biodivers. Mar. 2010;7(3):477-93. doi: 10.1002/cbdv.200900187. Review.
Gunnarsson et al., Liposome-Based Chemical barcodes for Single Molecule DNA Detection Using Imaging Mass Spectrometry, Nano. Lett. 2010;10:732-37.
Gursel et al., Repetitive elements in mammalian telomeres suppress bacterial DNA-induced immune activation. J Immunol. Aug. 1, 2003;171(3):1393-400.
Han et al., Drug and gene delivery using gold nanoparticles. NanoBiotechnology. Mar. 2007;3(1):40-5.
Han et al., Selective Interactions of Cationic Porphyrins with G-Quadruplex; Structures. J. Am. Chem. Soc. 2001, 123, 8902-8913 (Year: 2001).

(56) References Cited

OTHER PUBLICATIONS

Heil et al., Species-specific recognition of single-stranded RNA via toll-like receptor 7 and 8. Science. Mar. 5, 2004;303(5663): 1526-9. Epub Feb. 19, 2004.
Hellstrom et al., Epitaxial growth of DNA-assembled nanoparticle superlattices on patterned substrates. Nano Lett. 2013;13(12):6084-90. doi: 10.1021/nl4033654. Epub Nov. 20, 2013.
Hope et al., Production of large unilamellar vesicles by a rapid extrusion procedure: characterization of size distribution, trapped volume and ability to maintain a membrane potential. Biochim Biophys Acta. Jan. 10, 1985;812(1):55-65.
Hotz et al., VEGF antisense therapy inhibits tumor growth and improves survival in experimental pancreatic cancer. Surgery. Feb. 2005;137(2):192-9.
Hurst et al., Maximizing DNA Loading on a Range of Gold Nanoparticle Sizes. Anal. Chem., 2006, 78 (24), 8313-8318.
Jahn et al., Microfluidic directed formation of liposomes of controlled size. Langmuir. May 22, 2007;23(11):6289-93. Epub Apr. 24, 2007.
Jakobsen et al., Assembly of liposomes controlled by triple helix formation, Bioconjugate Chem. 2013;24:1485-95.
Jayawickramarajah et al., Allosteric control of self-assembly: modulating the formation of guanine quadruplexes through orthogonal aromatic interactions. Angew Chem Int Ed Engl. 2007;46(40):7583-6.
Jensen et al., Spherical nucleic acid nanoparticle conjugates as an RNAi-based therapy for glioblastoma, Sci. Trans. Med., 5:209ra152 (2013).
Kachura et al., A CpG-Ficoll Nanoparticle Adjuvant for Anthrax Protective Antigen Enhances Immunogenicity and Provides Single-Immunization Protection against Inhaled Anthrax in Monkeys. J Immunol. Jan. 1, 2016;196(1):284-97. doi: 10.4049/jimmunol.1501903. Epub Nov. 25, 2015.
Kandimalla et al., Conjugation of Ligands at the 5'-End of CpG DNA Affects Immunostimulatory Activity. Bioconjugate Chemistry 2002 13 (5), 966-974. DOI: 10.1021/bc0200374.
Kerkmann et al., Immunostimulatory properties of CpG-oligonucleotides are enhanced by the use of protamine nanoparticles. Oligonucleotides. 2006 Winter;16(4):313-22.
Kim et al., Effect of bovine serum albumin on the stability of methotrexate-encapsulated liposomes, Arch. Pharmacal Res. 1991;14:336.
Kim et al., Systemic and Specific Delivery of Small Interfering RNAs to the Liver Mediated by Apolipoprotein A-I. Mol. Ther., 2007, 15 (6), 1145-1152.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Krieg. Antiinfective applications of toll-like receptor 9 agonists. Proc Am Thorac Soc. Jul. 2007;4(3):289-94.
Krug et al. Identification of CpG oligonucleotide sequences with high induction of IFN-alpha/beta in plasmacytoid dendritic cells. Eur J Immunol. Jul. 2001;31(7):2154-63.
Langer, New methods of drug delivery. Science. Sep. 28, 1990;249(4976):1527-33.
Laouini et al., iPreparation, Characterization and Applications of Liposomes: State of the Art. J Colloid Sci and Biotechnol. 2012;1:147-68.
Leander, Mixed-Monolayer Gold Nanoparticles for Cancer Therapeutics. Nanoscape, 2010, 7(1), 11-14.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Lee et al., Silver nanoparticle-oligonucleotide conjugates based on DNA with triple cyclic disulfide moieties, Nano Lett., 7: 2112 (2007).
Lennox et al., Characterization of modified antisense oligonucleotides in Xenopus laevis embryos. Oligonucleotides. 2006 Spring;16(1):26-42.

Lesieur et al., Size analysis and stability study of lipid vesicles by high-performance gel exclusion chromatography, turbidity, and dynamic light scattering. Anal Biochem. Feb. 1, 1991;192(2):334-43. (Abstract Only).
Li et al., Combination delivery of antigens and CpG by lanthanides-based core-shell nanoparticles for enhanced immune response and dual-mode imaging. Adv Healthc Mater. Oct. 2013;2(10):1309-13. doi:10.1002/adhm.201200364. Epub Mar. 25, 2013.
Li et al., Nanofabrication by DNA self-assembly. Materials Today. Elsevier Science. May 1, 2009;12(5)24-32.
Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.
Li et al., Reversible and Chemically Programmable Micelle Assembly with DNA Block-Copolymer Amphiphiles, Nano Lett. 2004;4:1055.
Li et al., Thermal stability of DNA functionalized gold nanoparticles, Bioconjugate Chem., 24:1790-7 (2013).
Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone.0063550. Print 2013.
Liu et al., Membrane anchored immunostimulatory oligonucleotides for in vivo cell modification and localized immunotherapy. Angew Chem Int Ed Engl. Jul. 25, 2011;50(31):7052-5. doi: 10.1002/anie.201101266. Epub Jun. 17, 2011.
Liu et al., Structure-based programming of lymph-node targeting in molecular vaccines. Nature. Mar. 27, 2014;507(7493):519-22. doi: 10.1038/nature12978.
Liu et al., Silica Nanoparticle Supported Lipid Bilayers for Gene Delivery, Chem. Commun., 2009, 5100-5102.
Ljubimova et al., Nanoconjugate based on polymalic acid for tumor targeting.; Chem Biol Interact. Jan. 30, 2008;171(2):195-203. Epub Feb. 8, 2007.
Lohcharoenkal et al., Protein Nanoparticles as Drug Delivery Carriers for Cancer Therapy. BioMed Research International. 2014; Article ID 180549. 12 pages. http://dx.doi.org/10.1155/2014/180549.
Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.
Lytton-Jean et al., Highly Cooperative Behavior of Peptide Nucleic Acid-Linked DNA-Modified Gold-Nanoparticle and Comb-Polymer Aggregates, Advanced Materials, 21: 706 (2009).
Major et al., Characterisation and Phase Behaviour of Phospholipid Bilayers Adsorbed on Spherical Polysaccharidic Nanoparticles. Biochimica et Biophysica Acta, 1997, 1327, 32-40.
Mangsbo et al., Enhanced tumor eradication by combining CTLA-4 or PD-1 blockade with CpG therapy. J Immunother. Apr. 2010;33(3):225-35. doi: 10.1097/CJI.0b013e3181c01fcb.
Marshall et al., Novel chimeric immunomodulatory compounds containing short CpG oligodeoxyribonucleotides have differential activities in human cells. Nucleic Acids Res. Sep. 1, 2003;31(17):5122-33.
Martin et al., Ein neur Zugang zu 2'-O-alkyhibonucleosiden and Eigenschaften deren oligonucleotide Hely, Chim. Acta, 78:486-504 (1995).
Martinson et al., Impact of class A, B and C CpG-oligodeoxynucleotides on in vitro activation of innate immune cells in human immunodeficiency virus-1 infected individuals. Immunology. (2007) 120(4):526-35.
Massich et al., Regulating immune response using polyvalent nucleic acid-gold nanoparticle conjugates. Mol Pharm. Nov.-Dec. 2009;6(6):1934-40.
Matsunaga et al., Biomagnetic Nanoparticle Formation and Application. Supramolecular Science, 1998, 5 (3-4), 391-394.
Mcallister et al., Polymeric nanogels produced via inverse microemulsion polymerization as potential gene and antisense delivery agents, J. Am. Chem. Soc., 124:15198 (2002).
Mcbain et al., Polyethyleneimine Functionalized Iron Oxide Nanoparticles as Agents for DNA Deliver and Transfection. J. Mater. Chem., 2007, 17, 2561-2565.

(56) References Cited

OTHER PUBLICATIONS

Medintz et al., A reactive peptidic linker for self-assembling hybrid quantum dot-DNA bioconjugates. Nano Lett. Jun. 2007;7(6):1741-8. Epub May 26, 2007.
Mehta et al., Topical and transdermal delivery: What a pharmacist needs to know. InetCE. Jul. 2004:1-10.
Ming et al., Albumin-based nanoconjugates for targeted delivery of therapeutic oligonucleotides. Biomaterials. Oct. 2013;34(32):7939-49. doi:10.1016/j.biomaterials.2013.06.066. Epub Jul. 19, 2013.
Mirkin et al., A DNA-based method for rationally assembling nanoparticles into macroscopic materials, Nature, 382:607-9 (1996).
Mui et al., Immune stimulation by a CpG-containing oligodeoxynucleotide is enhanced when encapsulated and delivered in lipid particles. J Pharmacol Exp Ther. Sep. 2001;298(3):1185-92.
Munde et al., Induced fit conformational changes of a "reversed amidine" heterocycle: optimized interactions in a DNA minor groove complex. J Am Chem Soc. May 2, 2007;129(17):5688-98. Epub Apr. 11, 2007.
Pan et al., Dendrimer-Modified Magnetic Nanoparticles Enhance Efficiency of Gene Delivery System. Cancer Res. 2007;67:8156-8163.
Patil et al., Evidence for Novel Interdigitated Bilayer Formation of Fatty Acids During Three-Dimensional Self-Assembly on Silver Colloidal Particles. J. Am. Chem. Soc., 1997, 119 (39), 9281-9282.
Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.
Pearson et al., Polynucleotide Binding to Macrophage Scavenger Receptors Depends on the Formation of Base-quartet-stabilized Four-stranded Helices. JBC, VOi. 268, No. 5, Issue of Feb. 15. pp. 3546-3554, 1993 (Year: 1993).
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Pfeiffer et al., Bivalent Cholesterol-Based Coupling of Oligonucleotides to Lipid Membrane Assemblies. J. Am. Chem. Soc. 2004;126:10224-10225.
Pfeiffer et al., Quantification of oligonucleotide modifications of small unilamellar lipid vesicles. Anal. Chem. 2006;78:7493-8.
Phan, Human telomeric G-quadruplex: structures of DNA and RNA sequences. FEBS J. Mar. 2010;277(5):1107-17. doi: 10.1111/j.1742-4658.2009.07464.x. Epub; Nov. 27, 2009.
Plant et al., Self-assembled phospholipid/alkanethiol biomimetic bilayers on gold. Langmuir. 1993;9:2764-7.
Platt al., Role for the class A macrophage scavenger receptor in the phagocytosis of apoptotic thymocytes in vitro. Proc Natl Acad Sci U S A. Oct. 29, 1996;93(22):12456-60.
Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Ramos-Casals et al., Autoimmune diseases induced by TNF-targeted therapies: analysis of 233 cases. Medicine (Baltimore). Jul. 2007;86(4):242-51.
Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Romanucci et al., Synthesis, biophysical characterization and anti-HIV activity of d(TG3AG) Quadruplexes bearing hydrophobic tails at the 5'-end. Bioorg Med Chem. Feb. 1, 2014;22(3):960-6. doi: 10.1016/j.bmc.2013.12.051. Epub Jan. 4, 2014.
Rosenzweig et al., Self-assembly of a four-helix bundle on a DNA quadruplex. Angew Chem Int Ed Engl. 2009;48(15):2749-51. doi:10.1002/anie.200804849.
Rosi et al., Oligonucleotide-modified gold nanoparticles for intracellular gene regulation. Science. May 19, 2006;312(5776):1027-30.
Schieren et al., Comparison of large unilamellar vesicles prepared by a petroleum ether vaporization method with multilamellar vesicles: ESR, diffusion and entrapment analyses. Biochim Biophys Acta. Aug. 3, 1978;542(1):137-53.
Schwab et al., An approach for new anticancer drugs: Oncogene-targered antisense DNA. Ann Oncol. 1994;5(Suppl4):S55-8.
Sen et al., Formation of parallel four-stranded complexes by guanine-rich motifs in DNA and its implications; for meiosis. Nature, 1988, 334:364-366.
Senior et al., Stability of small unilamellar liposomes in serum and clearance from the circulation: the effect of the phospholipid and cholesterol components, Life Sci. 30:2123 (1982).
Shahzad et al., Targeted delivery of small interfering RNA using reconstituted high-density lipoprotein nanoparticles. Neoplasia. Apr. 2011;13(4):309-19.
Shukla et al., Development of streptavidin-based ; nanocomplex for siRNA delivery. Mol Pharm. Dec. 2, 2013;10(12):4534-45. doi:; 10.1021/mp400355q. Epub Oct. 25, 2013.
Shukoor et al., CpG-DNA loaded multifunctional MnO nanoshuttles for TLR9-specific cellular cargo delivery, selective immune-activation and MRI. J. Mater. Chem., 2012,22, 8826-8834.
Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. doi: 10.1016/j.biomaterials.2010.03.067. Epub Apr. 24, 2010.
Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nltid=164032911.
Stengel et al., Determinants for Membrane Fusion Induced by Cholesterol-Modified DNA Zippers, J. Phys. Chem. B., 112:8264-74 (2008).
Sulkowski et al., The influence of temperature, cholesterol content and pH on liposome stability, J. Mol. Struct., 744-747: 737 (2005).
Tiwari et al., Functionalized gold nanoparticles and their biomedical applications. Nanomaterials. 2011;1:31-63. doi: 10.3390/nano1010031.
Toh et al. Liposomes as sterile preparations and limitations of sterilisation techniques in liposomal manufacturing, Asian Journal of Pharmaceutical Sciences (2013) 8(2):88-95.
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
Versluis et al., In situ modification of plain liposomes with lipidated coiled coil forming peptides induces membrane fusion, J. Am. Chem. Soc.. 135:8057 (2013).
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Wang et al., Simplified Textbook on Molecular Biology. Jul. 31, 2008:p. 15.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
Whitehead et al., Knocking down barriers: advances in siRNA delivery, Nat. Rev. Drug. Discov., 8:129 (2009).
Willis et al., Liposome-Anchored Vascular Endothelial Growth Factor Aptamers, Biocon. Chem., 9:573-82 (1998).
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Wilton et al. Antisense oligonucleotide-induced exon skipping across the human dystrophin gene transcript. Mol Ther. Jul. 2007;15(7):1288-96. Epub Feb. 6, 2007.
Wolfe et al., Modulation of Tetraplex Formation by Chemical Modifications of a G4-Containing Phosphorothioate Oligonucleotide. J. Am. Chem. Soc. 1996, 118, 6301-6302 (Year: 1996).
Wolfrum et al., Mechanisms and optimization of in vivo delivery of lipophilic siRNAs. Nat Biotechnol. Oct. 2007;25(10):1149-57. Epub Sep. 16, 2007.

(56) References Cited

OTHER PUBLICATIONS

Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Xiao et al., Mannosylated bioreducible nanoparticle-mediated macrophage-specific TNF-RNA interference for IBD therapy. Biomaterials. Oct. 2013;34(30):7471-82. doi: 10.1016/j.biomaterials.2013.06.008. Epub Jun. 29, 2013.
Xing et al., Selective delivery of an anticancer drug with aptamer-functionalized liposomes to breast cancer cells in vitro and in vivo, J. Mater. Chem. B., 1:5288 (2013).
Yang et al., Experimental technologies of biochemistry and molecular biology. Higher Ed Press of China. Jun. 30, 2008. p. 168.
Yang et al., Inhibition of a C-rich oligodeoxynucleotide on activation of immune cells in vitro and enhancement of antibody response in mice. Immunology. Dec. 2010;131(4):501-12. doi: 10.1111/j.1365-2567.2010.03322.x.
Yin et al., Supramolecular self-assembled nanoparticles mediate oral delivery of therapeutic TNF-siRNA against systemic inflammation. Angew Chem Int Ed Engl. May 27, 2013;52(22):5757-61. doi: 10.1002/anie.201209991. Epub Apr. 22, 2013.
Young et al., Hollow spherical nucleic acids for intracellular gene regulation based upon biocompatible silica shells, Nano Lett., 12:3867 (2012).
Zhang et al., A general approach to DNA-programmable atom equivalents. Nat Mater. Aug. 2013;12(8):741-6. doi: 10.1038/nmat3647. Epub May 19, 2013.
Zhang et al., Antibody-linked spherical nucleic acids for cellular targeting, J. Am. Chem. Soc., 134:16488-91 (2012).
Zhang et al., Nanopod formation through gold nanoparticle templated and catalyzed crosslinking of polymers bearing pendant propargyl ethers. J Am Chem Soc. Nov. 3, 2010;132(43):15151-3.
Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.
Zhang et al., Structure-activity relationships of cationic shell-crosslinked knedel-like nanoparticles: shell composition and transfection efficiency/cytotoxicity, Biomaterials, 31:1805 (2010).
Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.
[No Author Listed] Introducing Antisense Oligonucleotides into Cells, Innovation & Precision in Nucleic Acid Synthesis, Integrated DNA Technologies. 2005.pp. 1-7.
Auyeung et al., Synthetically programmable nanoparticle superlattices using a hollow threedimensional spacer approach. Nat Nanotechnol 7(1 ):24-28 (2012).
Calabrese et al., Biocompatible infinite-coordination-polymer nanoparticle-nucleic-acid conjugates for antisense gene regulation. Angew Chem Int Ed Engl. Jan. 7, 2015;54(2):476-480. Doi: 10.1002/anie.201407946. Epub Nov. 13, 2014.
Combadiere et al., Particle-based vaccines for transcutaneous vaccination. Comp Immunol Microbiol Infect Dis. Mar. 2008;31(2-3):293-315. Epub Oct. 30, 2007. Review.
Cui et al., Topical immunization using nanoengineered genetic vaccines. J Control Release. May 17, 2002;81(1-2):173-84.
Debouttiere et al., Design of Gold Nanoparticles for Magnetic Resonance Imaging. Adv Funct Mater. Dec. 2006;16(18): 2330-9.
Deering et al., Nucleic acid vaccines: prospects for non-viral delivery of mRNA vaccines. Expert Opin Drug Deliv. Jun. 2014;11(6):885-99. Doi: 10.1517/17425247.2014.901308. Epub Mar. 26, 2014. Review.

Eckstein, Oligonucleotides and Analogues, $1^{st}$ Ed. (Oxford University Press, New York) (1991). Table of contents, pp. ix-xvii.
Hames et al. (eds.) Genes Probes. New York. IRL Press. 1995. Table of Contents, pp: ix-xiv.
Hayat (ed). Colloidal Gold. Principles, Methods and Applications. Academic Press, San Diego. 1989. vol. 1. Table of Contents, pp. v.-xvii.
Hayat (ed). Colloidal Gold. Principles, Methods and Applications. Academic Press, San Diego. 1989. vol. 2. Table of Contents, pp. v.-xix.
Hayat (ed). Colloidal Gold. Principles, Methods and Applications. Academic Press, San Diego. 1991. vol. 3. Table of Contents, pp. v.-xiv.
Hill et al., "Controlling the Lattice Parameters of Gold Nanoparticle FCC Crystals with Duplex DNA Linkers," Nano Lett 8(8): 2341-2344 (2008).
Li et al., A Calcium-Sensitive Magnetic Resonance Imaging Contrast Agent. JACS. 1999;121(6):1413-4.
Luo et al., Synthetic DNA delivery systems. Nat Biotechnol. Jan. 2000;18(1):33-7.
Mayer (ed)., Nucleic Acid and Peptide Aptamers: Methods and Protocols (Humana Press, 2009). Entire book. Table of Contents, pp. 1-406.
Modo et al., (eds)., Molecular and Cellular MR Imaging. Florida: CRC Press (2007). Table of Contents, pp. 1-4.
Opalinska et al., Nucleic-acid therapeutics: basic principles and recent applications. Nat Rev Drug Discov. Jul. 2002;1(7):503-14.
Patil et al., Temozolomide delivery to tumor cells by a multifunctional nano vehicle based on poly(β-L-malic acid). Pharm Res. Nov. 2010;27(11):2317-29. Doi: 10.1007/s11095-010-0091-0. Epub Apr. 13, 2010.
Sambrook et al., Molecular Cloning: A Laboratory Manual, $2^{nd}$ Ed. 1999. Table of Contents, pp. v-xxxii.
Schmid (ed), Clusters and Colloids (VCH Weinham, 1994). Table of Contents, pp. v-xi.
Seeman, An Overview of Structural DNA Nanotechnology. Mol Biotechnol 37(3): 246-257 (2007).
Watson et al., (Eds). Molecular Biology of the Gene, $4^{th}$ Ed. The Benjamin Cummins Publishing Company, Inc. 1987. Table of Contents, x-xxix.
Wu et al., Intracellular fate of spherical nucleic acid nanoparticle conjugates. J Am Chem Soc. May 28, 2014;136(21):7726-33. doi: 10.1021/ja503010a. Epub May 19, 2014.
Zhang et al., "A general strategy for the DNA-mediated self-assembly of functional nanoparticles into heterogeneous systems," Nat Nanotechnol 8(11): 865-872 (2013).
U.S. Appl. No. 15/502,955, filed Feb. 9, 2017, Mirkin et al.
U.S. Appl. No. 16/611,502, filed Nov. 7, 2019, Mirkin et al.
U.S. Appl. No. 16/611,548, filed Nov. 7, 2019, Mirkin et al.
U.S. Appl. No. 16/160,196, filed Oct. 15, 2018, Mirkin et al.
U.S. Appl. No. 16/328,025, filed Feb. 25, 2019, Mirkin et al.
U.S. Appl. No. 16/242,704, filed Jan. 8, 2019, Mirkin et al.
U.S. Appl. No. 17/011,658, filed Sep. 3, 2020, Mirkin et al.
[No Author Listed], Modern Pharmaceutical Design. 2006. Chapter 5. p. 273. Summary. 2 pages.
Berton et al., Highly loaded nanoparticulate carrier using an hydrophobic antisense oligonucleotide complex. Eur. J. Pharma. Sci. 1999;9:163-70.
Chung et al., Nuclease-resistant DNA aptamer on gold nanoparticles for the simultaneous detection of Pb2+ and Hg2+ in human serum, Biosens. Bioelectron. 41 :827-32 (2013).
Cui et al., Exploration of the Structure and Recognition of a G-quadruplex in the her2 Proto-oncogene Promoter and Its Transcriptional Regulation. Sci Rep. Mar. 8, 2019;9(1):3966. doi: 10.1038/s41598-019-39941-5.
Demesmaeker et al., Antisense oligonucleotides. Acc. Chem. Res. 1995;28(9): 366-74.
Holen et al., Positional effects of short interfering RNAs targeting the human coagulation trigger tissue factor. Nucl. Acids Res. 2002;30: 1757-66.
Hong et al., Directed Assembly of Nucleic Acid-Based Polymeric Nanoparticles from Molecular Tetravalent Cores, *J. Am. Chem. Soc.* 137:8184-91 (2015).

(56) References Cited

OTHER PUBLICATIONS

Hsu et al., Delivery of siRNA and other macromolecules into skin and cells using a peptide enhancer. Proc Natl Acad Sci USA. 2011;108(38):15816-15821. doi:10.1073/pnas.1016152108.

Jeong et al., Novel intracellular delivery system of antisense oligonucleotide by self-assembled hybrid micelles composed of DNA/PEG conjugate and cationic fusogenic peptide. Bioconjugate Chem. 2003;14: 473-9.

Liu et al., New poly(d-glucaramidoamine)s induce DNA nanoparticle formation and efficient gene delivery into mammalian cells. J. Am. Chem. Soc. 2004;126: 7422-3.

Miller et al., Antisense oligonucleotides: Strategies for delivery. PSTT. 1998;1(9): 377-86.

Mucic et al., Synthesis and characterization of DNA with ferrocenyl groups attached to their 5'-termini: electrochemical characterization of a redox-active nucleotide monolayer. Chem. Comm. 1996;555-7.

Ogloblina et al., Parallel G-Quadruplexes Formed by Guanine-Rich Microsatellite Repeats Inhibit Human Topoisomerase I. Biochemistry (Mosc). Aug. 2015;80(8):1026-38. doi: 10.1134/S0006297915080088.

Patil et al., DNA-based therapeutics and DNA delivery systems: a comprehensive review. AAPS J., 2005;7(1): E61-77.

Rajur et al., Covalent protein-oligonucleotide conjugates for efficient delivery of antisense molecules. Bioconjug Chem. Nov.-Dec. 1997;8(6):935-40. doi: 10.1021/bc970172u.

Sun et al., Multidimensional sensor for pattern recognition of proteins based on DNA-gold nanoparticles conjugates, Anal. Chem. Mar. 17, 2015;87(6):3354-9.

Wei et al., A study of the relationships between oligonucleotide properties and hybridization signal intensities from NimbleGen microarray datasets. Nucl. Acids Res., 2008;36: 2926-38.

Wolfe et al., RNA G-quadruplexes cause eIF4A-dependent oncogene translation in cancer. Nature. Sep. 4, 2014;513(7516):65-70. doi: 10.1038/nature13485. Epub Jul. 27, 2014.

\* cited by examiner

| Oligonucleotide (5' → 3') | Loading (ssDNA/NP) |
|---|---|
| $A_{30}$-SH | 45 ± 4 |
| $T_{30}$-SH | 184 ± 1 |
| $(CCT)_{10}$-SH | 140 ± 4 |
| $(GGT)_{10}$-SH | 74 ± 1 |

| | Name of SNA | Sequence of constituent oligonucleotides (5' → 3') |
|---|---|---|
| SEQ ID NO: 29 | Cy5-A$_{30}$ | Cy5-AAAAAAAAAAAAAAAAAAAAAAAAAAAAAA - propylthiol |
| SEQ ID NO: 30 | Cy5-T$_{30}$ | Cy5-TTTTTTTTTTTTTTTTTTTTTTTTTTTTTT - propylthiol |
| SEQ ID NO: 31 | Cy5-(CCT)$_{10}$ | Cy5-CCTCCTCCTCCTCCTCCTCCTCCTCCTCCT - propylthiol |
| SEQ ID NO: 32 | Cy5-(GGT)$_{10}$ | Cy5-GGTGGTGGTGGTGGTGGTGGTGGTGGTGGT - propylthiol |

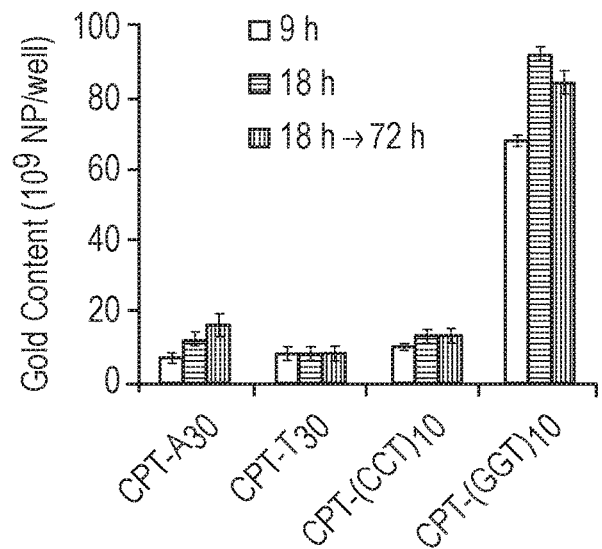
Figure 8B
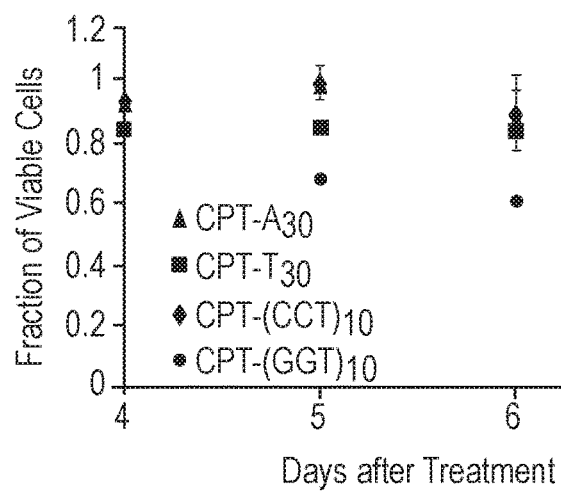
Figure 8C
Figure 8E
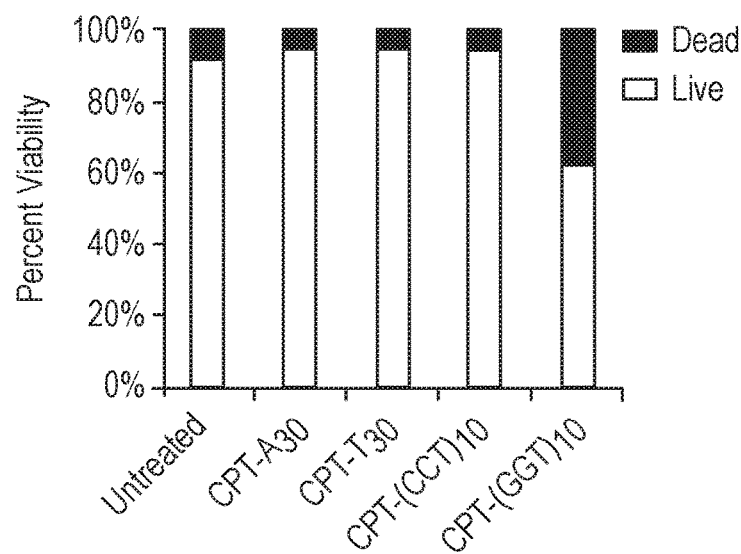
Figure 8F

|  | DNA-SH<br>MW (g/mol) | DBCO-DNA-SH<br>MW (g/mol) | CPT-DNA-SH<br>MW (g/mol) |
|---|---|---|---|
| $A_{30}$ | 9574 | 10137 | 10628 |
| $T_{30}$ | 9303 | 9867 | 10353 |
| $(CCT)_{10}$ | 8995 | 9568 | 10055 |
| $(GGT)_{10}$ | 9807 | 10373 | 10862 |

*Figure 9C*

| Type of SNA | Sequence of constituent DNA oligonucleotides (5'→ 3') |
|---|---|
| CPT-poly A SNA | CPT - AAAAAAAAAAAAAAAAAAAAAAAAAAAAAA - propylthiol |
| CPT-poly T SNA | CPT - TTTTTTTTTTTTTTTTTTTTTTTTTTTTTT - propylthiol |
| CPT-poly C SNA | CPT - CCTCCTCCTCCTCCTCCTCCTCCTCCTCCT - propylthiol |
| CPT-poly G SNA | CPT - GGTGGTGGTGGTGGTGGTGGTGGTGGTGGT - propylthiol |

*Figure 9D*

SEQUENCE LISTING

```
<160> NUMBER OF SEQ ID NOS: 32

<210> SEQ ID NO 1
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 1
aaaaaaaaaa aaaaaaaaaa aaaaaaaaaa                                      30

<210> SEQ ID NO 2
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 2
tttttttttt tttttttttt tttttttttt                                      30
```

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 3
cctcctcctc ctcctcctcc tcctcctcct                                30

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 4
ggtggtggtg gtggtggtgg tggtggtggt                                30

<210> SEQ ID NO 5
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(28)
<223> OTHER INFORMATION: DCBO

<400> SEQUENCE: 5
ggtggtggtg gtggtttttt tttttttt                                  28

<210> SEQ ID NO 6
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(28)
<223> OTHER INFORMATION: DCBO

<400> SEQUENCE: 6
tatcgtattt actctgattt tttttttt                                  28

<210> SEQ ID NO 7
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(28)
<223> OTHER INFORMATION: DCBO

<400> SEQUENCE: 7
ggtggtggtg gtggtttttt tttttttt                                  28

```
<210> SEQ ID NO 8
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (28)..(28)
<223> OTHER INFORMATION: DBCO

<400> SEQUENCE: 8
tatcgtattt actctgattt tttttttt                                          28

<210> SEQ ID NO 9
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 9
ggtggttttt tttttttttt tttttttttt                                        30

<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 10
ggtggtggtg gttttttttt tttttttttt                                        30

<210> SEQ ID NO 11
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 11
ggtggtggtg gtggtggttt tttttttttt                                        30

<210> SEQ ID NO 12
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 12
```
ggtggtggtg gtggtggtgg tggttttttt                                            30

<210> SEQ ID NO 13
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 13
tttttttttt ttggtggttt tttttttttt                                            30

<210> SEQ ID NO 14
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: propylthiol

<400> SEQUENCE: 14
tttttttttt ttggtggtgg tggttttttt                                            30

<210> SEQ ID NO 15
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: d = abasic site with both ribose unit and
      phosphate backbone
<220> FEATURE:
<221> NAME/KEY: misc_feature
<222> LOCATION: (30)..(30)
<223> OTHER INFORMATION: propylthiol

<400> SEQUENCE: 15
dddddttttt tttttttttt tttttttttt                                            30

<210> SEQ ID NO 16
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: d = abasic site with both ribose unit and
      phosphate backbone
<220> FEATURE:
<221> NAME/KEY: misc_feature
<222> LOCATION: (30)..(30)
<223> OTHER INFORMATION: propylthiol

<400> SEQUENCE: 16
dddddddddd tttttttttt tttttttttt                                            30

<210> SEQ ID NO 17
<211> LENGTH: 30
<212> TYPE: DNA
<213> ORGANISM: Artificial Sequence

```
<220> FEATURE:
<223> OTHER INFORMATION: Synthetic Oligonucleotide
<220> FEATURE:
<221> NAME/KEY: misc_feature
<223> OTHER INFORMATION: d = abasic site with both ribose unit and
      phosphate backbone
<220> FEATURE:
<221> NAME/KEY: misc_feature
<222> LOCATION: (30)..(30)
<223> OTHER INFORMATION: propylthiol

<400> SEQUENCE: 17
dddddddddd dddddttttt tttttttttt                                           30

<210> SEQ ID NO 18
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: d = abasic site with both ribose unit and
      phosphate backbone
<220> FEATURE:
<221> NAME/KEY: misc_feature
<222> LOCATION: (30)..(30)
<223> OTHER INFORMATION: propylthiol

<400> SEQUENCE: 18
dddddddddd dddddddddd tttttttttt                                           30

<210> SEQ ID NO 19
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: abasic site with the phosphate backbone only
<220> FEATURE:
<221> NAME/KEY: misc_feature
<223> OTHER INFORMATION: c = abasic site with the phosphate backbone
      only
<220> FEATURE:
<221> NAME/KEY: misc_feature
<222> LOCATION: (30)..(30)
<223> OTHER INFORMATION: propylthiol

<400> SEQUENCE: 19
cccccttttt tttttttttt tttttttttt                                           30

<210> SEQ ID NO 20
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: c = abasic site with the phosphate backbone
      only
<220> FEATURE:
<221> NAME/KEY: misc_feature
<222> LOCATION: (30)..(30)
<223> OTHER INFORMATION: propylthiol

<400> SEQUENCE: 20
cccccccccc tttttttttt tttttttttt                                           30
```

```
<210> SEQ ID NO 21
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: c = abasic site with the phosphate backbone
      only
<220> FEATURE:
<221> NAME/KEY: misc_feature
<222> LOCATION: (30)..(30)
<223> OTHER INFORMATION: propylthiol

<400> SEQUENCE: 21
cccccccccc ccccctttttt tttttttttt                                   30

<210> SEQ ID NO 22
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: c = abasic site with the phosphate backbone
      only
<220> FEATURE:
<221> NAME/KEY: misc_feature
<222> LOCATION: (30)..(30)
<223> OTHER INFORMATION: propylthiol

<400> SEQUENCE: 22
cccccccccc cccccccccc tttttttttt                                    30

<210> SEQ ID NO 23
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: CPT
<220> FEATURE:
<221> NAME/KEY: misc_feature
<222> LOCATION: (30)..(30)
<223> OTHER INFORMATION: propylthiol

<400> SEQUENCE: 23
aaaaaaaaaa aaaaaaaaaa aaaaaaaaaa                                    30

<210> SEQ ID NO 24
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: CPT
<220> FEATURE:
<221> NAME/KEY: misc_feature
<222> LOCATION: (30)..(30)
<223> OTHER INFORMATION: propylthiol

<400> SEQUENCE: 24
tttttttttt tttttttttt tttttttttt                                    30
```

```
<210> SEQ ID NO 25
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: CPT
<220> FEATURE:
<221> NAME/KEY: misc_feature
<222> LOCATION: (30)..(30)
<223> OTHER INFORMATION: propylthiol

<400> SEQUENCE: 25
cctcctcctc ctcctcctcc tcctcctcct                                30

<210> SEQ ID NO 26
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: CPT
<220> FEATURE:
<221> NAME/KEY: misc_feature
<222> LOCATION: (30)..(30)
<223> OTHER INFORMATION: propylthiol

<400> SEQUENCE: 26
ggtggtggtg gtggtggtgg tggtggtggt                                30

<210> SEQ ID NO 27
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 27
tttttttttt ttggtggttt tttttttttt                                30

<210> SEQ ID NO 28
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 28
tttttttttt ttggtggtgg tggttttttt                                30

<210> SEQ ID NO 29
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy5 Fluorophore
<220> FEATURE:
<221> NAME/KEY: misc_feature
<222> LOCATION: (30)..(30)
<223> OTHER INFORMATION: Propylthiol
```

```
<400> SEQUENCE: 29
aaaaaaaaaa aaaaaaaaaa aaaaaaaaaa                                              30

<210> SEQ ID NO 30
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy5 Fluorophore
<220> FEATURE:
<221> NAME/KEY: misc_feature
<222> LOCATION: (30)..(30)
<223> OTHER INFORMATION: propylthiol

<400> SEQUENCE: 30
tttttttttt tttttttttt tttttttttt                                              30

<210> SEQ ID NO 31
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy5 Fluorophore
<220> FEATURE:
<221> NAME/KEY: misc_feature
<222> LOCATION: (30)..(30)
<223> OTHER INFORMATION: Propylthiol

<400> SEQUENCE: 31
cctcctcctc ctcctcctcc tcctcctcct                                              30

<210> SEQ ID NO 32
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cy5 Fluorophore
<220> FEATURE:
<221> NAME/KEY: misc_feature
<222> LOCATION: (30)..(30)
<223> OTHER INFORMATION: Propylthiol

<400> SEQUENCE: 32
ggtggtggtg gtggtggtgg tggtggtggt                                              30
```

SEQUENCE-SPECIFIC CELLULAR UPTAKE OF SPHERICAL NUCLEIC ACID NANOPARTICLE CONJUGATES

CROSS REFERENCE TO RELATED APPLICATIONS

This application is a U.S. National Phase of International Application No. PCT/US15/062005 filed Nov. 20, 2015, which claims the priority benefit under 35 U.S.C. § 119(e) of U.S. Provisional Application No. 62/083,092, filed Nov. 21, 2014, the disclosure of which is incorporated herein by reference in their entirety.

STATEMENT OF GOVERNMENT INTEREST

This invention was made with government support under grant number FA9550-11-1-0275 awarded by the Air Force Office of Scientific Research; and grant numbers U54 CA151880 and U54 CA159341 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 2014-183_Seqlisting.txt; 10,070 bytes, created Nov. 20, 2015.

FIELD OF THE INVENTION

The present disclosure is directed to spherical nucleic acid (SNA) nanoparticles surface-functionalized with a polynucleotide and a nucleotide sequence that affects the uptake of the SNA nanoparticle by a cell.

BACKGROUND

Spherical nucleic acid nanoparticle conjugates (SNAs) are a class of bionanomaterials that exhibit fundamentally different properties compared to linear nucleic acids. SNAs are composed of highly oriented oligonucleotide strands that are densely packed onto the surface of a nanoparticle core [Cutler et al., J Am Chem Soc 134: 1376-1391 (2012)]. Unlike single-stranded DNAs, SNAs can naturally enter mammalian cells without the aid of cationic or lipophilic transfection agents despite their high negative charge [Rosi et al., Science 312: 1027-1030 (2006)]. The robust cellular uptake properties of SNAs offer the potential for the development of intracellular diagnostic [Seferos et al., J Am Chem Soc 129: 15477-15479 (2007)] and gene regulation [Giljohann et al., J Am Chem Soc 131: 2072-2073 (2009)] tools without the toxicity or immune responses traditionally associated with cationic or lipophilic agents [Massich et al., Mol Pharm 6: 1934-1940 (2009)]. Indeed, the ability of SNAs to regulate genes of interest in vitro and in vivo has been demonstrated [Zheng et al., Proc Natl Acad Sci U.S.A. 109: 11975-11980 (2012); Jensen et al., Sci Transl Med 5, 209ra152 (2013)].

Mechanistic studies have identified class A scavenger receptors (SR-A) as the primary cellular receptors responsible for the recognition of such structures, and the binding of SNAs to SR-A leads to caveolae-mediated endocytosis [Choi et al., Proc Natl Acad Sci U.S.A. 110: 7625-7630 (2013)]. Linear nucleic acids enriched in guanylic acid (G) are naturally recognized by SR-A, which has been proposed to be due to their ability to fold into secondary structures known as G-quadruplexes [Pearson et al., J Biol Chem 268: 3546-3554 (1993)]. In contrast, linear polymers of adenylic acid (A), thymidylic acid (T), and cytidylic acid (C) do not fold into secondary structures that are recognized by SR-A, and as such, they are not natural ligands [Pearson et al., J Biol Chem 268: 3546-3554 (1993)].

SUMMARY OF THE INVENTION

Due to their multivalent architecture, the cellular interaction of SNAs is dependent not only on size of the nanostructure, but also on ligand presentation [Giljohann et al., Nano Lett 7: 3818-3821 (2007)]. Without being bound to theory, it is contemplated that SNAs are able to enter cells without ancillary transfection agents because the SNA architecture mimics this secondary structure formation. Additionally, the present disclosure provides that oligonucleotide sequence plays an important role in the interaction of SNAs with SR-A and subsequent cellular uptake.

Accordingly, provided herein is a nanoparticle functionalized with a polynucleotide and a domain, the domain (i) situated at the terminus of the polynucleotide that is distal to the nanoparticle and (ii) comprising a nucleotide sequence that is at least 50% but less than 100% guanylic acid. In some embodiments, the domain is located at the 5' terminus of the polynucleotide. In further embodiments, the domain is located at the 3' terminus of the polynucleotide. In still further embodiments, the domain is located at an internal region within the polynucleotide. The domain, in various embodiments, is from about 2 to about 50 nucleotides in length. In some embodiments, the polynucleotide is DNA. In further embodiments, the polynucleotide is RNA. In still further embodiments, the domain comprises at least three (GGX) motifs. In some embodiments, X is a deoxyribonucleotide or a ribonucleotide. In some embodiments, X is adenylic acid, thymidylic acid, uridylic acid, or cytidylic acid. In some embodiments, X is guanylic acid. In some embodiments, X is not guanylic acid. In further embodiments, X is a modified nucleotide.

In some embodiments, the nanoparticle is functionalized with an additional polynucleotide. In further embodiments, the additional polynucleotide comprises a domain. In some embodiments, the additional polynucleotide is DNA. In further embodiments, the additional polynucleotide is RNA.

In various embodiments, the domain comprises a poly guanylic acid (poly G) nucleotide sequence comprising more than one guanylic acid. In further embodiments, the domain comprises a poly guanylic acid (poly G) sequence comprising two, three, four, five, six, seven, eight, nine, ten, eleven, twelve, thirteen, fourteen, fifteen, sixteen, seventeen, eighteen, nineteen, or twenty guanylic acid nucleotides.

In some aspects, the disclosure also provides a method of increasing cellular uptake of a polynucleotide-functionalized nanoparticle comprising the step of modifying the nanoparticle to further comprise a domain that increases cellular uptake of the oligonucleotide-functionalized nanoparticle compared to the polynucleotide-functionalized nanoparticle lacking the domain. In some embodiments, the domain comprises a poly guanylic acid (poly G) nucleotide sequence comprising more than one guanylic acid. In further embodiments, the domain comprises a poly G sequence comprising two, three, four, five, six, seven, eight, nine, ten, eleven, twelve, thirteen, fourteen, fifteen, sixteen, seventeen, eighteen, nineteen, or twenty guanylic acid nucleotides. In some embodiments, the domain is located at the 5' terminus of the polynucleotide. In some embodiments, the domain is located at the 3' terminus of the polynucleotide. In still further embodiments, the domain is located at an internal region within the polynucleotide. In some embodiments, the domain is colinear with the polynucleotide. In various embodiments, the polynucleotide is DNA. In some embodiments, the polynucleotide is RNA.

It is contemplated that any of the methods of the disclosure are performed with a polynucleotide-functionalized nanoparticle as disclosed herein.

In further aspects of the disclosure, a nanoparticle functionalized with a polynucleotide is provided, wherein the distal end of the polynucleotide terminates in a sequence comprising at least three (GGX) motifs. In some embodiments, the at least three (GGX) motifs are located on the 5' end of the polynucleotide. In further embodiments, the at least three (GGX) motifs are located on the 3' end of the polynucleotide. In some embodiments, X is a deoxyribonucleotide, and in further embodiments, X is a ribonucleotide. In still further embodiments, X is adenylic acid, thymidylic acid, uridylic acid, or cytidylic acid. It is also contemplated by the disclosure that in some embodiments, X is a modified nucleotide.

In various embodiments, the nanoparticle is functionalized with an additional polynucleotide. In some embodiments, the polynucleotide and/or the additional polynucleotide is DNA. In further embodiments, the polynucleotide and/or the additional polynucleotide is RNA. In still further embodiments, the polynucleotide and/or the additional polynucleotide is siRNA.

In any of the aspects or embodiments of the disclosure, the SNA has a net negative charge.

In some aspects, the disclosure provides a method of increasing cellular uptake of a polynucleotide-functionalized nanoparticle comprising the step of modifying the polynucleotide such that the distal end of the polynucleotide (i.e., the end opposite the end that is functionalized to the nanoparticle) terminates in a sequence comprising at least three (GGX) motifs, wherein uptake of the polynucleotide-functionalized nanoparticle comprising the modification is increased compared to a polynucleotide-functionalized nanoparticle lacking the modification. In some embodiments, the at least three (GGX) motifs are located on the 5' end of the polynucleotide. In further embodiments, the at least three (GGX) motifs are located on the 3' end of the polynucleotide. In additional embodiments, the nanoparticle is functionalized with an additional polynucleotide. In related embodiments, the polynucleotide and/or the additional polynucleotide is DNA. In some embodiments, the polynucleotide and/or the additional polynucleotide is RNA. In further embodiments, the polynucleotide and/or the additional polynucleotide is siRNA. In some embodiments, the cell is a prokaryotic cell. In further embodiments, the cell is a eukaryotic cell. In related embodiments, the eukaryotic cell is a human cell.

The disclosure also provides methods, in some embodiments, wherein the polynucleotide comprises a sequence sufficiently complementary to a target polynucleotide sequence to hybridize to the target polynucleotide sequence under appropriate conditions. In further embodiments, the additional polynucleotide comprises a sequence sufficiently complementary to a target polynucleotide sequence to hybridize to the target polynucleotide sequence under appropriate conditions. In related embodiments, the hybridizing results in detection of the target polynucleotide. In still further embodiments, the hybridizing results in inhibition of target gene expression.

BRIEF DESCRIPTION OF THE FIGURES

FIGS. 8a-8f depict delivery of camptothecin molecules using CPT-SNAs. 8a) The —OH group of the camptothecin molecule (CPT) is modified by a short bifunctional linker to form camptothecin azide (CPT-N3) by literature precedent [Parrish et al., Bioconjugate Chem. 18: 263-267 (2006)]. CPT-N3 is then coupled to dibenzocyclooctyl-DNA-thiol (DBCO-DNA-SH) by copper-free click chemistry to form camptothecin-DNA-thiol (CPT-DNA-SH). DCC=N'N'-dicyclohexocarbodiimide, DMAP=4-dimethylaminopyridine, $CH_2Cl_2$=dichloromethane, DMSO=dimethyl sulfoxide. 8b) Measurements based on the fluorescence emission of CPT at 440 nm revealed that CPT-SNAs of all four nucleobase types contain 55±15 CPT molecules per particle. 8c) By ICP-MS analysis of the gold content of the A549 cells treated with CPT-SNAs, CPT-poly G SNAs can enter cells in highest quantities among all nucleobase types tested. The CPT-SNAs (at least the AuNP core) do not seem to leave the cells after the treatment. Error bars denote the standard deviation from triplicate measurements. 8d) By confocal imaging, CPT-poly G SNAs can deliver CPT molecules (green) into A549 cells in highest quantities among CPT-SNAs of all nucleobase types tested. Blue=nucleus. Scale bar=20 µm. By the MTT assay (8e) and flow cytometry analysis supported by propidium iodide staining (8f), CPT-poly G SNAs are also most cytotoxic among CPT-SNAs of all nucleobase types tested. Error bars denote the standard deviation from four measurements.

FIGS. 9a-9d depict the synthesis of CPT-DNA-SH. 9a) $^1$H NMR of camptothecin-azide (CPT-N3). 9b) By MALDI-ToF analysis, the molecular weight of the DNA strand increases by the expected amount after modification with a dibenzocyclooctyl tetraethylene glycol linker (DBCO-TEG; F.W.: 570.6; Glen Research). The molecular weight of DBCO-DNA-SH further increases by the expected amount upon reaction with CPT-N3 (F.W.: 487.5) by copper-free click coupling to form CPT-DNA-SH. Shown here are the representative spectra for the conjugation of $A_{30}$ DNA with DBCO and CPT. 9c) Molecular weights measured by MALDI-ToF MS agree with the expected molecular weights. 9d) Sequence information of the four types of CPT-DNA-SH strands (also shown in Table 4).

DETAILED DESCRIPTION OF THE INVENTION

Figures 1A, 1B:
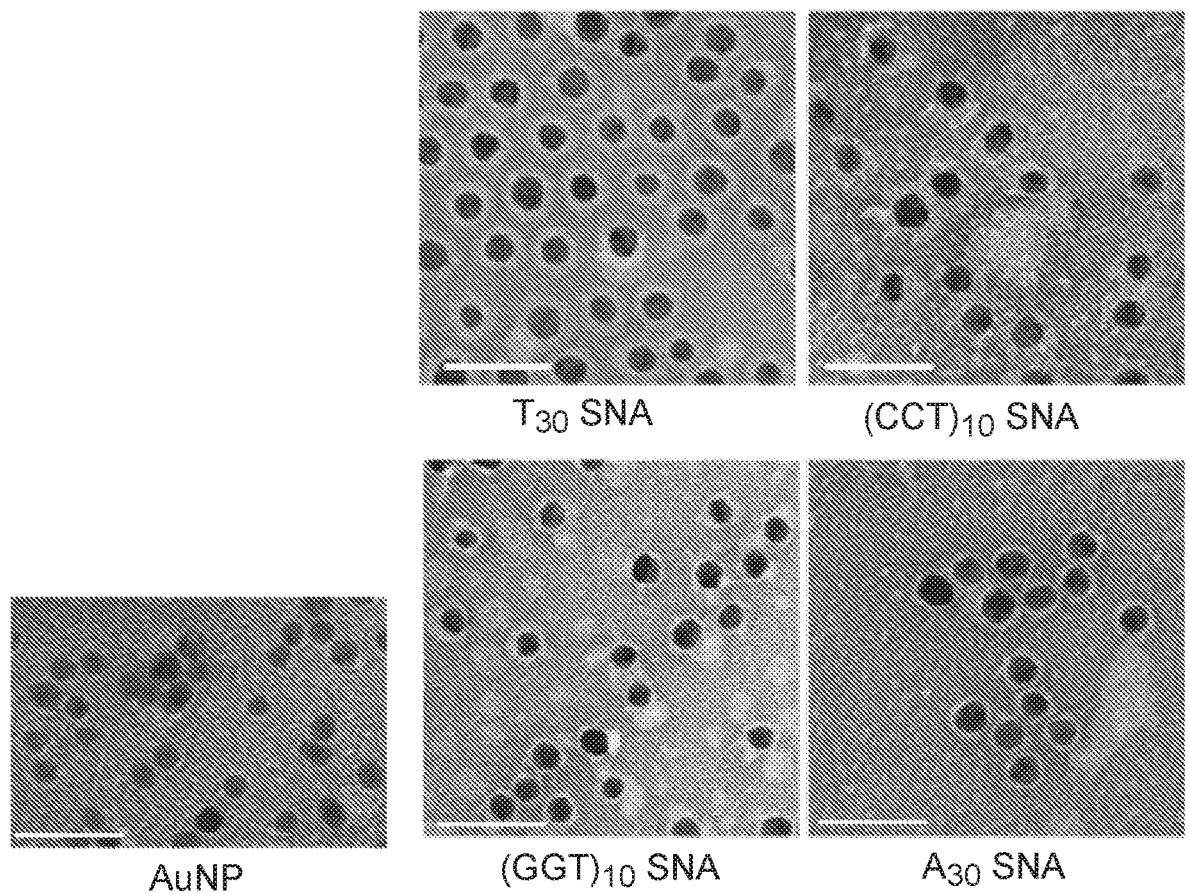
FIGS. 1a-1b show the characterization of SNAs. 1a) The table lists the loading of oligonucleotides on a 10 nm gold nanoparticle using a fluorescence-based assay. Poly T SNAs contain the highest loading among all nucleobase types, whereas poly A SNAs have the lowest. 1b) Staining of SNAs by uranyl acetate clearly delineates the DNA oligonucleotide shell (white) around the gold nanoparticle core (black) by TEM imaging. The thickness of the shell correlates with the oligonucleotide loading data obtained from the fluorescence-based assay. Scale bar=50 nm.

Spherical nucleic acids (SNAs), consisting of densely packed, highly oriented oligonucleotide strands attached to the surface of nanoparticles, are able to overcome the typical challenges of nucleic acid delivery. SNAs have been shown to effectively enter 50 different cell types without the use of auxiliary transfection agents and exhibit minimal cytotoxicity. Recently, the mechanism of endocytosis of these structures was shown to be dependent on class A scavenger receptors (SR-A). The present disclosure is directed to exploiting the interactions of SR-A with poly(guanylic acid) oligonucleotide strands, by constructing SNAs whose constituent oligonucleotide strands are rich in guanylic acid (G), will maximize the uptake of SNAs into cells.

Accordingly, the present disclosure demonstrates the utility of an oligonucleotide-functionalized nanoparticle, wherein the oligonucleotide further comprises a domain which modulates cellular uptake. As used herein, a "domain" is understood to be a sequence of nucleobases. Modified nucleobases as defined herein are also contemplated to make up a domain as provided herein. A domain is in one aspect collinear with an oligonucleotide functionalized on a nanoparticle. In another aspect, the domain is associated directly with the nanoparticle, absent association with an oligonucleotide functionalized on the nanoparticle. In still another aspect, the domain is associated with the nanoparticle through a spacer, and absent association with an oligonucleotide functionalized on the nanoparticle. In other words, the domain is in some embodiments associated with the nanoparticle through a spacer, separate from any association with an oligonucleotide (in such embodiments, therefore, the spacer does not comprise nucleobases).

As used herein, the term "nucleotide" takes on its ordinary meaning in the art. Thus, e.g., "A"=adenylic acid, "T"=thymidylic acid, "C"=cytidylic acid, "G"=guanylic acid, and"U"=uridylic acid, and "U"=uridylic acid.

It is noted here that, as used in this specification and the appended claims, the singular forms "a," "an," and "the" include plural reference unless the context clearly dictates otherwise.

As used herein, the term "polynucleotide," either functionalized on a SNA or as a target molecule, is used interchangeably with the term oligonucleotide and the terms have meanings accepted in the art.

It is further noted that the terms "attached", "conjugated" and "functionalized" are also used interchangeably herein and refer to the association of an oligonucleotide or domain with a nanoparticle.

"Hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

As used herein, a "poly X" domain (where "X" is a nucleotide, such as guanylic acid) is a sequence that comprises greater than 50% but less than 100% of "X" over its length. By way of example, a poly guanylic acid (poly G) domain that is 30 nucleotides in length consists of at least 15 (but less than 30) guanylic acid nucleotides. Thus, as used herein, a "poly X" domain is not a homopolymeric sequence.

Nanoparticles

Nanoparticles are provided which are functionalized to have a polynucleotide attached thereto. In general, nanoparticles contemplated include any compound or substance with a high loading capacity for a polynucleotide as described herein, including for example and without limitation, a metal, a semiconductor, a liposomal particle, insulator particle compositions, and a dendrimer (organic versus inorganic).

Thus, nanoparticles are contemplated which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles. Liposomal particles, for example as disclosed in PCT/US2014/068429 (incorporated by reference herein in its entirety) are also contemplated. Hollow particles, for example as described in U.S. Patent Publication Number 2012/0282186 (incorporated by reference herein in its entirety) are also contemplated herein.

In one embodiment, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, TiO$_2$, Sn, SnO$_2$, Si, SiO$_2$, Fe, Fe$^{+4}$, Ag, Cu, Ni, Al, steel, cobalt-chrome alloys, Cd, titanium alloys, AgI, AgBr, HgI$_2$, PbS, PbSe, ZnTe, CdTe, In$_2$S$_3$, In$_2$Se$_3$, Cd$_3$P$_2$, Cd$_3$As$_2$, InAs, and GaAs. Methods of making ZnS, ZnO, TiO$_2$, AgI, AgBr, HgI$_2$, PbS, PbSe, ZnTe, CdTe, In$_2$S$_3$, In$_2$Se$_3$, Cd$_3$P$_2$, Cd$_3$As$_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992).

In practice, methods of increasing cellular uptake and inhibiting gene expression are provided using any suitable particle having oligonucleotides attached thereto that do not interfere with complex formation, i.e., hybridization to a target polynucleotide. The size, shape and chemical composition of the particles contribute to the properties of the resulting oligonucleotide-functionalized nanoparticle. These properties include for example, optical properties, optoelectronic properties, electrochemical properties, electronic properties, stability in various solutions, magnetic properties, and pore and channel size variation. The use of mixtures of particles having different sizes, shapes and/or chemical compositions, as well as the use of nanoparticles having uniform sizes, shapes and chemical composition, is contemplated. Examples of suitable particles include, without limitation, nanoparticles particles, aggregate particles, isotropic (such as spherical particles) and anisotropic particles (such as non-spherical rods, tetrahedral, prisms) and core-shell particles such as the ones described in U.S. patent application Ser. No. 10/034,451, filed Dec. 28, 2002 and International application no. PCT/US01/50825, filed Dec. 28, 2002, the disclosures of which are incorporated by reference in their entirety.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preaparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Suitable nanoparticles are also commercially available from, for example, Ted Pella, Inc. (gold), Amersham Corporation (gold) and Nanoprobes, Inc. (gold).

Also as described in US patent application No 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using HAuCl$_4$ and a citrate-reducing agent, using methods known in the art. See, e.g., Marinakos et al., (1999) Adv. Mater. 11: 34-37; Marinakos et al., (1998) Chem. Mater. 10:

1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein.

Oligonucleotides

The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indo1-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096;

5,750,692 and U.S Pat. No. 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Nanoparticles provided that are functionalized with a polynucleotide, or a modified form thereof, and a domain as defined herein, generally comprise a polynucleotide from about 5 nucleotides to about 100 nucleotides in length. More specifically, nanoparticles are functionalized with a polynucleotide that is about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 125, about 150, about 175, about 200, about 250, about 300, about 350, about 400, about 450, about 500 or more nucleotides in length are contemplated.

In some embodiments, the polynucleotide attached to a nanoparticle is DNA. When DNA is attached to the nanoparticle, the DNA is in some embodiments comprised of a sequence that is sufficiently complementary to a target region of a polynucleotide such that hybridization of the DNA oligonucleotide attached to a nanoparticle and the target polynucleotide takes place, thereby associating the target polynucleotide to the nanoparticle. The DNA in various aspects is single stranded or double-stranded, as long as the double-stranded molecule also includes a single strand region that hybridizes to a single strand region of the target polynucleotide. In some aspects, hybridization of the oligonucleotide functionalized on the nanoparticle can form a triplex structure with a double-stranded target polynucleotide. In another aspect, a triplex structure can be formed by hybridization of a double-stranded oligonucleotide functionalized on a nanoparticle to a single-stranded target polynucleotide.

In some embodiments, the disclosure contemplates that a polynucleotide attached to a nanoparticle is RNA. In some aspects, the RNA is a small interfering RNA (siRNA).

Oligonucleotides, as defined herein, also includes aptamers. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. No. 5,270,163, and U.S. Pat. No. 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is about 10 to about 100 nucleotides in length, or about 100 to about 500 nucleotides in length. The production and use of aptamers is known to those of ordinary skill in the art.

In some aspects, multiple oligonucleotides are functionalized to a nanoparticle. In various aspects, the multiple oligonucleotides each have the same sequence, while in other aspects one or more oligonucleotides have a different sequence. In further aspects, multiple oligonucleotides are arranged in tandem and are separated by a spacer. Spacers are described in more detail herein below.

Polynucleotides contemplated for attachment to a nanoparticle include those which modulate expression of a gene product expressed from a target polynucleotide. Such polynucleotides include DNA, RNA, and modified forms thereof as defined herein below. Accordingly, in various aspects and without limitation, polynucleotides which hybridize to a target polynucleotide and initiate a decrease in transcription or translation of the target polynucleotide, triple helix forming polynucleotides which hybridize to double-stranded polynucleotides and inhibit transcription, and ribozymes which hybridize to a target polynucleotide and inhibit translation, are contemplated.

In various aspects, if a specific polynucleotide is targeted, a single functionalized oligonucleotide-nanoparticle composition has the ability to bind to multiple copies of the same transcript. In one aspect, a nanoparticle is provided that is functionalized with identical polynucleotides, i.e., each polynucleotide has the same length and the same sequence. In other aspects, the nanoparticle is functionalized with two or more polynucleotides which are not identical, i.e., at least one of the attached polynucleotides differ from at least one other attached polynucleotide in that it has a different length and/or a different sequence. In aspects wherein different polynucleotides are attached to the nanoparticle, these different polynucleotides bind to the same single target polynucleotide but at different locations, or bind to different target polynucleotides which encode different gene products.

Domain

The domain that is part of the oligonucleotide-functionalized nanoparticle as described herein is shown to affect the efficiency with which the nanoparticle is taken up by a cell. Accordingly, the domain increases or (through lack of the domain) decreases the efficiency. As used herein, "efficiency" refers to the number, amount or rate of uptake of nanoparticles in/by a cell. Because the process of nanoparticles entering and exiting a cell is a dynamic one, efficiency can be increased by taking up more nanoparticles or by retaining those nanoparticles that enter the cell for a longer period of time. Similarly, efficiency can be decreased by taking up fewer nanoparticles or by retaining those nanoparticles that enter the cell for a shorter period of time.

The domain, in some aspects, is located at the terminus of the oligonucleotide. In some embodiments, the domain is located at the 5' terminus of the oligonucleotide, and in further embodiments the domain is located at the 3' terminus of the oligonucleotide.

The domain, in some embodiments, is located at the terminus of the oligonucleotide that is not functionalized to the nanoparticle. In other words, in these embodiments the domain is at the terminus of the oligonucleotide that is distal to the nanoparticle surface. In further embodiments, the domain is at the terminus of the oligonucleotide that is distal to the nanoparticle surface and the domain is also free from attachment to any other molecule.

In some aspects, the domain is contiguous/colinear with the oligonucleotide. In some aspects, the domain is located at an internal region within the oligonucleotide. In further aspects, the domain is located on a second oligonucleotide that is attached to a nanoparticle. In one aspect, more than one domain is present in an oligonucleotide functionalized to a nanoparticle. Accordingly, in some aspects more than one domain is present, in tandem or individually, at the 5' end, and/or at the 3' end, and/or at an internal region of the oligonucleotide.

In another aspect, a domain, in some embodiments, is contemplated to be attached to a nanoparticle as a separate entity from an oligonucleotide, i.e., in some embodiments the domain is directly attached to the nanoparticle, separate from an oligonucleotide.

It is further contemplated that an oligonucleotide, in some embodiments, comprise more than one domain, located at one or more of the locations described herein.

The domain, in some embodiments, increases the efficiency of uptake of the oligonucleotide-functionalized nanoparticle by a cell. In various embodiments, the domain is from about 2 to about 1000, or from about 2 to about 500, or from about 2 to about 100, or from about 2 to about 50, or from about 2 to about 30, or from about 2 to about 20, or from about 2 to about 10, or from about 5 to about 100, or from about 5 to about 50, or from about 5 to about 30, or from about 5 to about 20, or from about 5 to about 10, or from about 10 to about 100, or from about 10 to about 50, or from about 10 to about 30, or from about 10 to about 20, or from about 10 to about 15, or from about 20 to about 100, or from about 20 to about 50, or from about 20 to about 40, or from about 20 to about 30 nucleotides in length. In further embodiments, the domain is less than 100, less than 80, less than 60, less than 50, less than 40, less than 30, less than 20, less than 10, or less than 5 nucleotides in length. As disclosed herein, the domain comprises a sequence of guanylic acid nucleotides (poly G). In various aspects, the domain comprises two guanylic acids. In further aspects, the domain comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 500 or more guanylic acid nucleotides.

The domain, in various aspects and embodiments of the disclosure, comprises a sequence that is at least about 50% but is less than 100% guanylic acid nucleotide. Thus, in some embodiments, the domain comprises a sequence that is at least 50%, at least 55%, at least 60%, at least 65%, at least 70%, at least 75%, at least 80%, at least 85%, at least 90%, or at least 95% guanylic acid nucleotide. In further embodiments, the domain comprises a sequence that is less than 55%, less than 60%, less than 65%, less than 70%, less than 75%, less than 80%, less than 85%, less than 90%, or less 95% guanylic acid nucleotide. In still further embodiments, the domain comprises a sequence that is from about 50% to 99%, or from about 60% to 99%, or from about 65% to 99%, or from about 70% to 99%, or from about 75% to 95%, or from about 80% to 99%, or from about 85% to 99%, or from about 90% to about 99%, or from about 95% to about 99% guanylic acid nucleotide. In some embodiments, the domain comprises a sequence that is 99% guanylic acid nucleotide. Homopolymeric guanylic acid sequences, i.e., sequences that are 100% guanylic acid, are not contemplated for use as a domain herein.

Thus, given the potential nucleotide lengths of the domain and the various percentages of guanylic acid nucleotide present in the domain, each as described above, it is contemplated that the remaining nucleotide sequence of the domain (i.e., the nucleotide sequence that is not guanylic acid but is part of the domain) is any nucleotide or modified form thereof. For example and without limitation, the domain in some embodiments is a $(GGX)_n$ sequence, where X is adenylic acid, thymidylic acid, uridylic acid, cytidylic acid (or modified forms thereof) and n is from about 1 to about 500. In some embodiments, X is guanylic acid (provided that, in such embodiments, the domain is not a homopolymeric guanylic acid sequence). In some embodiments, n is 1, 2, 3, 4, 5, 6, 7, 8, 9, 10, 11, 12, 13, 14, 15, 16, 17, 18, 19, or 20.

In some embodiments, it is contemplated that a nanoparticle functionalized with an oligonucleotide and a domain is taken up by a cell with greater efficiency than a nanoparticle functionalized with the same oligonucleotide but lacking the domain. In some aspects, a nanoparticle functionalized with an oligonucleotide and a domain is taken up by a cell 1% more efficiently than a nanoparticle functionalized with the same oligonucleotide but lacking the domain. In various aspects, a nanoparticle functionalized with an oligonucleotide and a domain is taken up by a cell 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold, about 150-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, about 2000-fold, about 2500-fold, about 3000-fold, about 3500-fold, about 4000-fold, about 4500-fold, about 5000-fold, about 5500-fold, about 6000-fold, about 6500-fold, about 7000-fold, about 7500-fold, about 8000-fold, about 8500-fold, about 9000-fold, about 9500-fold, about 10000-fold or higher, more efficiently than a nanoparticle functionalized with the same oligonucleotide but lacking the domain.

In some embodiments, lack of the domain decreases the efficiency of uptake of the oligonucleotide-functionalized nanoparticle by a cell. In some embodiments, it is contemplated that a nanoparticle functionalized with an oligonucleotide but lacking a domain is taken up by a cell with lower efficiency than a nanoparticle functionalized with the same oligonucleotide that comprises the domain. In some aspects, a nanoparticle functionalized with an oligonucleotide but lacking a domain is taken up by a cell 1% less efficiently than a nanoparticle functionalized with the same oligonucleotide comprising the domain. In various aspects, a nanoparticle functionalized with an oligonucleotide but lacking a domain is taken up by a cell 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold, about 150-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, about 2000-fold, about 2500-fold, about 3000-fold, about 3500-fold, about 4000-fold, about 4500-fold, about 5000-fold, about 5500-fold, about 6000-fold, about 6500-fold, about 7000-fold, about 7500-fold, about 8000-fold, about 8500-fold, about 9000-fold, about 9500-fold, about 10000-fold or higher, less efficiently than a nanoparticle functionalized with the same oligonucleotide and comprising the domain.

Modified Oligonucleotides

As discussed above, modified oligonucleotides are contemplated for functionalizing nanoparticles. In various aspects, an oligonucleotide functionalized on a nanoparticle is completely modified or partially modified. Thus, in various aspects, one or more, or all, sugar and/or one or more or all internucleotide linkages of the nucleotide units in the polynucleotide are replaced with "non-naturally occurring" groups.

In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide."

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —CH$_2$—NH—O—CH$_2$—, —CH$_2$—N(CH$_3$)—O—CH$_2$—, —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the oligo consists of 2 to 4, desirably 3, groups/atoms selected from —CH$_2$—, —O—, —S—, —NRH—, >C=O, >C=NRH, >C=S, —Si(R")$_2$—, —S(O)$_2$—, —P(O)(BH$_3$)—, —P(O,S)—, —P(S)$_2$—, —PO(R")—, —PO(OCH$_3$)—, and —PO(NHRH)—, where RH is selected from hydrogen and C1-4-alkyl, and R" is selected from C1-6-alkyl and phenyl. Illustrative examples of such linkages are —CH$_2$—CH$_2$—CH$_2$—, —CH$_2$—CO—CH$_2$—, —CH$_2$—CHOH—CH$_2$—, —O—CH2-O—, —O—CH2-CH2-, —O—CH2-CH=(including R5 when used as a linkage to a succeeding monomer), —CH$_2$—CH$_2$—O—, —NRH—CH$_2$—CH$_2$—, —CH$_2$—CH$_2$—NRH—, —CH$_2$—NRH—CH$_2$—, —O—CH$_2$—CH$_2$—NRH—, —NRH—CO—O—, —NRH—CO—NRH—, —NRH—CS—NRH—, —NRH—C(=NRH)—NRH—, —NRH—CO—CH$_2$—NRH—O—CO—O—, —O—CO—CH$_2$—O—, —O—CH$_2$—CO—O—, —CH$_2$—CO—NRH—, —O—CO—NRH—, —NRH—CO—CH$_2$—, —O—CH$_2$—CO—NRH—, —O—CH$_2$—CH$_2$—NRH—, —CH=N—O—, —CH$_2$—NRH—O—, —CH$_2$—O—N=(including R5 when used as a linkage to a succeeding monomer), —CH$_2$—O—NRH—, —CO—NRH—CH$_2$—, —CH$_2$—NRH—O—, —CH$_2$—NRH—CO—, —O—NRH—CH$_2$—, —O—NRH, —O—CH$_2$—S—, —S—CH$_2$—O—, —CH$_2$—CH$_2$—S—, —O—CH$_2$—CH$_2$—S—, —S—CH$_2$—CH=(including R5 when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—, —O—S(O)$_2$—NRH—, —NRH—S(O)$_2$—CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(O CH$_2$CH$_3$)—O—, —O—PO(O CH$_2$CH$_2$S—R)—O—, —O—PO(BH$_3$)—O—, —O—PO(NHRN)—O—, —O—P(O)$_2$—NRH H—, —NRH—P(O)$_2$—O—, —O—P(O,NRH)—O—, —CH$_2$—P(O)$_2$—O—, —O—P(O)$_2$—CH$_2$—, and —O—Si(R")$_2$—O—; among which —CH$_2$—CO—NRH—, —CH$_2$—NRH—O—, —S—CH$_2$—O—, —O—P(O)$_2$—O—O—P(—O,S)—O—, —O—P(S)$_2$—O—, —NRH P(O)$_2$—O—, —O—P(O,NRH)—O—, —O—PO(R")—O—, —O—PO(CH$_3$)—O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O-, S-, or N-alkyl; O-, S-, or N-alkenyl; O-, S- or N-alkynl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[(CH$_2$)$_n$O]$_m$CH$_3$, O(CH2)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$), 2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH$_2$-)n group bridging the 2' oxygen atom and the 4' carbon atom wherein n is 1 or 2. LNAs and preparation thereof are described in WO 98/39352 and WO 99/14226, the disclosures of which are incorporated herein by reference.

Oligonucleotide Attachment to a Nanoparticle

Oligonucleotides contemplated for use in the methods include those bound to the nanoparticle through any means. Regardless of the means by which the oligonucleotide is attached to the nanoparticle, attachment in various aspects is effected through a 5' linkage, a 3' linkage, some type of internal linkage, or any combination of these attachments.

Methods of attachment are known to those of ordinary skill in the art and are described in US Publication No. 2009/0209629, which is incorporated by reference herein in its entirety. Methods of attaching RNA to a nanoparticle are generally described in PCT/US2009/65822, which is incorporated by reference herein in its entirety.

Nanoparticles with oligonucleotides attached thereto are thus provided wherein an oligonucleotide further comprising a domain is associated with the nanoparticle.

Spacers

In certain aspects, functionalized nanoparticles are contemplated which include those wherein an oligonucleotide and a domain are attached to the nanoparticle through a spacer. "Spacer" as used herein means a moiety that does not participate in modulating gene expression per se but which serves to increase distance between the nanoparticle and the functional oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences. In aspects of the invention where a domain is attached directly to a nanoparticle, the domain is optionally functionalized to the nanoparticle through a spacer. In another aspect, the domain is on the end of the oligonucleotide that is opposite to the spacer end. In aspects wherein domains in tandem are functionalized to a nanoparticle, spacers are optionally between some or all of the domain units in the tandem structure. In one aspect, the spacer when present is an organic moiety. In another aspect, the spacer is a polymer, including but not limited to a water-soluble polymer, a nucleic acid, a polypeptide, an oligosaccharide, a carbohydrate, a lipid, an ethylglycol, or combinations thereof.

In certain aspects, the polynucleotide has a spacer through which it is covalently bound to the nanoparticles. These polynucleotides are the same polynucleotides as described above. As a result of the binding of the spacer to the nanoparticles, the polynucleotide is spaced away from the surface of the nanoparticles and is more accessible for hybridization with its target. In instances wherein the spacer is a polynucleotide, the length of the spacer in various embodiments at least about 10 nucleotides, 10-30 nucleotides, or even greater than 30 nucleotides. The spacer may have any sequence which does not interfere with the ability of the polynucleotides to become bound to the nanoparticles or to the target polynucleotide. In certain aspects, the bases of the polynucleotide spacer are all adenylic acids, all thymidylic acids, all cytidylic acids, all guanylic acids, all uridylic acids, or all some other modified base. Accordingly, in some aspects wherein the spacer consists of all guanylic acids, it is contemplated that the spacer can function as a domain as described herein.

Surface Density

Nanoparticles as provided herein have a packing density of the polynucleotides on the surface of the nanoparticle that is, in various aspects, sufficient to result in cooperative behavior between nanoparticles and between polynucleotide strands on a single nanoparticle. In another aspect, the cooperative behavior between the nanoparticles increases the resistance of the polynucleotide to nuclease degradation. In yet another aspect, the uptake of nanoparticles by a cell is influenced by the density of polynucleotides associated with the nanoparticle. As described in U.S. Patent Application Publication Number 2008/0306016, incorporated herein by reference in its entirety, a higher density of polynucleotides on the surface of a nanoparticle is associated with an increased uptake of nanoparticles by a cell. The disclosure provides embodiments wherein the increased uptake of a nanoparticle due to a higher density of polynucleotides on the nanoparticle surface works in combination with the presence of a domain as described herein. For example and without limitation, a nanoparticle with a given density of polynucleotides on the surface of the nanoparticle, wherein the nanoparticle further comprises a poly G domain as disclosed herein, will demonstrate an increased uptake of the functionalized nanoparticle by a cell relative to a nanoparticle with an identical density of polynucleotides on the surface of the nanoparticle, wherein the nanoparticle lacks a poly G domain. In various aspects, the increase in uptake by a cell of the functionalized nanoparticle further comprising the poly G domain is 1% relative to the functionalized nanoparticle lacking the poly G domain. In further aspects, the increase in uptake by a cell of the functionalized nanoparticle further comprising the poly G domain is 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold, about 150-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, about 2000-fold, about 2500-fold, about 3000-fold, about 3500-fold, about 4000-fold, about 4500-fold, about 5000-fold, about 5500-fold, about 6000-fold, about 6500-fold, about 7000-fold, about 7500-fold, about 8000-fold, about 8500-fold, about 9000-fold, about 9500-fold, about 10000-fold or higher relative to the functionalized nanoparticle lacking the poly G domain.

A surface density adequate to make the nanoparticles stable and the conditions necessary to obtain it for a desired combination of nanoparticles and polynucleotides can be determined empirically. Generally, a surface density of at least about 2 pmoles/cm$^2$ will be adequate to provide stable nanoparticle-oligonucleotide compositions. In some aspects, the surface density is at least 15 pmoles/cm$^2$. Methods are also provided wherein the polynucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm², at least about 65 pmol/cm², at least about 70 pmol/cm², at least about 75 pmol/cm², at least about 80 pmol/cm², at least about 85 pmol/cm², at least about 90 pmol/cm², at least about 95 pmol/cm², at least about 100 pmol/cm², at least about 125 pmol/cm², at least about 150 pmol/cm², at least about 175 pmol/cm², at least about 200 pmol/cm², at least about 250 pmol/cm², at least about 300 pmol/cm², at least about 350 pmol/cm², at least about 400 pmol/cm², at least about 450 pmol/cm², at least about 500 pmol/cm², at least about 550 pmol/cm², at least about 600 pmol/cm², at least about 650 pmol/cm², at least about 700 pmol/cm², at least about 750 pmol/cm², at least about 800 pmol/cm², at least about 850 pmol/cm², at least about 900 pmol/cm², at least about 950 pmol/cm², at least about 1000 pmol/cm² or more.

Oligonucleotide Target Sequences and Hybridization

In some aspects, the disclosure provides methods of targeting specific nucleic acids. Any type of nucleic acid may be targeted, and the methods may be used, e.g., for therapeutic modulation of gene expression (See, e.g., U.S. Patent Application Publication Number 2009/0209629, the disclosure of which is incorporated herein by reference). Examples of nucleic acids that can be targeted by the methods of the invention include but are not limited to genes (e.g., a gene associated with a particular disease), bacterial RNA or DNA, viral RNA, or mRNA, RNA, or single-stranded nucleic acids.

The terms "start codon region" and "translation initiation codon region" refer to a portion of a mRNA or gene that encompasses contiguous nucleotides in either direction (i.e., 5' or 3') from a translation initiation codon. Similarly, the terms "stop codon region" and "translation termination codon region" refer to a portion of such a mRNA or gene that encompasses contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligonucleotides on the functionalized nanoparticles.

Other target regions include the 5' untranslated region (5'UTR), the portion of an mRNA in the 5' direction from the translation initiation codon, including nucleotides between the 5' cap site and the translation initiation codon of a mRNA (or corresponding nucleotides on the gene), and the 3' untranslated region (3'UTR), the portion of a mRNA in the 3' direction from the translation termination codon, including nucleotides between the translation termination codon and 3' end of a mRNA (or corresponding nucleotides on the gene). The 5' cap site of a mRNA comprises an N7-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap site.

For prokaryotic target nucleic acid, in various aspects, the nucleic acid is RNA transcribed from genomic DNA. For eukaryotic target nucleic acid, the nucleic acid is an animal nucleic acid, a plant nucleic acid, a fungal nucleic acid, including yeast nucleic acid. As above, the target nucleic acid is a RNA transcribed from a genomic DNA sequence. In certain aspects, the target nucleic acid is a mitochondrial nucleic acid. For viral target nucleic acid, the nucleic acid is viral genomic RNA, or RNA transcribed from viral genomic DNA.

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of an oligonucleotide-functionalized nanoparticle. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanoparticle and a specific oligonucleotide.

EXAMPLES

The sequence-dependent cellular uptake of spherical nucleic acid nanoparticle conjugates (SNAs) was investigated. This process occurs by interaction with class A scavenger receptors (SR-A) and caveolae-mediated endocytosis. It is known that linear poly(guanylic acid) (poly G) is a natural ligand for SR-A. The examples described below tested whether SNAs with higher G contents would be able to enter cells in larger amounts than SNAs composed of other nucleotides, and as such the cellular internalization of SNAs was measured as a function of constituent oligonucleotide sequence. As seen below, SNAs with enriched G content showed the highest cellular uptake. Next, a small molecule (camptothecin) was chemically conjugated with SNAs to create drug-SNA conjugates and it was observed that poly G SNAs deliver the most camptothecin to cells and have the highest cytotoxicity in cancer cells. The data provided herein elucidate important design considerations for enhancing the intracellular delivery of spherical nucleic acids.

The enhanced cellular uptake of G-rich SNAs was investigated in four cell types, A549 (human lung adenocarcinoma epithelial), NIH-3T3 (mouse fibroblasts), C166 (mouse endothelial), and HaCaT (human keratinocytes). In addition, the consequences of sequence-dependent cellular uptake was studied by designing SNAs loaded with DNA-chemotherapeutic conjugates and increased the delivery of camptothecin chemotherapeutic molecules to A549 cells and subsequent cytotoxicity with G-rich SNAs compared to SNAs enriched in A, T, and C.

Example 1

Figure 2:
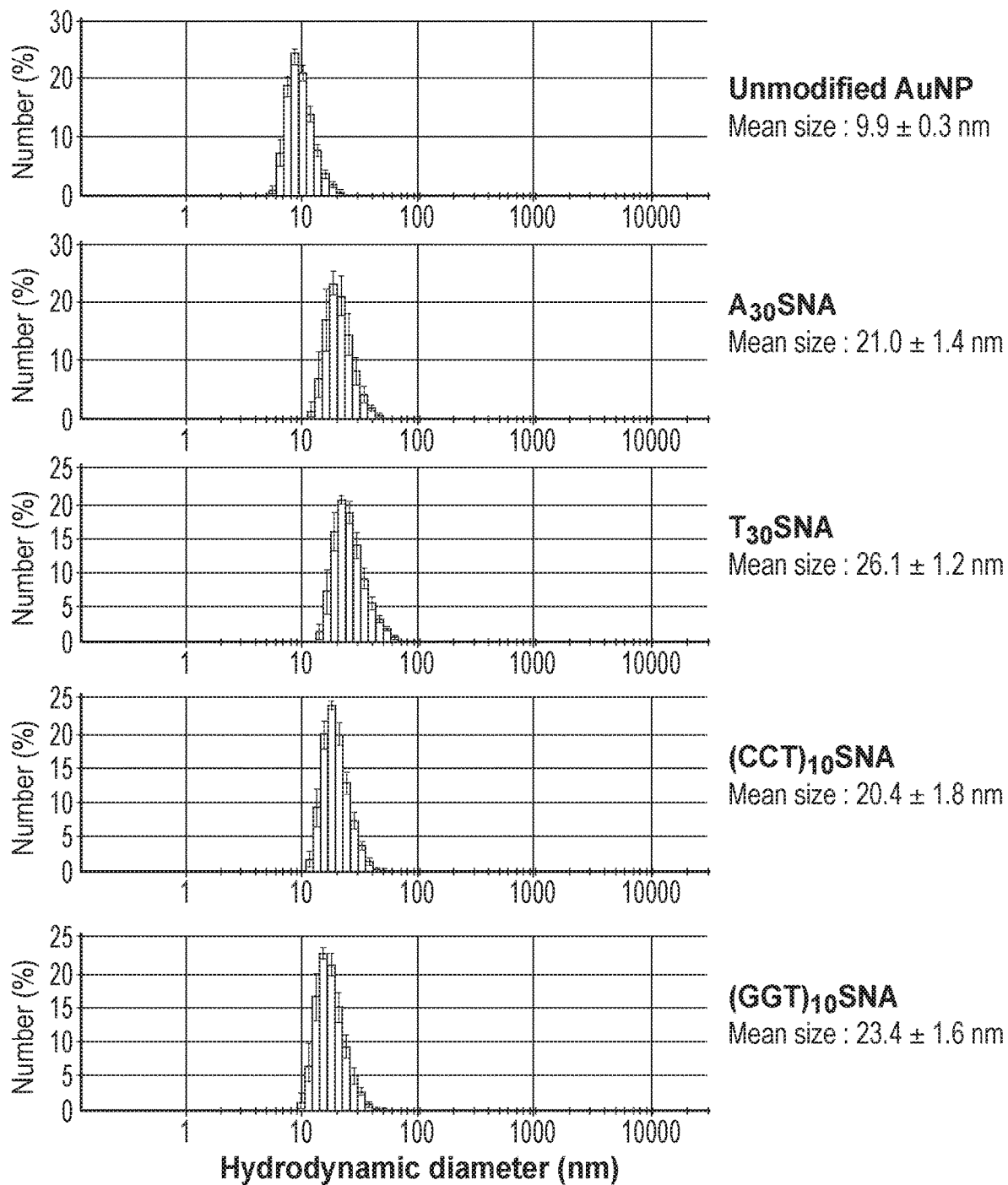
FIG. 2 depicts dynamic light scattering analysis. Covalent attachment of oligonucleotide strands composed of different nucleobase types onto the surface of 10 nm AuNPs increases the hydrodynamic diameter by 10-15 nm, indicating a thickness of 5-8 nm for the oligonucleotide shell.
Figure 3A:
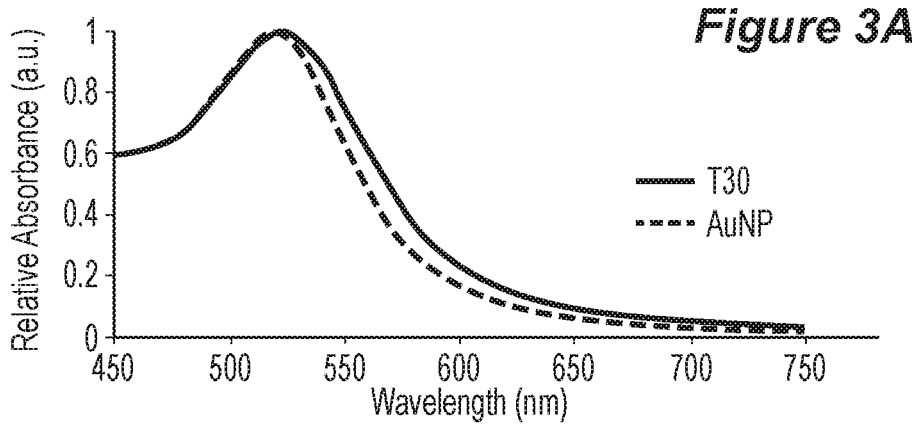
FIG. 3 shows UV-Vis absorption spectra of SNAs. Covalent attachment of the DNA oligonucleotide shell to the AuNP core causes a red shift in the surface plasmon peak, from 519 nm for unmodified citrate-capped AuNPs to 524 nm, independent of the nucleobase type comprising the shell.
Figure 3B:
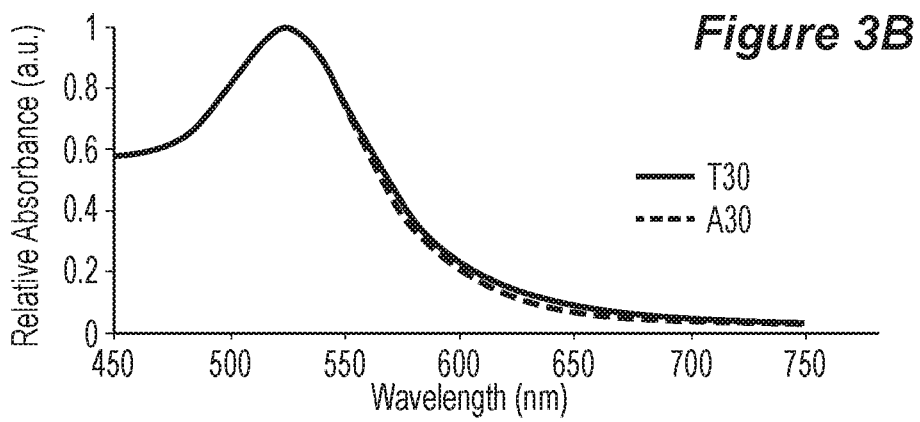
Figure 3C:
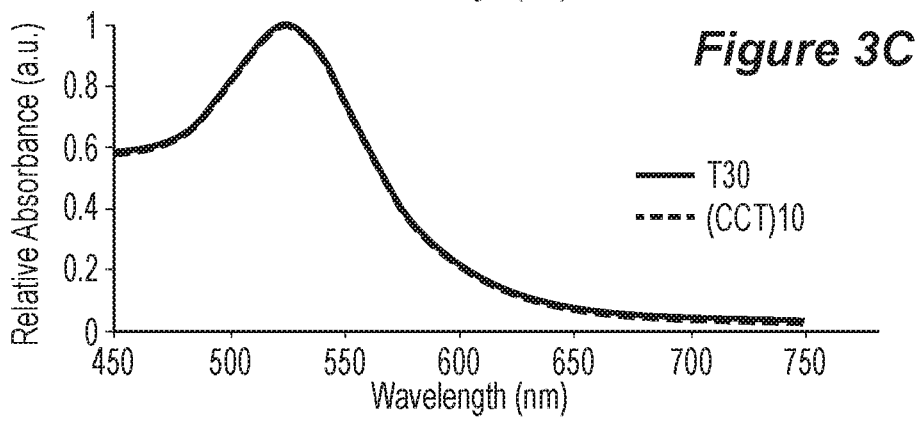
Figure 3D:
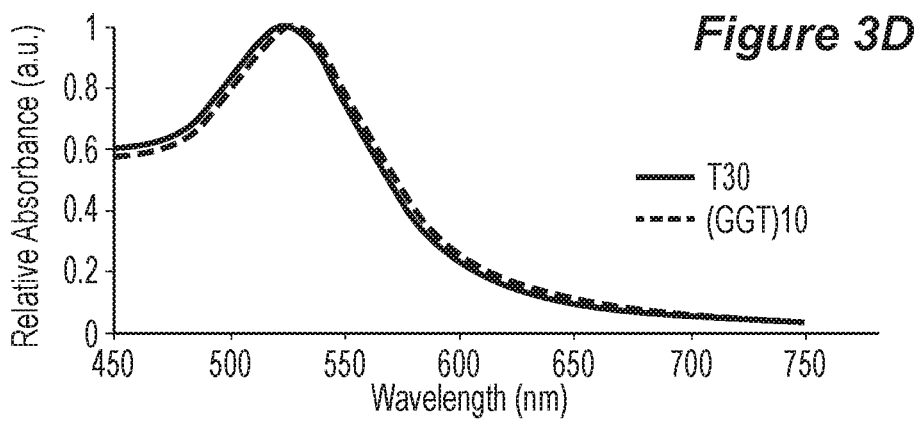
Figures 4A, 4B:
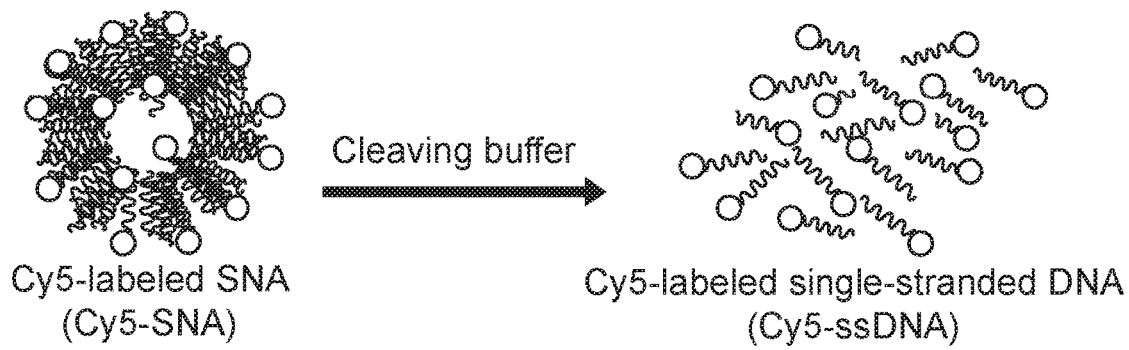
FIGS. 4a-4b depict the measurement of oligonucleotide loading. 4a) Cy5-labeled SNAs were used to quantify the loading of poly A, poly T, poly C, and poly G SNAs. Reduction of the Au-thiol bond by the addition of 1 M dithiothreitol (DTT) releases Cy5-labeled, single-stranded DNA (Cy5-ssDNA) from the surface of the AuNP and allows for quantification by Cy5 fluorescence. 4b) The Cy5 moiety is attached to the 5' end of the constituent oligonucleotides.

Nucleobase Type on SNAs Dictates Loading and Thickness of the DNA Oligonucleotide Shell on the Surface of a Gold Nanoparticle First, SNAs composed of different nucleobase types (A, T, C, or G) were prepared by adding the same amounts of alkylthiol-modified, 30-base-pair long, single-stranded DNA oligonucleotides (ssDNAs) of different nucleobase types (FIG. 1a; see Table 1 below for sequence information) into an aqueous suspension of citrate-capped 10 nanometer (nm) diameter gold nanoparticles (AuNPs). To prepare SNAs enriched in C (poly C SNAs) and G (poly G SNAs), Ts were deliberately inserted at regular intervals along the linear polymers of C and G, yielding sequences of $(CCT)_{10}$ and $(GGT)_{10}$, respectively. For poly C SNAs and poly G SNAs, these design features attenuate the challenges of synthesizing poly C and poly G sequences, which is made difficult due to the formation of i-motifs [Gehring et al., Nature 363: 561-565 (1993)] and G-quadruplexes [Sen et al., Nature 334: 364-366 (1988)]. On the contrary, linear polymers of A and T do not naturally fold into stable secondary structures, negating the need to dilute the linear polymers of A and T with another nucleobase when SNAs enriched in A (poly A SNAs) and T (poly T SNAs) were prepared. By dynamic light scattering measurements, all SNAs possess a hydrodynamic diameter of 22±4 nm, suggesting a thickness of 5-8 nm for the oligonucleotide shell (FIG. 2). The variation in thickness is likely due to variation in loading (see below). By UV-Vis spectroscopy, all SNAs are generally monodisperse in size, and exhibit a red-shift of approximately 4 nm in the surface plasmon peak compared to unmodified AuNPs (524 nm vs. 520 nm) due to changes in the local refractive index upon the covalent attachment of the oligonucleotide shell [Kumar et al., Nat Protoc 3: 314-320 (2008)] (FIG. 3). Oligonucleotide loading was then measured as a function of nucleobase type by preparing SNAs whose oligonucleotides contain a Cy5 fluorophore at their 5' end (FIG. 4). Given a constant oligonucleotide length of 30 bases, SNAs enriched in pyrimidine bases (i.e., C and T) have noticeably higher oligonucleotide loading, whereby poly T SNAs and poly C SNAs have approximately 180 ssDNAs and approximately 140 ssDNAs per AuNP, respectively. By contrast, SNAs enriched in purine bases have lower oligonucleotide loading: poly G SNAs and poly A SNAs have only approximately 75 ssDNAs and approximately 45 ssDNAs per AuNP, respectively (FIG. 1a).

TABLE 1

List of SNA nanoparticle conjugates and their DNA oligonucleotide sequences.

| Type of SNA | Sequence of constituent DNA oligonucleotides (5'→3') | SEQ ID NO: |
|---|---|---|
| Poly SNA; $A_{30}$ | AAA AAA AAA AAA AAA AAA AAA AAA AAA AAA propylthiol | 1 |
| Poly T SNA; $T_{30}$ | TTT TTT TTT TTT TTT TTT TTT TTT TTT TTT propylthiol | 2 |
| Poly C SNA; $(CCT)_{10}$ | CCT CCT CCT CCT CCT CCT CCT CCT CCT CCT propylthiol | 3 |
| Poly G SNA; $(GGT)_{10}$ | GGT GGT GGT GGT GGT GGT GGT GGT GGT GGT propylthiol | 4 |

SNAs comprised of the DNA oligonucleotides listed in Table 1 were prepared to examine the effect of nucleobase type on their cellular uptake kinetics and intracellular distribution using ICP-MS and TEM, respectively (FIG. 5).
FIGS. 2 and 3 present DLS and UV-Vis spectroscopic data on the hydrodynamic size and absorption spectra of these SNAs.
The TEM imaging data in FIG. 1 reveal the morphology of the SNAs.

To directly visualize the oligonucleotide shell by transmission electron microscopy (TEM), a uranyl acetate staining protocol for SNAs was utilized [Huxley et al., J Biophys Biochem Cytol 11: 273-296 (1961)]. In agreement with the loading data, the oligonucleotide coverage for poly T SNAs is the densest among all nucleobase types tested, as evidenced by their uniform oligonucleotide shell of 4-6 nm in dry thickness in the entire circumference of the AuNPs (FIG. 1b). Chen et al. used single-molecule FRET (smFRET) and small-angle X-ray scattering (SAXS) to demonstrate that the end-to-end distance of a single-stranded poly T DNA of 40 bases long ($T_{40}$) is approximately 6.6 nm in the presence of physiological levels of salt (150 mM NaCl) [Chen et al., Proc Natl Acad Sci U.S.A. 109: 799-804 (2012)]. Thus, the dry shell thickness of poly T SNAs as revealed by the TEM images suggests that the poly T DNA strands are approaching the maximum loading afforded by the curved surface of an AuNP when they radially extend away from the center of the AuNP. Poly A SNAs possess the thinnest oligonucleotide shell of merely 1-2 nm in thickness, but their shells are still uniform. Given their intermediate oligonucleotide loading, poly C SNAs and poly G SNAs have 2-4 nm thick oligonucleotide shells, but their shells are not as uniform as poly T SNAs and poly A SNAs. Although this technique is subject to drying effects, the data are in agreement with results from oligonucleotide loading studies (FIG. 1a). In brief, the oligonucleotide loading and TEM imaging data are consistent with literature precedents that pyrimidine bases (C and T) adsorb to the gold surface less strongly than their purine counterparts (A and G) [Demers et al., J Am Chem Soc 124: 11248-11249 (2002); Hurst et al., 78, 8313-8318 (2006); Storhoff et al., Langmuir 18: 6666-6670 (2002); Kimura-Suda et al., Journal of the American Chemical Society 125: 9014-9015 (2003); Opdahl et al., Proc Natl Acad Sci U.S.A. 104: 9-14 (2007)], supporting the idea that the former extend away from the gold surface whereas the latter interact with the surface.

Example 2

Figure 5A:
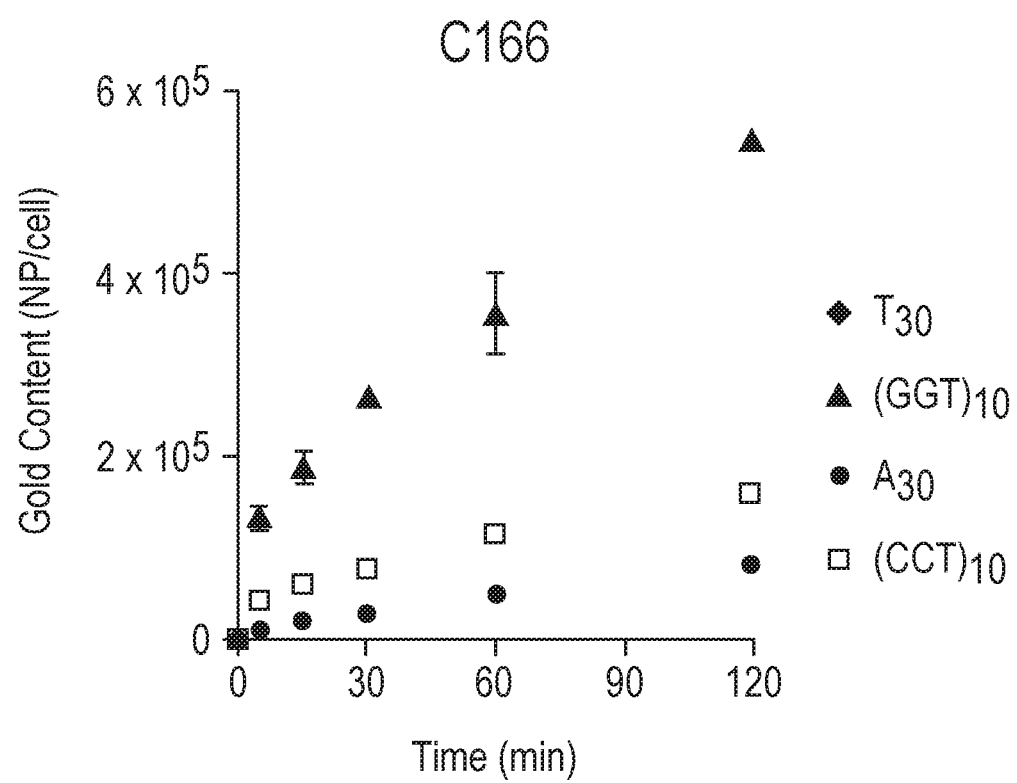
FIGS. 5a-5c depict cellular uptake of SNAs. 5a) Poly G SNAs show the highest association with C166 cells, 4-10 times higher than SNAs composed of other nucleobase types. 5b) By TEM imaging, poly G SNAs exhibit the highest accumulation inside C166 cells, as evidenced by their widespread distribution throughout the cytosol as large clusters (>100 per clusters). By contrast, SNAs composed of other nucleobase types either accumulate in more confined regions of the cytosol or appear in clusters that contain fewer particles (<20 particles per cluster). The bottom row features enlarged images of the boxed regions of the top row. 5c) Poly G SNAs also demonstrate the highest association with three other cell lines beside C166, including, in descending order of expression level for SR-A, HaCaT (immortal human keratinocyte), 3T3 (mouse fibroblast), and A549 (human lung epithelial adenocarcinoma). For all cell types, poly G SNAs exhibit 3-5 times higher association with cells than SNAs of other nucleobase types. Association of poly G SNAs with cells positively correlates with the expression level of SR-A for the same cell types. Error bars denote the standard deviation from triplicate measurements.
Figure 12:
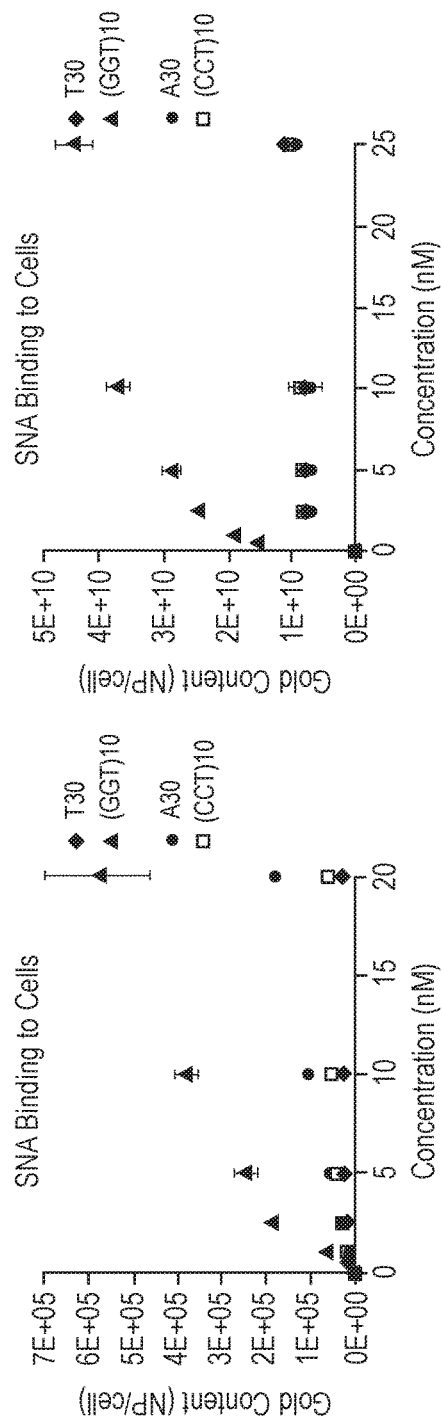
FIG. 12 demonstrates that poly G SNAs show higher cellular association with C166 cells than poly A, poly T, and poly C SNAs.
Figure 13:
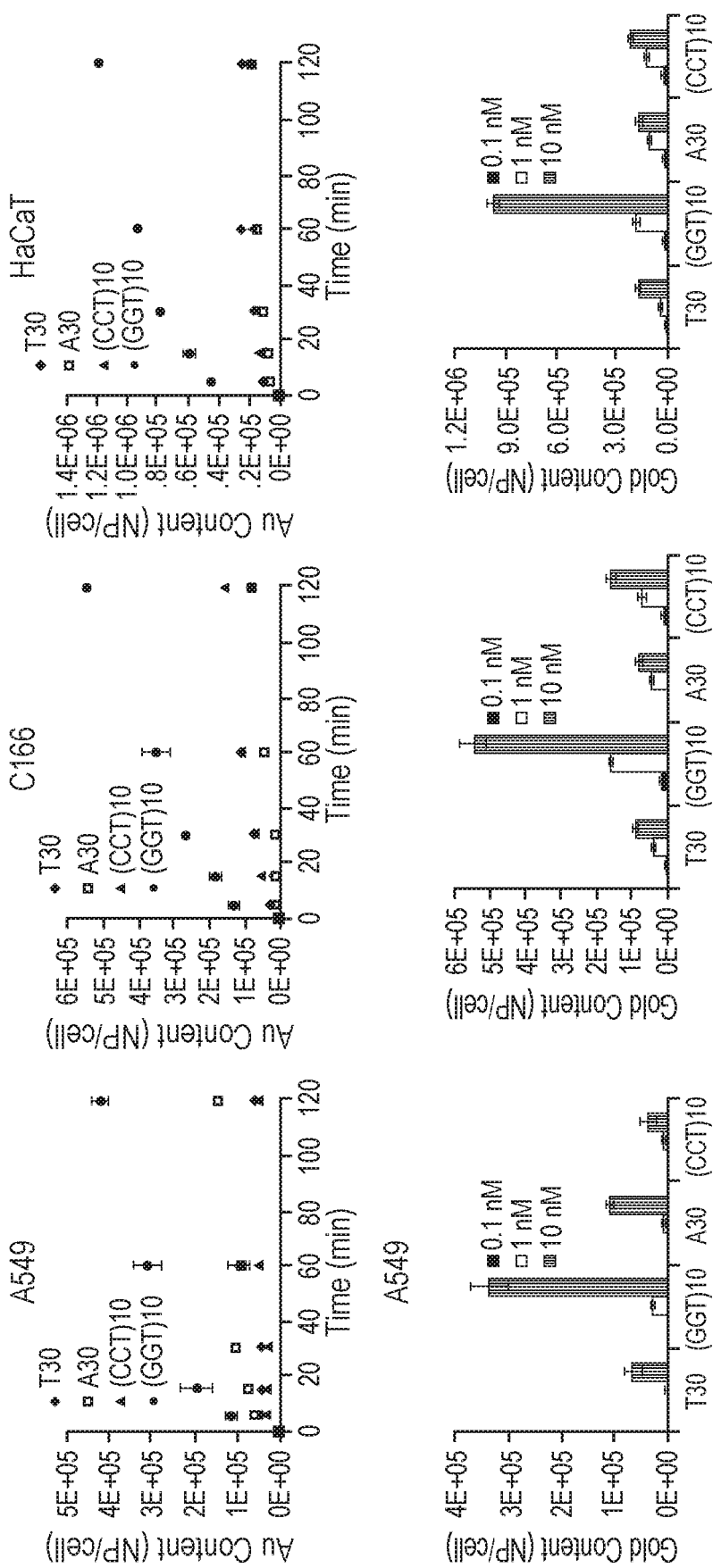
FIG. 13 shows the cellular uptake of SNAs.

Poly G SNAs Enter Multiple Mammalian Cell Types in Highest Amounts Among all Nucleobase Types Tested Next, the cellular uptake kinetics of SNAs of different nucleobase types was monitored by inductively coupled plasma mass spectrometry (ICP-MS). C166 cells were chosen because of their expression of SR-A [Choi et al., Proc Natl Acad Sci U.S.A. 110: 7625-7630 (2013)], a key receptor that mediates the cellular uptake of SNAs (FIG. 5a). After two hours of incubation, poly G SNAs exhibit the highest level of cellular association among all nucleobase types tested, accumulating $5\times10^5$ particles per cell. In contrast to poly G SNAs, poly T SNAs show over five-fold lower cellular association, the lowest level of cellular association among all nucleobase types. Poly A and poly C SNAs exhibit intermediate levels of cellular association compared to poly T SNAs and poly G SNAs. Similar data are presented in FIG. 13. See also FIG. 12, which demonstrates that poly G SNAs show higher cellular association with C166 cells than poly A, poly T, and poly C SNAs. A modified ELISA assay shows that poly G SNAs demonstrate the highest association with recombinant class A scavenger receptors (SR-A), which is responsible for the increased cellular association of poly G SNAs.

Figure 5B:
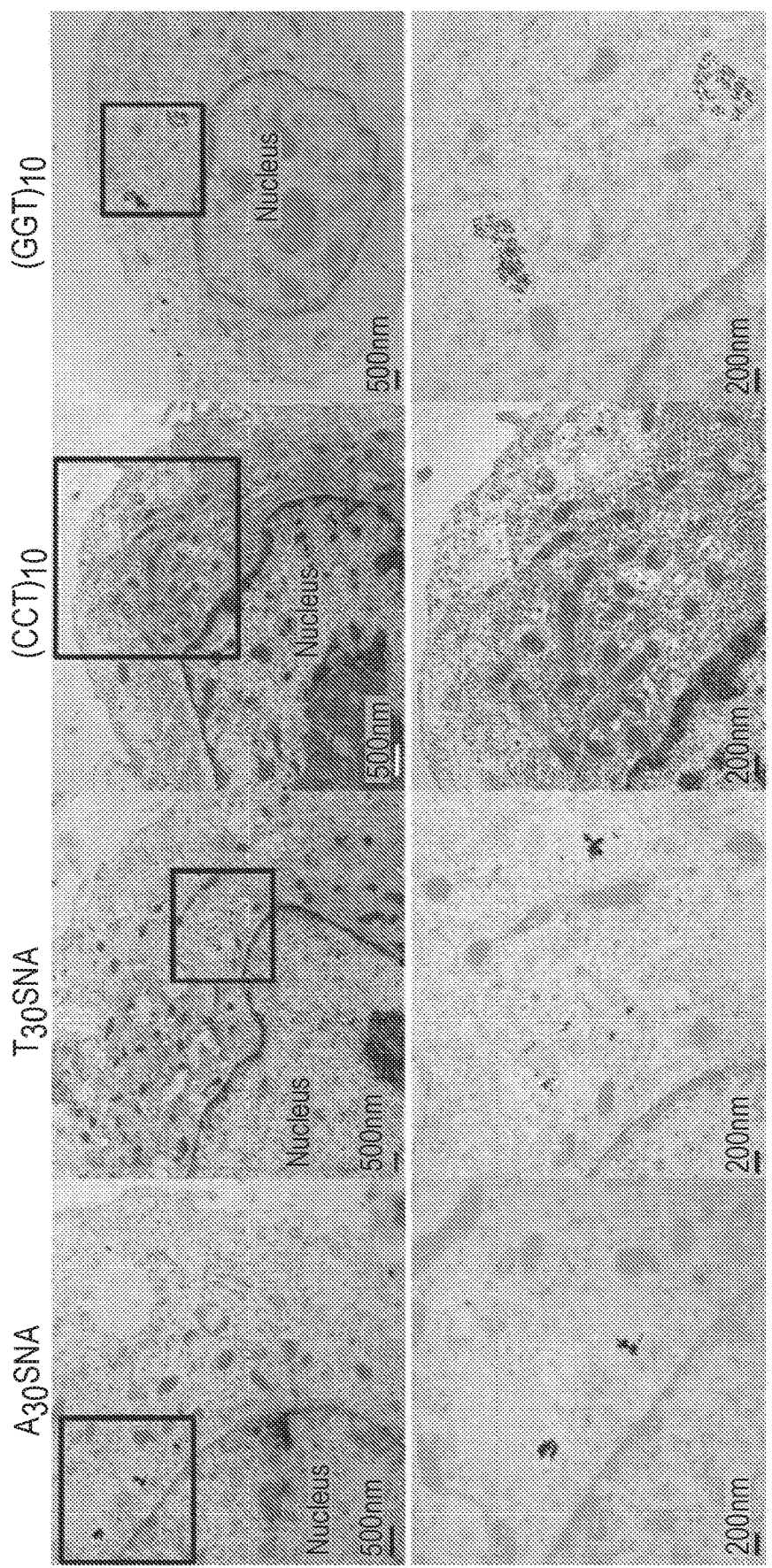

However, ICP-MS, a technique that allows for sensitive quantification of the bulk content of gold associated with cells, does not provide any information on the intracellular distribution of SNAs. Therefore, TEM was utilized to determine whether SNAs enter cells or merely associate with the cell membrane (FIG. 5b). After 2 hours of incubation with cells, SNAs composed of all nucleobase types can enter C166 cells, as evidenced by their accumulation inside either the cytosol or early endosomes. In agreement with the ICP-MS data, representative TEM images show that poly G SNAs are the most abundant in the cell among all nucleobase types, both in terms of number of particle clusters per cross-sectional area of the cell and number of particles per cluster (typically >100 SNAs per cluster). By contrast, poly A SNAs, poly C SNAs, and poly T SNAs enter cells in considerably smaller amounts than poly G SNAs (<20 SNAs per cluster), although TEM images do not permit precise quantification of particles in the cell.

Figure 5C:
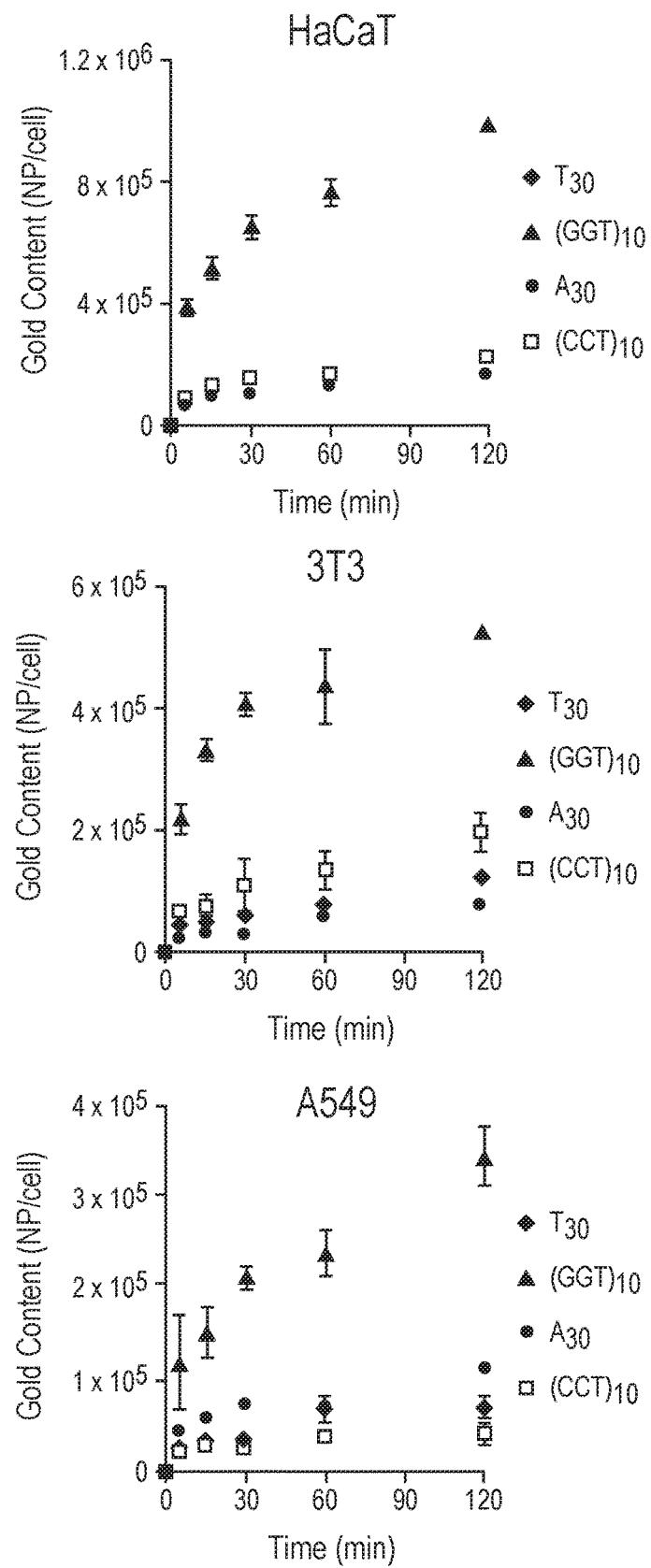

In summary, when the constituent oligonucleotide strands are kept constant at 30 bases long, incorporation of a higher fraction of Gs than other nucleobase types (i.e., A, C, T) maximizes the delivery of SNAs to C166 cells. To ascertain if such G-dependent uptake is only applicable to C166 cells, the cellular uptake kinetics of SNAs was further tracked for three other mammalian cell types, namely HaCaT, 3T3, and A549 (FIG. 5c). These cell lines, in conjunction with C166, have a range of expression levels for SR-A; in descending order of expression levels, they are HaCaT, C166, 3T3, and A549 [Choi et al., Proc Natl Acad Sci U.S.A. 110: 7625-7630 (2013)]. Consistent with the uptake data for C166 cells, poly G SNAs demonstrate the maximal extent of association for these cell types, exhibiting 4-10 fold higher cellular association than SNAs composed of other nucleobase types. Remarkably, cellular association of poly G SNAs is also positively correlated with the expression level of SR-A; when incubated with the same concentration of poly G SNAs, HaCaT, 3T3, and A549 cells exhibit highest, intermediate, and lowest cellular association, respectively. Thus, incorporation of Gs maximizes the delivery of SNAs to multiple mammalian cell types in a manner that is correlated with expression level of SR-A. In addition, these data show that oligonucleotide loading does not dictate the cellular uptake kinetics when the nucleobase type is not kept constant; despite their lower oligonucleotide loading, poly G SNAs enter cells in higher amounts than poly T SNAs.

Example 3

Figure 6A:
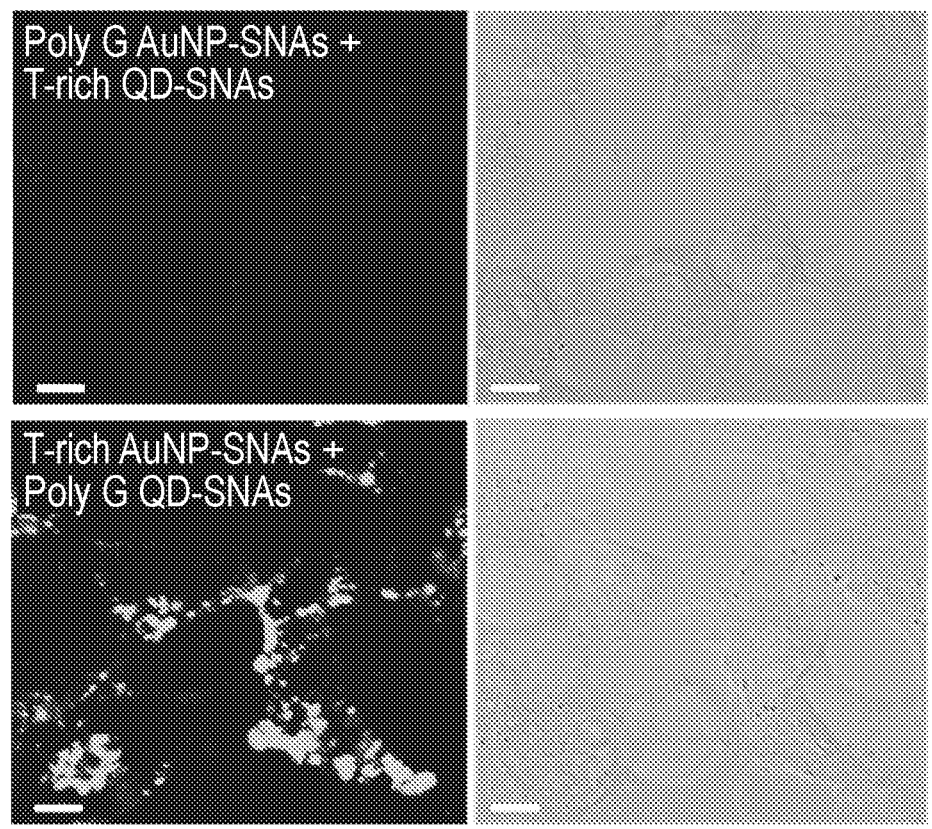
FIGS. 6a-6b shows the dependence of uptake on the poly G shell. 6a) By confocal microscopy, poly G QD-SNAs (red) show higher accumulation in C166 cells compared to T-rich QD-SNAs. Scale bar=10 μm. 6b) ICP-MS analysis of the gold and cadmium content in C166 cells treated with T-rich AuNP-SNAs and poly G QD-SNAs as well as T-rich QD-SNAs and poly G AuNP-SNAs shows that poly G AuNP-SNAs preferentially enter cells compared to T-rich QD-SNAs and poly G QD-SNAs preferentially enter cells compared to T-rich AuNP-SNAs. Error bars denote the standard deviation from three independent experiments.
Figure 6B:
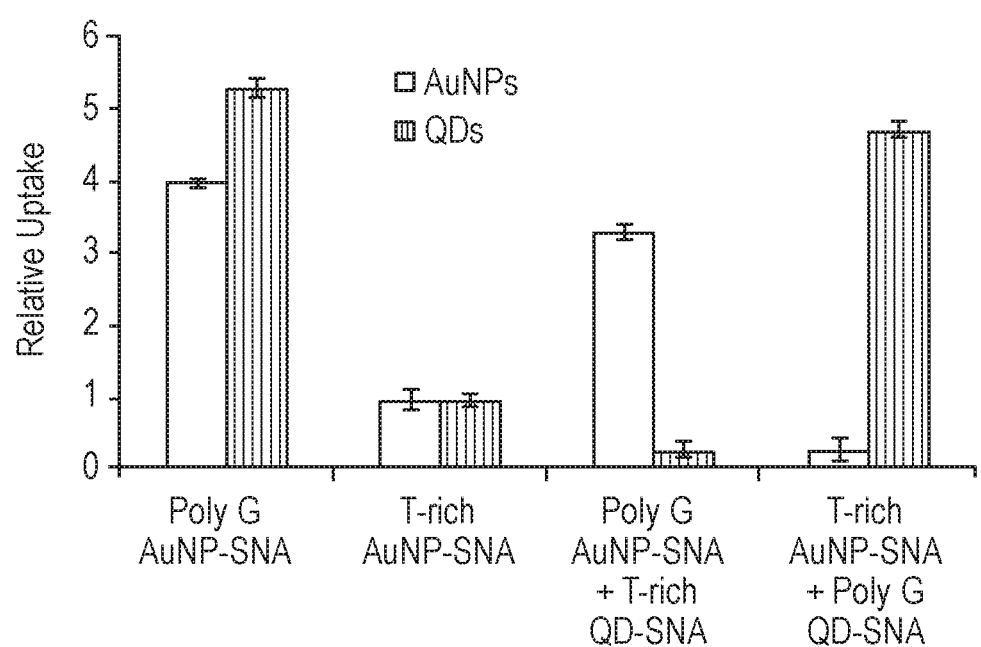

The Poly G Shell Maximizes Intracellular Delivery Regardless of Core Composition In order to prove that the poly G shell of poly G SNAs facilitates increased cellular uptake compared to poly A, poly T, and poly C SNAs, T-rich SNAs and poly G SNAs with different core compositions were synthesized, either 5 nm AuNPs or cadmium selenide (CdSe) quantum dots (QDs) (see Table 2) for sequence information). Five nanometer AuNP-SNAs and QD-SNAs comprised of oligonucleotides listed in Table 2 were prepared to study the effect of the poly G shell on the cellular uptake of SNAs of different core compositions (FIG. 6). All sequences are 28 bases long and terminated with a dibenzocyclooctyl (DBCO) group. The AuNP-SNAs and QD-SNAs were synthesized using a previously described strategy [Zhang et al., Nat Mater 12: 741-746 (2013), incorporated herein by reference in its entirety]. In one set of experiments, C166 cells were treated with equal concentrations of T-rich QD-SNAs and poly G AuNP-SNAs. In another set of experiments, cells were treated with equal concentrations of T-rich AuNP-SNAs and poly G QD-SNAs. Confocal microscopy was then used to track the fluorescent signal of the QDs that entered cells. C166 cells treated with T-rich QD-SNAs and poly G AuNP-SNAs showed very little intracellular fluorescence. However, C166 cells treated with T-rich AuNP-SNAs and poly G QD-SNAs showed significantly higher intracellular fluorescence (FIG. 6a), indicating a higher uptake of SNAs with a poly G shell into C166 cells. To further confirm, ICP-MS was used to analyze the Au content and Cd content in C166 cells treated with T-rich AuNP-SNAs or QD-SNAs alone, poly G AuNP-SNAs or QD-SNAs alone, a combination of T-rich AuNP-SNAs and poly G QD-SNAs, and a combination of T-rich QD-SNAs and poly G AuNP-SNAs. C166 cells treated with poly G AuNP-SNAs have 3 times higher Au content than cells treated with T-rich AuNP-SNAs. In contrast, cells treated with poly G QD-SNAs show three-fold higher Cd content than cells treated with T-rich QD-SNAs (FIG. 6b). Cells treated with poly G AuNP-SNAs and T-rich QD-SNAs have higher Au content compared to Cd content, and this trend is reversed for cells treated with T-rich AuNP-SNAs and poly G QD-SNAs (FIG. 6b). This competitive cellular uptake assay showed that SNAs with a poly G shell preferentially enter cells regardless of core composition, indicating that the poly G shell has greater affinity for cell surface receptors.

TABLE 2

List of SNA nanoparticle conjugates and their DNA oligonucleotide sequences.

| Type of SNA | Sequence of constituent DNA oligonucleotides (5'→3') | SEQ ID NO: |
|---|---|---|
| Poly G AuNP-SNA | GGT GGT GGT GGT GGT TTT TTT TTT TTT T DBCO | 5 |
| T-rich AuNP-SNA | TAT CGT ATT TAC TCT GAT TTT TTT TTT T DBCO | 6 |
| Poly G QD-SNA | GGT GGT GGT GGT GGT TTT TTT TTT TTT T DBCO | 7 |
| T-rich QD-SNA | TAT CGT ATT TAC TCT GAT TTT TTT TTT T DBCO | 8 |

Example 4

The Most Peripheral Approximately 10 Bases of an Oligonucleotide Dictates the Cellular Uptake of SNAs To characterize the cellular uptake properties from a geometric perspective, the fraction of DNA oligonucleotides that significantly contributes to the cellular uptake of SNAs was investigated. Again, the cellular association of SNAs when all constituent oligonucleotides are kept constant at 30 bases (see Table 3 for sequence information) was compared. SNAs comprised of oligonucleotides listed in Table 3 were prepared to probe the effects of nucleotide position on the cellular uptake of SNAs (FIG. 7). All sequences are 30-bases long and contain a minimum of six thymidylic acid (T) residues at the 3' end. This poly (T) motif at the 3' end allows for a near-constant loading of oligonucleotides onto the surface of AuNPs independent of sequence. A fraction of the oligonucleotides does not contain any nucleobases; these abasic regions were prepared by using either a dSpacer CE phosphoramidite (d; with both ribose unit and phosphate backbone) or a Spacer phosphoramidite C3 (c; with the phosphate backbone only).

Figure 7A:
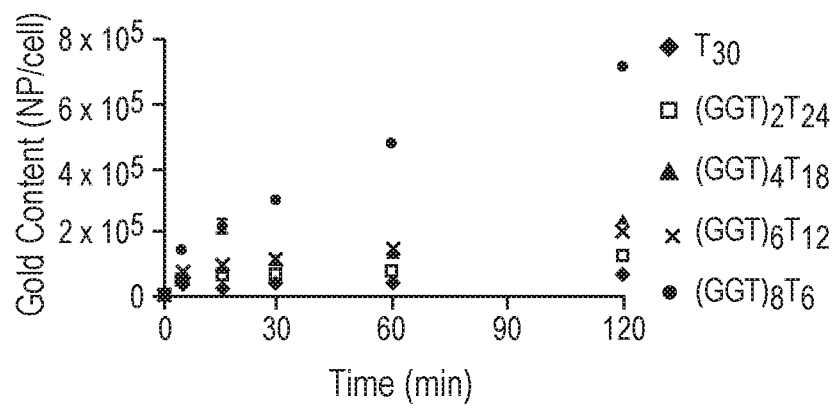
FIGS. 7a-7d depict that length of the oligonucleotide strand affects cellular uptake of SNAs. 7a) Increased guanylic acid (G) content at the 5' end of constituent oligonucleotides increases cellular association of SNAs with C166 cells. A minimum of four GGT repeating units is necessary to enhance cellular association of SNAs when compared to poly T (T30) SNAs. 7b) Burial of the GGT repeating units in the middle of the constituent oligonucleotides negates the enhancement in cellular association. The sequence shown by open squares is SEQ ID NO: 27. The sequence shown by open triangles is SEQ ID NO: 28. All other sequences are described herein. 7c) Increasing dSpacer units (which do not have a nucleobase) at the 5' end of constituent DNA oligonucleotides reduces cellular association of SNAs up to 75%. 7d) Increasing C3 Spacer units (which have neither a nucleobase nor a ribose) at the 5' end of constituent DNA oligonucleotides reduces cellular association of SNAs up to 75%. Error bars denote the standard deviation from triplicate measurements.

First, the cellular association between poly T SNAs and SNAs containing varying amounts of Gs at the 5' end (in the form of repeating GGT units) and Ts at the 3' end by ICP-MS were compared. The poly T segment at the 3' end of the DNA oligonucleotides allows for a near-constant oligonucleotide loading onto the surface of the AuNP. In general, cellular association of SNAs increases with increasing G content at the 5' end of the constituent oligonucleotides (FIG. 7a). It appears that a minimum of four GGT repeats at the 5' end of the constituent oligonucleotides is necessary to significantly enhance cellular association; addition of two GGT repeats does not substantially increase cellular association compared to poly T SNAs.

TABLE 3

List of SNA nanoparticle conjugates and their DNA oligonucleotide sequences

Figure 7B:
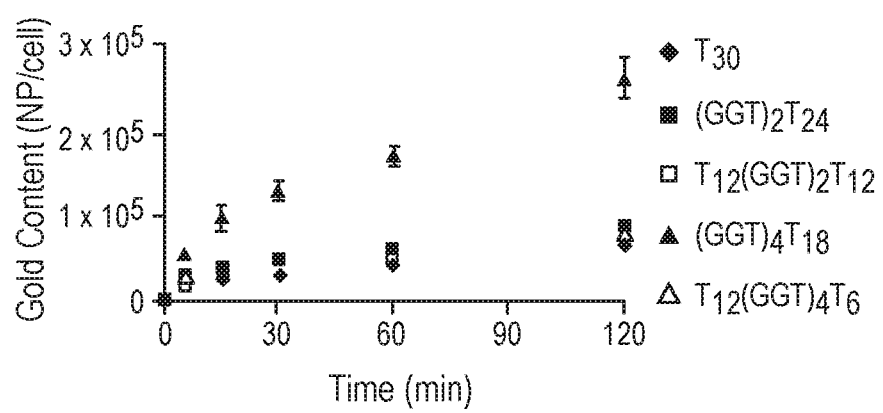
Figure 7C:
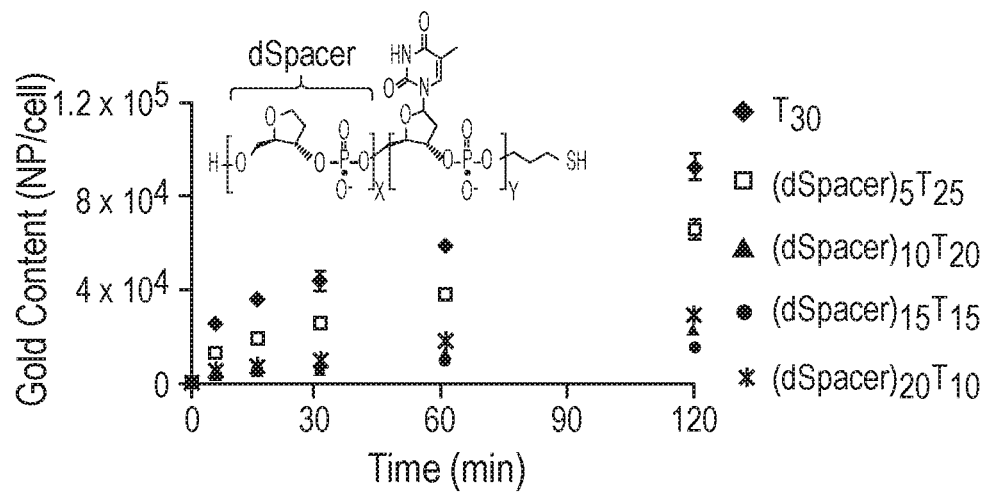
Figure 7D:
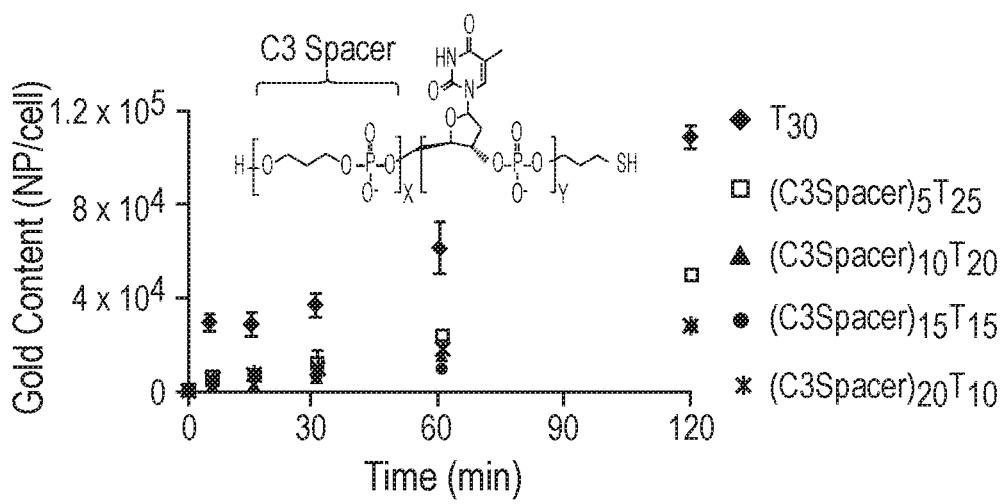

| Type of SNA | Sequence of constituent DNA oligonucleotides (5'→3') | SEQ ID NO: |
|---|---|---|
| $(GGT)_2T_{24}$ | GGT GGT TTT TTT TTT TTT TTT TTT TTT propylthiol | 9 |
| $(GGT)_4T_{18}$ | GGT GGT GGT GGT TTT TTT TTT TTT TTT TTT propylthiol | 10 |
| $(GGT)_6T_{12}$ | GGT GGT GGT GGT GGT GGT TTT TTT TTT TTT propylthiol | 11 |
| $(GGT)_8T_6$ | GGT GGT GGT GGT GGT GGT GGT GGT TTT TTT propylthiol | 12 |
| TGT2 | TTT TTT TTT TTT GGT GGT TTT TTT TTT TTT propylthiol | 13 |
| TGT4 | TTT TTT TTT TTT GGT GGT GGT GGT TTT TTT propylthiol | 14 |
| $(dS)_5T_{25}$ | ddd ddT TTT TTT TTT TTT TTT TTT TTT TTT propylthiol | 15 |
| $(dS)_{10}T_{20}$ | ddd ddd ddd dTT TTT TTT TTT TTT TTT propylthiol | 16 |
| $(dS)_{15}T_{15}$ | ddd ddd ddd ddd ddd TTT TTT TTT TTT TTT propylthiol | 17 |
| $(dS)_{20}T_{10}$ | ddd ddd ddd ddd ddd ddd ddT TTT TTT TTT propylthiol | 18 |
| $(C3)_5T_{25}$ | ccc ccT TTT TTT TTT TTT TTT TTT TTT TTT propylthiol | 19 |
| $(C3)_{10}T_{20}$ | ccc ccc ccc cTT TTT TTT TTT TTT TTT propylthiol | 20 |
| $(C3)_{15}T_{15}$ | ccc ccc ccc ccc ccc TTT TTT TTT TTT TTT propylthiol | 21 |
| $(C3)_{20}T_{10}$ | ccc ccc ccc ccc ccc ccc ccT TTT TTT TTT propylthiol | 22 | d = abasic site with both ribose unit and phosphate backbone
c = abasic site with the phosphate backbone only The cellular association of SNAs composed of oligonucleotides with GGT repeats either exposed at the 5' end or buried in the middle of the strand (see sequence information in Table 3) was also compared. Placing a $T_{12}$ motif on the 5' end to bury the GGT repeats in the middle of the DNA oligonucleotide strand reduced cellular association by approximately 70% when compared to the case in which GGT repeats are exposed at the 5' end, effectively curbing the superior effect of the GGT repeats on cellular uptake of SNAs (FIG. 7b). These observations showed that approximately 10 bases at the 5' end of the 30-base long constituent DNA oligonucleotides primarily dictate the cellular uptake properties of SNAs. Besides increasing the cellular uptake of poly T SNAs via the incorporation of more Gs, the portion of the SNA nanostructure most relevant to cellular uptake of poly T SNAs was also probed. To this end, SNAs that contain varying lengths of abasic spacers at the 5' end of constituent DNA oligonucleotides (see sequence information in Table 3) were constructed. These abasic spacers include dSpacer (Glen Research), which does not contain a nucleobase, and C3 spacer (Glen Research), which has neither a nucleobase nor a ring structure. SNAs with higher abasic spacer contents show approximately 75% lower cellular association compared to poly T SNAs (FIGS. 7c and 7d) that levels off when more than 10 abasic spacer units are added to the 5' end. Again, these data demonstrate that approximately one-third of the constituent oligonucleotide strands (10 out of a total of 30 bases at the 5' end) exposed at the most peripheral part of the SNA nanoparticle are most geometrically essential in determining its cellular association. They also reaffirm that the nucleobase, but not the phosphate backbone or ribose units, are the biochemically active components that dictate the cellular association of SNAs.

Example 5

Figure 8A:
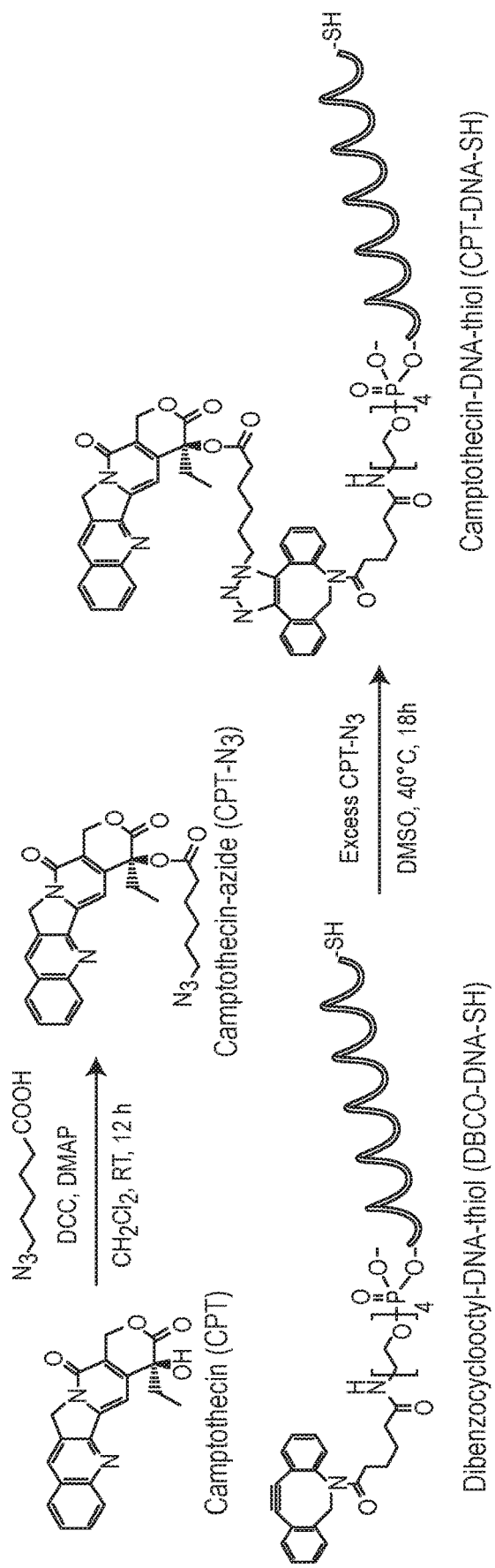

Poly G SNAs Can Maximize the Intracellular Delivery of a Small Molecule Chemotherapeutic (e.g. Camptothecin) to Cancer Cells In addition to empirical data afforded by ICP-MS measurements and TEM imaging, functional evidence that poly G SNAs enter mammalian cells most effectively out of all nucleobase types is also provided by demonstrating that an increase in cellular uptake of drug-containing SNAs corresponds to an increase in their cytotoxicity against cancer cells. As a proof-of-concept, camptothecin-containing SNAs (CPT-SNAs) were prepared by covalently attaching camptothecin (CPT), a small-molecule chemotherapeutic agent, to the most peripheral position of their constituent oligonucleotides and subsequently examined their ability to kill cancer cells as a function of nucleobase type. A549 human lung adenocarcinoma epithelial cells (as discussed in FIG. 5c) were chosen as the model cell line because of their low expression of SR-A and caveolin-1, both of which are essential proteins for the cellular uptake of SNAs [Choi et al., Proc Natl Acad Sci U.S.A. 110: 7625-7630 (2013)]. Given the modest degree of cellular uptake of SNAs by A549 cells, any observable cytotoxicity highlights the potency of CPT-SNAs as a function of nucleobase type. To attach CPT molecules onto DNA strands, literature precedent was followed to react the —OH group of CPT with an azide-bearing linker to synthesize camptothecin-azide (CPT-N3) [Parrish et al., Bioconjug Chem 18: 263-267 (2007)]. Copper-free click chemistry was utilized for coupling CPT-N3 directly onto bifunctional single-strand DNAs (ssDNAs) that bear a dibenzocyclooctyl (DBCO) group on one end as well as a thiol group on the other. The resultant conjugate, camptothecin-DNA-thiol (CPT-DNA-SH), can then be covalently attached to the surface of AuNPs as previously described, yielding CPT-SNAs (FIGS. 8a and 9).

TABLE 4

Figure 9A:
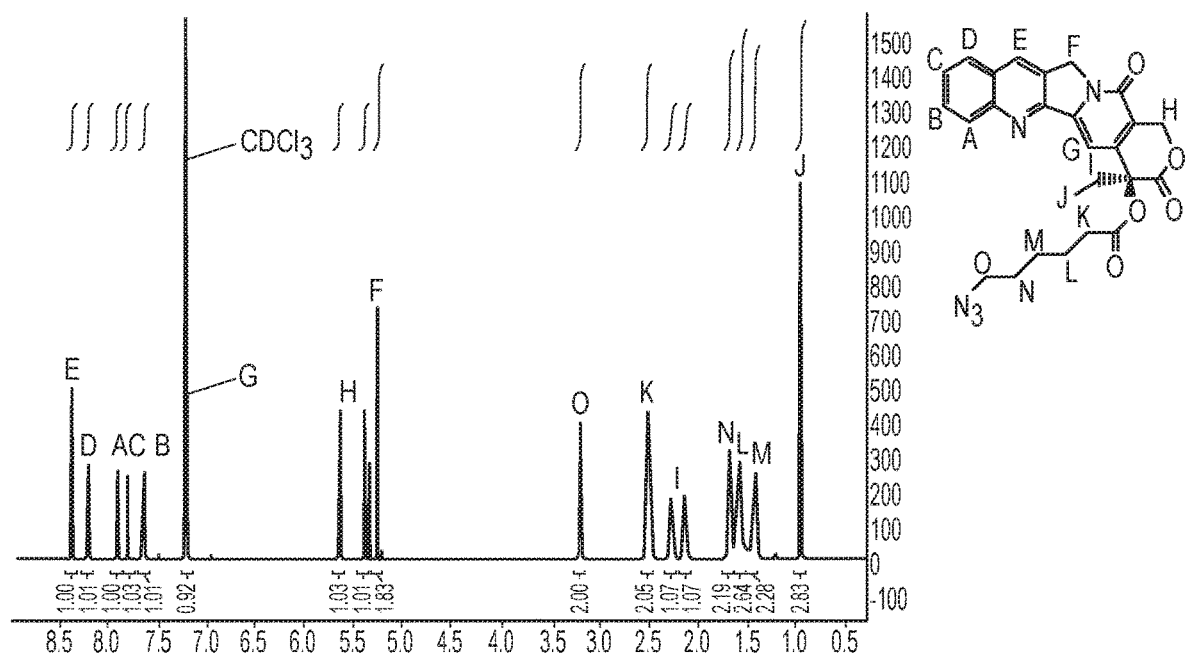
Figure 9B:
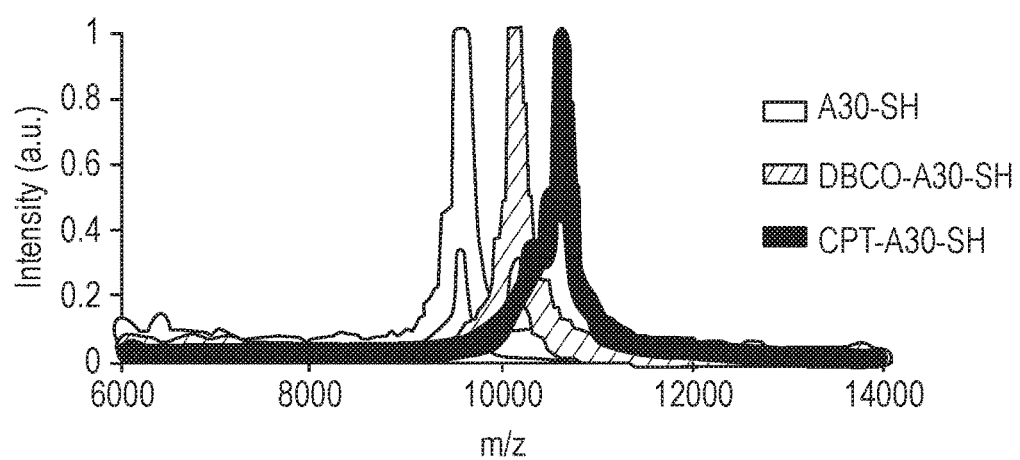

Sequences as shown in FIG. 9d.

| Type of SNA | Sequence of constituent DNA oligonucleotides (5'→3') | SEQ ID NO: |
|---|---|---|
| CPT-poly A SNA ($A_{30}$) | CPT-AAA AAA AAA AAA AAA AAA AAA AAA AAA AAA-propylthiol | 23 |
| CPT-poly T SNA ($T_{30}$) | CPT-TTT TTT TTT TTT TTT TTT TTT TTT TTT TTT-propylthiol | 24 |
| CPT-poly C SNA (($CCT)_{10}$) | CPT-CCT CCT CCT CCT CCT CCT CCT CCT CCT CCT-propylthiol | 25 |
| CPT-poly G SNA (($GGT)_{10}$) | CPT-GGT GGT GGT GGT GGT GGT GGT GGT GGT GGT-propylthiol | 26 |

Figure 8D:
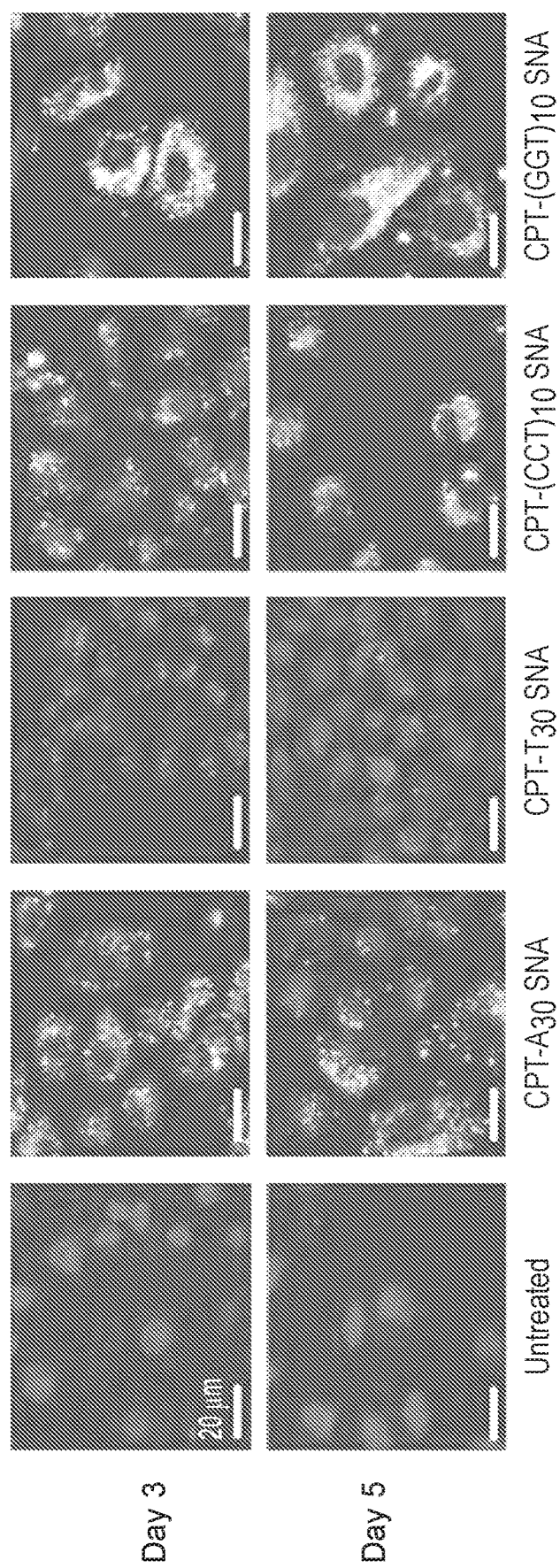
Figure 10:
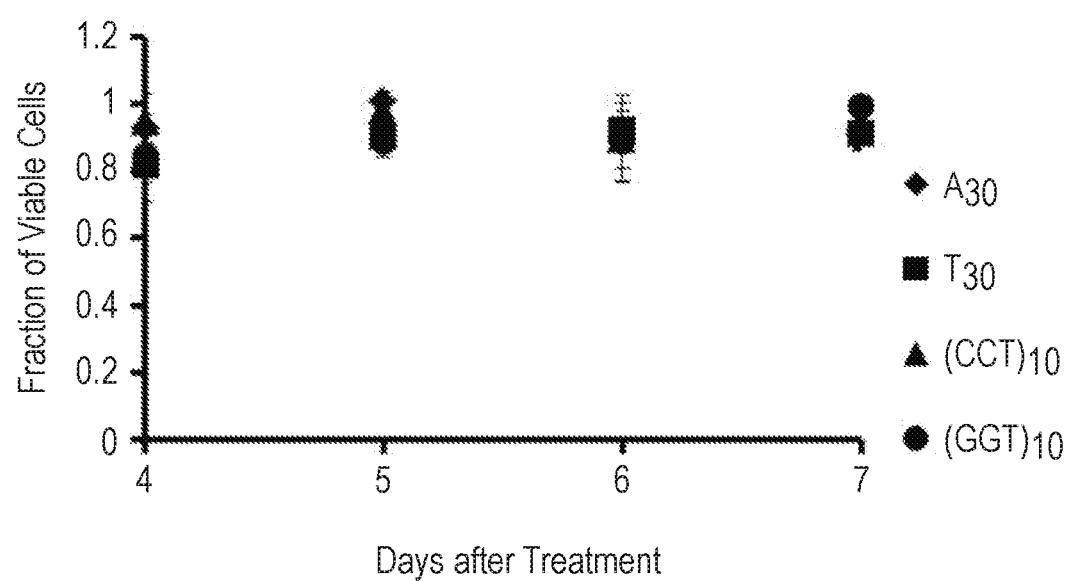
FIG. 10 shows cell viability by MTT assay. Without CPT molecules, poly A SNAs, poly T SNAs, poly C SNAs, and poly G SNAs show no appreciable cytotoxicity after 4-7 days by MTT assay on A549 cells treated with 20 nM SNAs. This negative control showed that any observable cytotoxicity induced by CPT-SNAs stems from the CPT molecule, not the SNA architecture. Reported values represent mean±SE from the average of three independent experiments.

Using this approach, CPT-poly A SNAs, CPT-poly T SNAs, CPT-poly C SNAs, and CPT-poly G SNAs were prepared. Given that the oligonucleotide loading for poly T SNAs and poly C SNAs is significantly higher than that for poly A SNAs and poly G SNAs, the CPT-$T_{30}$-SH strands were intentionally diluted with unmodified $T_{30}$-SH strands and the CPT-$(CCT)_{10}$-SH strands were diluted with unmodified $(CCT)_{10}$-SH strands as the strands were functionalized onto AuNPs, in order to obtain a similar loading of CPT molecules on SNAs composed of all nucleobase types, which allowed for the direct comparison of the effect of enhanced cellular uptake of poly G SNAs on CPT delivery. Indeed, the loading of camptothecin molecules per particle was determined to be approximately equal (approximately 55±15 CPT molecules per AuNP) (FIG. 8b). The effect of nucleobase type on the uptake of CPT-SNAs by A549 cells was next investigated by measuring the gold content associated with the cells using ICP-MS. After incubation for 9 hours and 18 hours, CPT-poly G SNAs show 6-9 fold higher association with A549 cells than CPT-SNAs composed of other nucleobase types. This observation reinforced the conclusion that the 10 most peripheral bases of DNA oligonucleotides covalently functionalized on the surface of AuNPs are most significant in dictating the cellular uptake properties of SNAs. That is, a small-molecule drug placed at the periphery of SNAs does not significantly interfere with the interaction between the DNA oligonucleotides and cell-surface SR-A. CPT-SNAs were further incubated with A549 cells for 18 hours, replenished with fresh nanoparticle-free medium, and allowed to grow for an additional 54 hours. After 72 hours, the gold content associated with the cells was similar to the gold content associated with cells after 18 hours, implying little appreciable exocytosis of CPT-SNAs (FIG. 8c). Besides tracking the AuNP core of CPT-SNAs by ICP-MS, the distribution of CPT in A549 cells was visualized by confocal imaging, taking advantage of the fluorescent emission of the CPT molecule at 440 nm [Zamai et al., Mol Cancer Ther 2: 29-40 (2003)]. After incubation of CPT-SNAs with A549 cells for 18 hours, the particles were removed, replenished with fresh medium, and imaged 3 and 5 days after treatment. After 3 days, CPT-poly G SNAs showed the highest intracellular accumulation of CPT among all nucleobase types tested. After 5 days, cells treated with CPT-poly G SNAs still showed the highest fluorescence, but the fluorescence was more diffuse (FIG. 8d). Based on the ICP-MS and confocal imaging data, and without being bound by theory, it is contemplated that CPT-SNAs persist in cells for a sufficient period of time to release the CPT molecules gradually by the action of intracellular esterases and exert a cytotoxic effect [Cheng et al., Bioconjug Chem 14: 1007-1017 (2003)]. To test this, 20 nM CPT-SNAs (or equivalently, approximately 1.1 µM CPT molecules) were incubated with different sequences with A549 cells for 18 hours, the cells were replenished with fresh medium, and their viability was measured several days later by using a modified MTT assay. Between 4 and 7 days after CPT-SNA treatment, CPT-poly G SNAs are significantly more cytotoxic than CPT-SNAs composed of other nucleobase types. After 7 days, cells treated with CPT-poly G SNAs show only approximately 20% cell viability compared to 80-100% viability for cells treated with CPT-SNAs composed of other nucleobase types (FIG. 8e). As a negative control, A549 cells were also incubated with 20 nM CPT-free SNAs composed of all nucleobase types for 18 hours and no appreciable cytotoxicity was observed 7 days after treatment (FIG. 10), confirming that the observed cytotoxicity induced by CPT-SNA treatment originates from the attached CPT molecule but not the SNA architecture itself.

Figure 11:
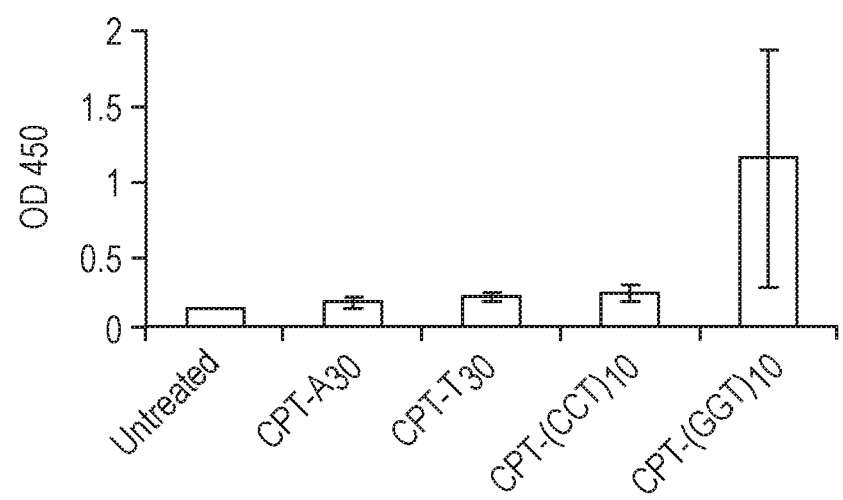
FIG. 11 shows ELISA results for detecting activated caspase 3. Upon treatment of A549 cells with various types of CPT-SNAs, CPT-$(GGT)_{10}$ SNAs induce significantly higher activation of caspase 3, an apoptotic signaling protein, than CPT-$A_{30}$ SNAs, CPT-$T_{30}$ SNAs, and CPT-$(CCT)_{10}$ SNAs. Reported values represent mean±SE from the average of three independent experiments.

In addition, cells were stained with propidium iodide 6 days after treatment with CPT-SNAs to detect CPT-induced apoptosis. Flow cytometry of the stained cells reveals that CPT-$(GGT)_{10}$ SNAs are the most cytotoxic (FIG. 8f). To further ensure that CPT is active in the cells, the amount of activated caspase 3, an apoptotic signaling protein that is known to be activated by CPT [Stefanis et al., J Neurosci 19: 6235-6247 (1999)], was measured in cells by ELISA after 5 days. Cells treated with CPT-poly G SNAs show a higher amount of activated caspase 3 than cells treated with CPT-$A_{30}$, CPT-$T_{30}$, and CPT-$(CCT)_{10}$ SNAs (FIG. 11). In summary, CPT-poly G SNAs are significantly more potent than CPT-SNAs composed of other nucleobase types, as evidenced by increased delivery of CPT to cancer cells by poly G SNAs and increased cytotoxicity. This example underscores the functional advantage of G-dependent delivery and demonstrates the potential of delivering other therapeutic entities with greater efficiency.

Conclusion

Demonstrated by the foregoing non-limiting examples are methods for increasing the uptake of SNA nanoparticle conjugates into cells. SNAs with a three-dimensional oligonucleotide shell containing a high G content are internalized by cells in higher amounts than SNAs that are primarily composed of A, T, and C. Further, G-rich SNAs can be used to enhance the intracellular delivery of both nucleic acids and small molecule drugs. This indicates that sequence composition is another tunable property, in addition to concentration, that can be used to tailor the intracellular delivery of SNAs. This strategy of tailoring sequence composition is a powerful tool for nanoparticle-based diagnostic and therapeutic applications because it enables the rational design of nanoparticle constructs with desired cellular uptake properties.

Example 6

Materials and Methods

The following materials and methods were used to generate the data described in the foregoing examples.

Synthesis of DNA oligonucleotides. DNAs were synthesized on an MM48 Oligonucleotide synthesizer (BioAutomation) using standard solid-phase synthesis and reagents (Glen Research). Unless otherwise mentioned, all DNAs were purified using a ProStar HPLC (Varian) with a Microsorb C18 column (Varian). Table 1 contains detailed sequence information of the DNAs.

Preparation of spherical nucleic acid (SNA) nanoconjugates. Thiolated DNAs were added to 10 nm citrate-capped AuNPs at a concentration of 1 OD of DNA per mL of 10 nM AuNPs supplemented with 0.1% Tween 20. After stirring at room temperature for 1 hour, the solution was aged with gradual additions of NaCl over 6 hours to bring the final NaCl concentration to 0.5 M. Functionalized AuNPs were separated from free DNA strands via dialysis against Nanopure water using a 50-kDa Amicon MWCO membrane (Millipore). AuNP and DNA concentrations were determined by measuring their extinction at 524 nm and 260 nm, respectively, on a Cary 5000 UV-Vis spectrophotometer (Agilent). To prepare camptothecin-containing SNAs (CPT-SNAs), the solution was aged with NaCl over 5 hours to bring the final NaCl concentration to 0.3 M.

Measurement of oligonucleotide loading. Ten microliters (μL) of 10 nM Cy5-labeled SNAs of different nucleobase types was added into 100 μL of 1 M DTT. The mixture was incubated at 40° C. for 15 minutes with shaking, followed by centrifugation at 14000×g to remove any gold precipitate. One hundred μL of the supernatant was placed in a 96-well plate and the fluorescence signals (excitation: 633 nm; emission filter: 660-710 nm) were measured using a Synergy H4 Multimode Microplate Reader (Biotek). The concentration of oligonucleotides was determined by comparing to a calibration standard curve. Dividing oligonucleotide concentration by AuNP concentration (measured by UV-Vis spectroscopy at 520 nm) yields the oligonucleotide loading.

Visualization of the oligonucleotide shell. Twenty μL of 100 nM SNAs was drop-cast onto each glow-discharged, 200-mesh copper grid coated with carbon and formvar (Electron Microscopy Sciences). Upon drying, 20 μL of 2% uranyl acetate was added onto the grids to stain the oligonucleotide shell for 1 minute. Excess uranyl acetate was blotted away using a piece of filter paper. The dried grids were imaged using a HD-2300 (Hitachi) microscope in TEM mode at a beam voltage of 80 kV. An Orius SC 1000 CCD camera (Gatan) was used to record the images.

Cellular uptake kinetics. Seeded in a 24-well plate at a population of 5×10$^4$ cells per well 12 hours in advance, C166 (mouse endothelial), 3T3 (mouse fibroblast), HaCaT (human keratinocyte), or A549 (human lung adenocarcinoma epithelial) cells were incubated with 0.3 mL of SNAs (10 nM in OptiMEM) per well at 37° C. and 5% $CO_2$. SNAs were removed at different time points, followed by OptiMEM rinses, trypsinization for counting using a hemacytometer, and centrifugation at 8000 rpm for 5 minutes to form a pellet. Cell pellets were digested with 0.3 mL of 3% HCl in concentrated $HNO_3$ at room temperature (RT) overnight for subsequent ICP-MS analysis.

ICP-MS. After adding 5 μL of 5 ppm indium (internal standard) and 5 mL of matrix solution (2% HCl and 2% $HNO_3$), the Au-197 content of the resultant solution was measured by an X Series II ICP-MS (ThermoFisher) after subtracting the background gold content of untreated cells. Reported values represent mean±SE from the average of three independent experiments.

TEM. Cell pellets were mixed gently in 0.2 mL of molten 2% agarose in 50 mM sodium phosphate buffer (pH=8) at 40° C. for 5 minutes. The cell-agarose mixture was expunged into water at RT gently using a glass pipette to form an enrobed noodle-shaped jelly. Embedded in this agarose jelly, cells were fixed in 2.5% glutaraldehyde in 100 mM sodium cacodylate buffer (pH=7.4), stained by 1% $OsO_4$, and by 0.9% $OsO_4$ and 0.3% $K_4Fe(CN)_6$, with all steps carried out at 4° C. for 2 hours. After gradual dehydration with ethanol and propylene oxide, cell pellets were embedded in Epon 812 resins (Electron Microscopy Sciences). Eighty-nanometer-thick sections were deposited onto 200-mesh copper grids (EMS) and stained with 2% uranyl acetate (SPI Supplies) and Reynolds lead citrate for visualization under a JEM 1230 microscope (JEOL) using a beam voltage of 80 kV. An Orius SC 1000 CCD camera (Gatan) was used to record the images.

Synthesis of quantum dot and gold nanoparticle SNAs. Instead of covalently attaching DNAs strands directly to the nanoparticle surface, the CdSe quantum dots and 5 nm gold nanoparticles were first coated with an azide-bearing amphiphilic polymer, then coupled the DNA to the polymer-coated particles using strain-promoted azide-alkyne cycloaddition. Briefly, commercially available hydrophobic-ligand-capped nanoparticles were first functionalized with an amphiphilic polymer containing both hydrophobic alkyl chains and hydrophilic carboxylates and azide-modified ethylene glycol groups to solubilize the particles in aqueous solvent. The particles were then functionalized by azide-alkyne click chemistry with dibenzocyclooctyl (DBCO)-terminated DNA strands to produce a dense DNA shell around the nanoparticle.

Preparation of camptothecin-azide. The preparation for camptothecin-azide (CPT-$N_3$) was adapted and modified from previously published procedures [Parrish et al., Bioconjugate Chem. 18: 263-267 (2006)]. To an oven-dried 50 mL round bottomed flask with stirrer was added camptothecin (200 mg, 0.54 mmol), 6-azidohexanoic acid (170 mg, 1.08 mmol), 4-dimethylaminopyridine (8 mg), and dry dichloromethane (10 mL). The suspension was cooled to 0° C. and 1,3-dicyclohexylcarbodiimide (220 mg, 1.08 mmol) was added. The reaction mixture was stirred for 12 hours under inert atmosphere, warmed to RT, and then poured into 100 mL of ether. The ether suspension was cooled to 0° C. to precipitate dicyclohexylurea (DCU), and the solids were removed by vacuum filtration. The filtrate was cooled to −40° C., and the resulting yellow precipitate collected and recrystallized from methanol to afford 20-O-(6-azidohexanoyl)camptothecin (108 mg). The recovered DCU was washed repeatedly with methanol, yielding an additional crop of product (120 mg; total yield 228 mg, 87%).

Preparation of camptothecin-DNA-thiol (CPT-DNA-SH) conjugate. Single-stranded DNA of various sequences (FIG. 9d), all possessing a dibenzocyclooctyl (DBCO) group at their 5' end, were made by solid-state synthesis using a DBCO-TEG phosphoramidite (Glen Research, 10-1941). Purification of DNA-DBCO conjugates was performed using a 1200 Series HPLC (Agilent) by collecting the fraction with an absorbance peak of DBCO at 310 nm. To attach the CPT moiety to the DNA by copper-free click chemistry, 80 nmol of DNA-DBCO and 3 mg of CPT-azide (approximate 100-fold excess) were dissolved in 1.5 mL of anhydrous dimethyl sulfoxide. The reaction was shaken continuously for 18 hours at 40° C. After that, 3.5 mL of deionized water was added to the mixture to precipitate out the excess CPT, followed by adding 5 mL of ethyl acetate to remove the CPT. The liquid-liquid extraction process was repeated for four more times. The aqueous phase (DNA-CPT in DMSO/water) was lyophilized to retrieve the product, whose chemical identity was confirmed by MALDI-ToF.

Confocal microscopy. Seeded in a 35 mm FluoroDish (World Precision Instruments), A549 cells were incubated with 20 nM of CPT-SNAs in OptiMEM for 18 hours.

CPT-SNAs were removed from cells and replaced with complete DMEM (DMEM supplemented by 10% fetal bovine serum and 1% penicillin/streptomycin) for either 3 or 5 days. The treated cells were rinsed with PBS, fixed in 3.7% paraformaldehyde in PBS for 15 minutes, and stained with Hoechst nuclear stain for imaging under a Zeiss LSM 510 inverted confocal scanning microscope. The excitation and emission wavelengths of CPT were 370 nm and 440 nm, respectively.

MTT assay. Seeded in a 24-well plate at a population of $10^4$ cells per well, A549 cells were incubated with 0.3 mL of SNAs (20 nM in OptiMEM) for 18 hours. After that, SNAs were removed from the cells, which were then incubated with 1 mL of complete DMEM. After different durations of time, 20 μL of MTT stock solution (5 mg/mL MTT in PBS; Molecular Probes) was added into each well of cells that were pre-incubated with 300 μL of complete DMEM. After 2 hours, 300 μL of SDS solution (200 mg/mL in 50% dimethyl formamide) was further added into each well, followed by thorough pipetting to re-suspend the cells. Upon overnight incubation, the cell lysate was centrifuged at 14000×g for 10 minutes to remove any gold aggregates. The absorbance at 620 nm of the supernatant fraction collected from the cell lysate was determined using a Synergy H4 Multimode Microplate Reader (Biotek). Reported values represent mean±SE from the average of three independent experiments.

Flow cytometry. Seeded in a 6-well plate, A549 cells were incubated with 1 mL of SNAs (20 nM in OptiMEM) for 18 hours. Upon treatment, CPT-SNAs were removed and the cells grown on complete DMEM for 126 hours. Cells were then trypsinized, washed, and suspended in 0.5 mL PBS. 0.5 mL 3.7% paraformaldehyde was added to the cell suspension from each well for 15 minutes. After two PBS rinses, cells were stained using 1 mL of propidium iodide (Santa Cruz Biotechnology, sc-3541) staining solution in PBS working solution (50 mg/mL). Stained samples were stored at 4° C. and were protected from light prior to flow cytometry analysis. The fluorescence intensity of 10,000 cells was measured using a BD LSR II flow cytometer.

Chemicals. 6-Azidohexanoic acid was purchased from EMD Millipore (Billerica, Mass.). CdSe quantum dots were purchased from Ocean NanoTech. Dodecanethiol-functionalized Au nanoparticles were purchased from Nanoprobes. DBCO-NHS ester was purchased from Clickchemistrytools. All other reagents were purchased from Sigma-Aldrich (St. Louis, Mo.) and used as received.

Dynamic Light Scattering. Measurements were conducted using a Nano Zetasizer (Malvern Instruments), using 0.47 as the refractive index of AuNPs. Hydrodynamic diameter (HD) measurements are derived from the number average value. Each histogram represents the size distribution of AuNPs after six repeated measurements.

MALDI-ToF MS. Matrix-assisted laser desorption/ionization time-of-flight (MALDI-ToF) data was collected on a Bruker AutoFlex III MALDI-ToF mass spectrometer employing 2,5-dihydroxyacetophenone (DHAP) as the matrix material.

$^1$H NMR. $^1$H NMR spectra were recorded on a Bruker Avance 400 MHz NMR spectrometer. $^1$H NMR spectra were referenced internally to residual proton signals in the deuterated solvent.

Detection of activated caspase 3. A549 cells were plated in a 6-well plate at a density of 100,000 cells per well and treated with 20 nM CPT-SNAs in OptiMEM. After 18 hours, the cells were washed with PBS and further incubated with complete DMEM (supplemented with 10% fetal bovine serum and 1% streptomycin/penicillin). After 6 days, the cells were lysed and protein extracted. Relative levels of activated caspase 3 were detected by ELISA according to manufacturers' instructions (Cell Signaling 7190S).

What is claimed is:

1. A nanoparticle functionalized with a polynucleotide, wherein the polynucleotide comprises a domain, wherein the domain (i) is situated at the terminus of the polynucleotide that is distal to the nanoparticle and (ii) terminates in three to fifteen consecutive (GGX) motifs, wherein X is not guanylic acid or cytidylic acid, wherein the polynucleotide is 9 to 70 nucleotides in length, and wherein the nanoparticle is functionalized with an additional polynucleotide comprising a sequence sufficiently complementary to a target polynucleotide sequence to hybridize to the target polynucleotide sequence.

2. The nanoparticle of claim 1 wherein the domain is located at the 5' terminus of the polynucleotide.

3. The nanoparticle of claim 1 wherein the domain is located at the 3' terminus of the polynucleotide.

4. The nanoparticle of claim 1 wherein X is a deoxyribonucleotide or a ribonucleotide.

5. The nanoparticle of claim 1 wherein X is adenylic acid, thymidylic acid, or uridylic acid.

6. The nanoparticle of claim 1 wherein X is a modified nucleotide.

7. The nanoparticle of claim 1 wherein the additional polynucleotide comprises a domain, wherein the domain (i) is situated at the terminus of the polynucleotide that is distal to the nanoparticle and (ii) terminates in three to fifteen consecutive (GGX) motifs, wherein X is not guanylic acid or cytidylic acid.

8. The nanoparticle of claim 1 wherein the domain comprises a poly guanylic acid (poly G) sequence comprising six, seven, eight, nine, ten, eleven, twelve, thirteen, fourteen, fifteen, sixteen, seventeen, eighteen, nineteen, or twenty guanylic acid nucleotides.

9. The nanoparticle of claim 1 wherein the polynucleotide is DNA.

10. The nanoparticle of claim 1 wherein the polynucleotide is RNA.

11. The nanoparticle of claim 1 wherein the additional polynucleotide is DNA or RNA.

12. A method comprising the step of: modifying a nanoparticle functionalized with a polynucleotide to further comprise a domain that increases cellular uptake of the nanoparticle compared to a nanoparticle functionalized with a polynucleotide lacking the domain, wherein the domain is (i) situated at the terminus of the polynucleotide that is distal to the nanoparticle and (ii) terminates in three to fifteen consecutive (GGX) motifs, wherein X is not guanylic acid or cytidylic acid, wherein the polynucleotide is 9 to 70 nucleotides in length, and wherein the nanoparticle is functionalized with an additional polynucleotide comprising a sequence sufficiently complementary to a target polynucleotide sequence to hybridize to the target polynucleotide sequence.

13. The method of claim 12 wherein the domain comprises a poly G sequence comprising six, seven, eight, nine, ten, eleven, twelve, thirteen, fourteen, fifteen, sixteen, seventeen, eighteen, nineteen, or twenty guanylic acid nucleotides.

14. The method of claim 12 wherein the domain is located at the 5' terminus of the polynucleotide.

15. The method of claim 12 wherein the domain is located at the 3' terminus of the polynucleotide.

16. The method of claim 12 wherein the polynucleotide is DNA or RNA.

17. The nanoparticle of claim 1 wherein the domain comprises a sequence that is at least 50%, at least 55%, at least 60%, at least 65%, at least 70%, at least 75%, at least 80%, at least 85%, at least 90%, or at least 95% guanylic acid nucleotide.

18. The nanoparticle of claim 1 wherein the additional polynucleotide detects the target polynucleotide.

19. The nanoparticle of claim 1 wherein the additional polynucleotide inhibits gene expression of the target polynucleotide sequence.

20. The method of claim 12 wherein hybridizing of the target polynucleotide sequence results in detection of the target polynucleotide sequence.

21. The method of claim 12 wherein hybridizing of the target polynucleotide sequence results in inhibition of gene expression of the target polynucleotide sequence.

22. The method of claim 12 wherein the domain comprises a sequence that is at least 50%, at least 55%, at least 60%, at least 65%, at least 70%, at least 75%, at least 80%, at least 85%, at least 90%, or at least 95% guanylic acid nucleotide.

23. The method of claim 21 wherein gene expression is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to inhibition of gene expression of a nanoparticle functionalized with a polynucleotide lacking the domain.

24. The method of claim 12 wherein the additional polynucleotide is DNA or RNA.

25. The nanoparticle of claim 1, wherein the polynucleotide is 9 to 45 nucleotides in length.

26. The nanoparticle of claim 1, wherein the domain is associated directly with the nanoparticle.

27. The nanoparticle of claim 1, wherein the domain is associated with the nanoparticle through a spacer.

28. The nanoparticle of claim 27, wherein the spacer does not comprise a nucleobase.

29. The nanoparticle of claim 27, wherein the spacer is an abasic spacer.

30. The nanoparticle of claim 27, wherein the spacer is a dSpacer or a C3 Spacer.

31. The nanoparticle of claim 27, wherein the spacer comprises ethylglycol.

32. The nanoparticle of claim 1, wherein the additional polynucleotide is an siRNA.

33. The method of claim 12, wherein the additional polynucleotide is an siRNA.

34. The nanoparticle of claim 1, wherein the polynucleotide is functionalized to the surface of the nanoparticle.

35. The method of claim 12, wherein the polynucleotide is functionalized to the surface of the nanoparticle.

* * * * *